US012680089B2

(12) United States Patent
Georgiou et al.

(10) Patent No.: US 12,680,089 B2
(45) Date of Patent: *Jul. 14, 2026

(54) ADMINISTRATION OF KYNURENINE DEPLETING ENZYMES FOR TUMOR THERAPY

(71) Applicant: BOARD OF REGENTS, THE UNIVERSITY OF TEXAS SYSTEM, Austin, TX (US)

(72) Inventors: George Georgiou, Austin, TX (US); Everett Stone, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 693 days.

This patent is subject to a terminal disclaimer.

(21) Appl. No.: 18/065,451

(22) Filed: Dec. 13, 2022

(65) Prior Publication Data

US 2024/0091258 A1      Mar. 21, 2024

Related U.S. Application Data

(62) Division of application No. 16/996,806, filed on Aug. 18, 2020, now Pat. No. 11,534,463, which is a division of application No. 16/373,588, filed on Apr. 2, 2019, now Pat. No. 10,772,913, which is a division of application No. 15/351,060, filed on Nov. 14, 2016, now abandoned, which is a division of application No. 14/473,040, filed on Aug. 29, 2014, now Pat. No. 9,808,486.

(60) Provisional application No. 61/986,366, filed on Apr. 30, 2014, provisional application No. 61/872,132, filed on Aug. 30, 2013.

(51) Int. Cl.
| | |
|---|---|
| *C12N 9/14* | (2006.01) |
| *A61K 35/17* | (2025.01) |
| *A61K 38/00* | (2006.01) |
| *A61K 38/46* | (2006.01) |

(52) U.S. Cl.
CPC ............... *C12N 9/14* (2013.01); *A61K 35/17* (2013.01); *A61K 38/46* (2013.01); *C12Y 307/01003* (2013.01); *A61K 38/00* (2013.01)

(58) Field of Classification Search
CPC .. C12Y 307/01003; A61P 43/00; A61P 35/00; C12N 9/14; A61K 35/17; A61K 38/46; A61K 38/00
See application file for complete search history.

(56) References Cited

U.S. PATENT DOCUMENTS

| | | | |
|---|---|---|---|
| 6,812,339 | B1 | 11/2004 | Venter et al. |
| 7,109,304 | B2 | 9/2006 | Hansen et al. |
| 7,714,139 | B2 | 5/2010 | Prendergast et al. |
| 8,377,976 | B2 | 2/2013 | Combs et al. |
| 8,465,743 | B2 | 6/2013 | Rosenberg et al. |
| 9,808,486 | B2 | 11/2017 | Georgiou et al. |
| 9,975,959 | B2 | 5/2018 | Georgiou et al. |
| 10,772,913 | B2 * | 9/2020 | Georgiou ............... A61K 38/46 |
| 11,168,142 | B2 | 11/2021 | Georgiou et al. |
| 11,534,463 | B2 * | 12/2022 | Georgiou ............... A61K 38/46 |
| 11,542,486 | B2 | 1/2023 | Georgiou et al. |
| 11,648,272 | B2 | 5/2023 | Georgiou et al. |
| 2003/0194721 | A1 | 10/2003 | Mikita et al. |
| 2009/0304666 | A1 | 12/2009 | Harrison |
| 2015/0064154 | A1 | 3/2015 | Georgiou |
| 2016/0058845 | A1 | 3/2016 | Georgiou et al. |
| 2017/0056449 | A1 | 3/2017 | Georgiou |
| 2019/0002579 | A1 | 1/2019 | Georgiou et al. |
| 2019/0350975 | A1 | 11/2019 | Georgiou et al. |
| 2020/0054674 | A1 | 2/2020 | Georgiou |
| 2021/0207110 | A1 | 7/2021 | Georgiou et al. |

FOREIGN PATENT DOCUMENTS

| | | | |
|---|---|---|---|
| CA | 2672380 A1 * | 6/2008 | ............... A61P 3/00 |
| CN | 1442487 | 9/2003 | |
| JP | 2006-521378 | 9/2006 | |
| JP | 2008-237022 | 10/2008 | |
| JP | 2010-504346 | 2/2010 | |
| KR | 10-2012-0085209 | 7/2012 | |
| WO | WO 2003/065984 | 8/2003 | |
| WO | WO 2007/004692 | 1/2007 | |
| WO | WO 2012/031744 | 3/2012 | |
| WO | WO 2012/079000 | 6/2012 | |
| WO | WO 2012/099441 | 7/2012 | |
| WO | WO 2013/034685 | 3/2013 | |
| WO | WO 2013/059593 | 4/2013 | |
| WO | WO 2015/031771 | 3/2015 | |
| WO | WO 2016/033488 | 3/2016 | |
| WO | WO 2017/151860 | 9/2017 | |
| WO | WO 2019/204269 | 10/2019 | |

OTHER PUBLICATIONS

"KYNU_Human," UniProt Submission Q16719, dated Jul. 24, 2013.
"kynureninase (EC 3.7.1.3)—human", GenBank accession No. G02652, 1999.
"kynureninase (L-kynurenine hydrolase) variant", GenBank: BAD97146.1, dated Apr. 26, 2005.
"SIDS2vsH1YAV1," UniProt 201609, dated Mar. 21, 2012.
Adams et al. "The kynurenine pathway in brain tumor pathogenesis." *Cancer Research* 72.22 (2012): 5649-5657.

(Continued)

*Primary Examiner* — Sean C. Barron
(74) *Attorney, Agent, or Firm* — pH IP Law

(57) ABSTRACT

Methods and compositions related to the use of a protein with kynureninase activity are described. For example, in certain aspects there may be disclosed a modified kynureninase capable of degrading kynurenine. Furthermore, certain aspects of the invention provide compositions and methods for the treatment of cancer with kynurenine depletion using the disclosed proteins or nucleic acids.

18 Claims, 10 Drawing Sheets

Specification includes a Sequence Listing.

(56) References Cited

OTHER PUBLICATIONS

Akash et al., "Development of therapeutic proteins: advances and challenges," *Tuk. J. Biol.*, 39:343-358, 2015.

Alberati-Giani et al., "Isolation and expression of a cDNA clone encoding human kynureninase," *Eur J Biochem.*, 239: 460-468, 1996.

Aznar et al., "Intratumoral delivery of immunotherapy—Act Locally, Think Globally," *J. Immunol.*, 198:31-39, 2017.

Baghban et al., "Tumor microenvironment complexity and therapeutic implications at a glance," *Cell Communication and Signaling*, 18:1-19, 2020.

Chen and Guillemin, "Kynurenine pathway metabolites in humans: disease and healthy states," *Int. J. Tryptophan Res.*, 2:1-19, 2009.

Curran et al., "PD-1 and CTLA-4 combination blockade expands infiltrating T cells and reduces regulatory T and myeloid cells within B16 melanoma tumors," *Proc. Natl. Acad. Sci. U S A*, 107:4275-4280, 2010.

De Jong et al., "Serum tryptophan and kynurenine concentrations as parameters for indoleamine 2,3-dioxygenase activity in patients with endometrial, ovarian, and vulvar cancer," *Int. J. Gynecol. Cancer*, 21(7):1320-1327, 2011.

Della Chiesa et al., "The tryptophan catabolite L-kynurenine inhibits the surface expression of NKp46-and NKG2D-activating receptors and regulates NK-cell function," *Blood*, 108(13):4118-4125, 2006.

Disis et al., "Use of tumor-responsive T cells as cancer treatment", *Lancet*, 373:673-683, 2009.

Duval et al., "Adoptive transfer of allogenic cytotoxic T lymphocytes equipped with a HLA-A2 restricted MART-1 T-cell receptor: a phase I trial in metastatic melanoma", *Clin. Cancer Res.*, 12:1229-1236, 2006.

Extended European Search Report issued in corresponding European Application No. 18204264, mailed on Apr. 25, 2019.

Extended European Search Report issued in European Application No. 17760774.4, mailed on Jul. 22, 2019.

Extended European Search Report issued in European Patent Application No. 14840339.7, dated Mar. 28, 2017.

Gailani et al., "Studies on tryptophan metabolism in patients with bladder cancer," *Cancer Research.*, 33: 1071-1077, 1973.

Godin-Ethier et al., "Indoleamine 2, 3-Dioxygenase Expression in Human Cancers: Clinical and Immunologic Perspectives," *Clinical Cancer Research*, 17(22):6985-6991, 2011.

Holmgaard et al., "Indoleamine 2, 3-dioxygenase is a critical resistance mechanism in antitumor T cell immunotherapy targeting CTLA-4," *The Journal of Experimental Medicine*, 210:1389-1402, 2013.

Hoyos et al., "Genetic modification of human T lymphocytes for the treatment of hematologic malignancies," *Haematologica.*, 97(11): 1622-31, 2012.

International Preliminary Report on Patentability issued in corresponding PCT Application No. PCT/US2014/05343, mailed on Mar. 10, 2016.

International Preliminary Report on Patentability issued in International Application No. PCT/US2015/047475, mailed Mar. 9, 2017.

International Search Report and Written Opinion issued in International Application No. PCT/US2014/053437, mailed Mar. 10, 2015.

International Search Report and Written Opinion issued in International Application No. PCT/US2015/047475, mailed Feb. 2, 2016.

International Search Report and Written Opinion issued in PCT Application No. PCT/US2019/027623, mailed on Aug. 22, 2019.

Kaper et al., "Nanosensor detection of an immunoregulatory tryptophan influx/kynurenine efflux cycle," *PLoS Biology*, 5(10):e257, 2007.

KR 10-2012-0085209, Machine Translation from Korean Intellectual Property Office, downloaded on Jun. 25, 2021, from http://engpat.kipris.or.kr/pmt/patent/patentRTT.jsp.

Lima et al., "Crystal Structure of *Homo sapiens* Kynureninase," *Biochemistry*, 46(10):2735-2744, 2007.

Lima et al., "Crystal structure of the *Homo sapiens* kynureninase-3-hydroxyhippuric acid inhibitor complex: insights into the molecular basis of kynureninase substrate specificity," *J. Med. Chem.*, 52(2): 389-396, 2009.

Lipowska-Bhalla et al., "Targeted immunotherapy of cancer with Car T cells: achievements and challenges," *Cancer Immunology Immunotherapy*, 61(7):953-962, 2012.

Lob et al., "Inhibitors of indoleamine-2,3-dioxygenase for cancer therapy: can we see the wood for the trees?" *Nat. Rev. Cancer*, 9(6):445-452, 2009.

Mandi and Vecsei, "The kynurenine system and immunoregulation," *J. Neural Transm.*, 119(2):197-209, 2012.

Marabelle et al., "Intratumoral immunotherapy: using the tumor as the remedy," *Annals of Oncology*, 28:xii33-xii43, 2017.

Mezrich et al., "An interaction between kynurenine and the aryl hydrocarbon receptor can generate regulatory T cells," *The Journal of Immunology*, 185(6):3190-3198, 2010.

Office Communication issued in Canadian Application No. 2,922,670, mailed May 26, 2021.

Office Communication issued in Chinese Application No. 201480053899.1, mailed Feb. 15, 2019. (English Translation).

Office Communication issued in corresponding Japanese Application No. 2016-537898, mailed Sep. 20, 2017. (English Translation).

Office Communication issued in Japanese Application No. 2017-511675, mailed Jun. 27, 2019. (English Translation).

Office Communication issued in Japanese Application No. 2018-042760, mailed Jan. 16, 2019. (English Translation).

Office Communication issued in Japanese Application No. 2020-073212, mailed May 19, 2021. (English Translation).

Office Communication issued in Korean Application No. 10-2021-7019661, mailed on Aug. 11, 2021. English Translation.

Office Communication issued in New Zealand Patent Application No. 717492, mailed May 26, 2021.

Office Communication issued in U.S. Appl. No. 14/839,293, dated Jan. 6, 2017.

Office Communication issued in U.S. Appl. No. 15/351,060, dated Dec. 12, 2016.

Office Communication Issued in U.S. Appl. No. 14/473,040, mailed Nov. 23, 2016.

Office Communication issued in U.S. Appl. No. 14/839,293, dated Oct. 19, 2017.

Office Communication issued in U.S. Appl. No. 14/839,293, dated Apr. 14, 2017.

Office Communication issued in U.S. Appl. No. 15/961,968, dated Jan. 1, 2021.

Office Communication issued in U.S. Appl. No. 14/473,040, dated Jul. 3, 2017.

Office Communication issued in U.S. Appl. No. 14/473,040, dated Jul. 6, 2016.

Office Communication issued in U.S. Appl. No. 15/351,060, dated Mar. 9, 2018.

Office Communication issued in U.S. Appl. No. 15/351,060, dated Jun. 26, 2017.

Opitz et al., "An endogenous tumour-promoting ligand of the human aryl hydrocarbon receptor," *Nature*, 478(7368):197-203, 2011.

Opitz et al., "The Indoleamine-2, 3-Dioxygenase (IDO) Inhibitor 1-Methyl-D-tryptophan Upregulates IDO1 in Human Cancer Cells," *PLoS One*, 6(5):e19823, 2011.

Phillips, "Structure and mechanism of kynurinase", *Arch. Biochem. Biophys.*, 544:69-74, 2014.

Phillips, "Structure, mechanism, and substrate specificity of kynureninase", *Biochimica et Biophysica Acta*, 1814: 1481-1488, 2011.

Pilotte et al., "Reversal of tumoral immune resistance by inhibition of tryptophan 2,3-dioxygenase," *Proc. Natl. Acad. Sci. U S A*, 109(7):2497-2502, 2012.

Platten et al., "Cancer Immunotherapy by Targeting IDO1/TDO and Their Downstream Effect", *Front. Immunol.*, 5:673, 2015.

Prendergast, "Cancer: Why tumours eat tryptophan," *Nature*, 478(7368):192-194, 2011.

Rabinkov et al., "Alliinase: structural peculiarities and applying for targeted therapy: SW02. W10-4", *FEBS J.*, 280.1, 2013.

(56) References Cited

OTHER PUBLICATIONS

Response filed in U.S. Appl. No. 14/839,293, dated Mar. 6, 2017.

Rutella et al., "Targeting indoleamine 2,3-dioxygenase (IDO) to counteract tumour-induced immune dysfunction: from biochemistry to clinical development," *Endocr. Metab. Immune Disord. Drug Targets*, 9(2):151-177, 2009.

Schottler et al., "Protein engineering of the restriction endonuclease EcoRV—structure-guided design of enzyme variants that recognize the base pairs flanking the recognition site," *Eur. J. Biochem.*, 258(1): 184-91, 1998.

Shanks et al., "Are animal models predictive for humans?" *Philosophy, Ethics, and Humanities in Medicine*, 4:2, 2009.

Shin et al., "Modulation of natural killer cell antitumor activity by the aryl hydrocarbon receptor," *Proc. Natl. Acad. Sci. U S A*, 110(30):12391-12396, 2013.

Simpson et al., "Fc-dependent depletion of tumor-infiltrating regulatory T cells co-defines the efficacy of anti-CTLA-4 therapy against melanoma," *J. Exp. Med.*, 210(9): 1695-1710, 2013.

Singh et al., "Protein Engineering Approaches in the Post-Genomic Era," Current Protein and Peptide Science, 18:1-11, 2017.

Song et al., "L-Kynurenine-induced apoptosis in human NK cells is mediated by reactive oxygen species," *International Immunopharmacology*, 11(8):932-938, 2011.

Stone et al., "Abstract LB-226: Depletion of kynurenine using an engineered therapeutic enzyme potently inhibits cancer immune checkpoints both as a monotherapy and in combination with anti-PD-1," Proceedings of the AACR 106th Annual Meeting, Philadelphia, PA, Apr. 18-22, 2015, Cancer Research, 75(15 Supplement):LB-226-LB-226, Aug. 2015.

Sudradhar et al. "Distribution and elimination of protein therapeutics: A review," *S. J. Pharm. Sci.*, 4:1-12, 2011.

Supplementary European Search Report issued in European Patent Application No. 15834988.6, dated Jan. 16, 2018.

Toma et al., "Cloning and recombinant expression of rat and human kynureninase," *FEBS Letters.*, 408(1): 5-10, 1997.

Triplett et al., "Reversal of IDO-mediated cancer immune suppression by systemic kynurenine depletion with a therapeutic enzyme," *Nat. Biotechnol.*, 36:758-764, 2018.

UniProt_201609 Acc#H1YAV1 Lucas et al., Mar. 21, 2012. Alignment with SEQ ID No. 33.

Veronese et al., "Peptide and protein PEGylation: a review of problems and solutions," *Biomaterials*, 22(5): 405-417, 2001.

Walsh et al., "Purification and biochemical characterization of some of the properties of recombinant human kynurinase", *Eur. J. Biochem.*, 269:2069-2074, 2002.

Yao et al., "Serum metabolic profiling and features of papillary thyroid carcinoma and nodular goiter," *Mol. Biosyst.*, 7(9):2608-2614, 2011.

Yoshikawa et al., "Serum concentration of L-kynurenine predicts the clinical outcome of patients with diffuse large B-cell lymphoma treated with R-CHOP," *Eur. J. Haematol.*, 84(4):304-309, 2010.

Zhang et al., "Propagated Perturbations from a Peripheral Mutation Show Interactions Supporting WW Domain Thermostability," Structure, 26:1474-1485, 2018.

* cited by examiner

SEQUENCE LISTING

```
Sequence total quantity: 57
SEQ ID NO: 1           moltype = DNA  length = 1347
FEATURE                Location/Qualifiers
misc_feature           1..1347
                       note = Synthetic polynucleotide
source                 1..1347
                       mol_type = other DNA
                       organism = synthetic construct
SEQUENCE: 1
tctagaaata attttgttta actttaagga aaacattaaa ataaggaggt agcaaatggg   60
cggtcatcat caccaccatc atgggagcgg caccacccgc aacgattgcc tggcgctgga  120
tgcgcaggat agcctggcac cgctgcgtca gcagtttgcg ctgccggaag gtgttattta  180
tctggatggc aacagcctgg gtgcgcgtcc ggttgcggcg ctggcgcgtg cgcaggcggt  240
gattgcggaa gaatggggca acggcctgat tcgcagctgg aacagcgcgg gctggcgcga  300
tctgagcgaa cgcctgggca accgcctggc gaccctgatt ggcgcgcgcg atggcgaagt  360
ggtggtgacc gataccacca gcattaacct gtttaaagtg ctgagcgcgg cgctgcgcgt  420
gcaggcgacc cgcagcccgg aacgccgcgt gattgtgacc gaaaccagca actttccgac  480
cgatctgtat attgcggaag gcctggcgga tatgctgcag cagggctata ccctgcgcct  540
ggtggatagc ccggaagaac tgccgcaggc gattgatcag gataccgcgg tggtgatgct  600
gacccatgtg aactataaaa ccggctatat gcatgatatg caggcgctga ccgcgctgag  660
ccatgaatgc ggcgcgctgg cgatttggga tctggcgcat agcgcgggcg cggtgccggt  720
ggatctgcat caggcgggcg cggattatgc gattggctgc acctataaat atctgaacgg  780
cggcccgggc agccaggcgt ttgtgtgggt gagcccgcag ctgtgcgatc tggtgccgca  840
gccgctgtct ggttggtttg gccatagccg ccagtttgcg atggaaccgc gctatgaacc  900
gagcaacggc attgcgcgct atctgtgcgg cacccagccg attaccagcc tggcgatggt  960
ggaatgcggc ctggatgtgt ttgcgcagac cgatatggcg agcctgcgcc gcaaaagcct 1020
ggcgctgacc gatctgttta ttgaactggt ggaacagcgc tgcgcggcgc atgaactgac 1080
cctggtgacc ccgcgcgaac atgcgaaacg cggcagccat gtgagctttg aacatccgga 1140
aggctatgcg gtgattcagg cgctgattga tcgcggcgtg attggcgatt atcgcgaacc 1200
gcgcattatg cgctttggct ttacccccgct gtataccacc tttaccgaag tgtgggatgc 1260
ggtgcagatt ctgggcgaaa ttctggatcg caaaacctgg gcgcaggcgc agtttcaggt 1320
gcgccatagc gtgacctagt aggatcc                                    1347

SEQ ID NO: 2           moltype = DNA  length = 1497
FEATURE                Location/Qualifiers
misc_feature           1..1497
                       note = Synthetic polynucleotide
source                 1..1497
                       mol_type = other DNA
                       organism = synthetic construct
```

-continued

```
SEQUENCE: 2
tctagaaata attttgttta actttaagga caaatcagga cacagttaag gaggtaaaat    60
atgggcggtc atcatcacca ccatcatggg agcggcgaac cgagctccct tgaacttccg   120
gccgataccg tgcaacggat agcggcgaac ttgaaatgtc acccgaccga cgaacgcgtc   180
gcgttacatc tggatgagga agacaagctg cgtcacttcc gcgagtgctt ttacattccg   240
aaaattcagg atctgccgcc agtggacttg agcctggtca acaaagacga gaacgccatc   300
tacttcctgg gcaatagcct gggcctgcaa ccaaagatgg tgaaaaccta tcttgaggag   360
gagcttgaca aatgggcgaa gatcgcggcc tacggccatg aagtcggcaa gcgtccctgg   420
attaccggcg atgagtcaat cgttggcttg atgaaggata tcgtcggcgc gaacgagaaa   480
gaaattgcgc tgatgaacgc gctgaccgtg aatctgcatc tgctgatgct gtcattcttt   540
aagcccaccc cgaagcgcta caaaatcctg ctggaagcga aagcgtttcc cagcgatcat   600
tatgcgatag aaagccagct gcaactgcac ggcctgaata tcgaggagag catgcgtatg   660
ataaaaccgc gcgaaggtga ggagaccctg cggattgagg acatcctgga ggtgatcgag   720
aaggagggcg acagtatcgc ggtgatactt ttcagcggcg tgcatttcta cacgggccaa   780
cacttcaata tcccggccat taccaaagcc ggccaggcga aagggtgcta tgtaggcttt   840
gatctggcgc atgcagtggg caacgtcgaa ctgtatcttc atgattgggg cgttgatttt   900
gcgtgctggt gcagctataa gtatctgaat gccggggccg tgggattgc gggagccttt   960
attcatgaga aacacgcgca taccattaaa ccggcgctgg ttggctggtt tgggcacgaa  1020
ctgagcaccc gcttcaagat ggataacaaa ctgcaattga ttccgggcgt gtgcggcttt  1080
cgtattagca accccccgat tctgctggtc tgcagcctgc acgcgtctct ggagattttc  1140
aagcaggcga ccatgaaagc gctgcgtaag aaaagtgtgc ttctgacggg ctacctggag  1200
tacctgataa agcacaacta cggcaaggat aaggcggcca cgaagaagcc ggttgtgaac  1260
attatcaccc cgtctcatgt ggaagaacgt ggctgccaac tgacgataac gttcagcgtg  1320
ccaaacaagg acgtgttcca agagctggag aagcgtggcg tggtgtgtga taaacgtaat  1380
ccgaatggca ttcgtgtggc gcctgtgccg ctgtacaaca gcttccacga cgtgtataag  1440
ttcaccaacc tgctgacgag cattctggac agtgcgaaa ccaaaaacta gggatcc      1497

SEQ ID NO: 3          moltype = DNA  length = 1492
FEATURE               Location/Qualifiers
misc_feature         1..1492
                      note = Synthetic polynucleotide
source               1..1492
                      mol_type = other DNA
                      organism = synthetic construct
SEQUENCE: 3
tctagaaata attttgttta actttaagaa cacggtcggg aatataagga ggtaaaatat    60
gggcggtcat catcaccacc atcatgggag cggcgagccg agcccgctgg aactgccggt   120
tgacgcggta cgtcgtattg cggcagaact gaactgtgac ccgaccgatg aacgtgtggc   180
gctgcgtctc gacgaagagg acaagctctc tcacttccgt aactgcttct atatccctaa   240
aatgcgtgac ctgccgagca tcgatctgtc tctggtttct gaagacgacg acgcgattta   300
cttcctgggt aactctctgg gtctgcagcc aaaaatggtt cgtacctacc tggaggaaga   360
gctggacaaa tgggcgaaaa tgggtgccta cggccatgt gtgggcaaac gcccgtggat   420
cgtcggcgac gaaagcattg tgtctctcat gaaggacatt gttggtgcac acagagaaga   480
aattgcgctg atgaatgctc tgaccatcaa cctgcacctg ctgctcctgt ctttcttcaa   540
gccgaccccg aagcgtcata aaatcctgct cgaggctaaa gcgttcccgt ctgatcacta   600
cgcgatcgaa tctcaaatcc aactgcacg tctggacgtt gagaagtcta tgcgtatggt   660
taagccgcgt gaaggcgagg agaccctccg tatggaagac atcctcgaag ttatcgaaga   720
agaaggtgac tctatcgcag ttattctgtt ctctggcctg cactttaca ccggtcaact   780
gttcaatatc ccggcaatca ccaaagcggg ccacgcgaaa ggttgcttcg ttggtttcga   840
cctggcccat gcggttggta acgtggagct gcgcctccac gactggggtg ttgactttgc   900
gtgctggtgc tcttacaaat acctgaactc tggtgcgggt ggtctcgcgg gtgcgtttat   960
ccacgaaaaa cacgcgcaca ccgttaaacc ggcgctggtt ggctggttcg gccacgacct  1020
ctctacgcgt ttcaacatgg acaacaaact ccagctgatc ccaggcgcca acggtttccg  1080
tatctctaac ccgccgatcc tcctggtttg ctctctgcac gcgtctctcg aggttttcca  1140
gcaggcgacc atgaccgccc tgcgccgtaa atctattctc ctgacgggt atctggaata  1200
catgctgaag cactaccact ctaaagacaa cacggaaaac aaaggtccga tcgttaacat  1260
catcaccccg tctcgtgcgg aagaacgtgg ctgccaactg accctgacct ctctctattcc  1320
gaaaaaatct gttttcaaag aactggaaa acgtggtgtt gtttgcgaca aacgtgaacc  1380
ggacggtatc gcgttgctc cggtcccgct gtacaactct ttccatgacg tttataagtt  1440
cattcgtctg ctcacctcca tcctggactc tagcgaacgc tcctaaggat cc          1492

SEQ ID NO: 4          moltype = DNA  length = 1251
FEATURE               Location/Qualifiers
source               1..1251
                      mol_type = other DNA
                      organism = Pseudomonas fluorescens
SEQUENCE: 4
atgaccaccc gcaacgattg cctggcgctg gatgcgcagg atagcctggc accgctgcgt    60
cagcagtttg cgctgccgga aggtgttatt tatctggatg gcaacagcct gggtgcgcgt   120
ccggttgcgg cgctgcgcg tgcgcaggcg gtgattgcgg aagaatgggg caacggcctg   180
attcgcagct ggaacagcgc gggctggcgc gatctgagcg aacgcctggg caaccgcctg   240
gcgaccctga ttggcgcgcg cgatggcgaa gtggtggtga ccgataccac cagcattaac   300
ctgtttaaag tgctgagcgc ggcgctgcgc gtgcaggcga cccgcagccc ggaacgccgc   360
gtgattgtga ccgaaaccag caacttccg accgatctgt atattgcgga aggcctggcg   420
gatatgctgc agcaggcgct ataccctgcgc ctggtggata gcccggaaga actgccgcag   480
gcgattgatc aggataccgc ggtggtgatg ctgacccatg tgaactataa aaccggctat   540
atgcatgata tgcaggcgct gaccgcgctg agccatgaat cggcgcgct ggcgatttgg   600
gatctggcgc atagcgcggg cgcggtgccg gtggatctgc atcaggcggg cgcggattat   660
gcgattggct gcacctataa atatctgaac ggcggccgg gcagccaggc gtttgtgtgg   720
```

```
gtgagcccgc agctgtgcga tctggtgccg cagccgctgt ctggttggtt tggccatagc   780
cgccagtttg cgatggaacc gcgctatgaa ccgagcaacg gcattgcgcg ctatctgtgc   840
ggcacccagc cgattaccag cctggcgatg gtggaatgcg gcctggatgt gtttgcgcag   900
accgatatgg cgagcctgcg ccgcaaaagc ctggcgctga ccgatctgtt tattgaactg   960
gtggaacagc gctgcgcggc gcatgaactg accctggtga ccccgcgcga acatgcgaaa  1020
cgcggcagcc atgtgagctt gaacatccg gaaggctatg cggtgattca ggcgctgatt   1080
gatcgcggcg tgattggcga ttatcgcgaa ccgcgcatta tgcgctttgg ctttaccccg  1140
ctgtatacca cctttaccga agtgtgggat gcggtgcaga ttctgggcga aattctggat  1200
cgcaaaacct gggcgcaggc gcagtttcag gtgcgccata gcgtgaccta g           1251

SEQ ID NO: 5            moltype = DNA   length = 1398
FEATURE                 Location/Qualifiers
source                  1..1398
                        mol_type = other DNA
                        organism = Homo sapiens SEQUENCE: 5
atggaaccga gctcccttga acttccggcc gataccgtgc aacggatagc ggcggaattg   60
aaatgtcacc cgaccgacga acgcgtcgcg ttacatctgg atgaggaaga caagctgcgt  120
cacttccgcg agtgctttta cattccgaaa attcaggatc tgccgccagt ggacttgagc  180
ctggtcaaca aagacgagaa cgccatctac ttcctgggca atagcctggg cctgcaacca  240
aagatggtga aaacctatct tgaggaggag cttgacaaat gggcgaagat cgcggcctac  300
ggccatgaag tcggcaagcg tccctggatt accggcagcg agtcaatcgt tggcttgatg  360
aaggatatcg tcggcgcgaa cgagaaagaa attgcgctga tgaacgcgct gaccgtgaat  420
ctgcatctgc tgatgctgtc attctttaag cccacccga agcgctacaa aatcctgctg   480
gaagcgaaag cgtttcccag cgatcattat gcgatagaa gccagctgca actgcacggc   540
ctgaatatcg aggagagcat gcgtatgata aaaccgcgcg aaggtgagga gaccctgcgg  600
attgaggaca tcctggaggt gatcgagaag gagggcgaca gtatcgcggt gatactttc   660
agcggcgtgc atttctacac gggccaacac ttcaatatcc cggccattac caaagccggc  720
caggcgaaag ggtgctatgt aggctttgat ctggcgcatg cagtgggcaa cgtcgaactg  780
tatcttcatg attggggcgt tgattttgcg tgctggtgca gctataagta tctgaatgcc  840
ggggccggtg ggattgcggg agcctttatt catgagaaac acgcgcatac cattaaaccg  900
gcgctggttg gctggtttgg gcacgaactg agcacccgct tcaagatgga taacaaactg  960
caattgattc cgggcgtgtg cggctttcgt attagcaacc ccgattct gctggtctgc  1020
agcctgcacg cgtctctgga gattttcaag caggcgacca tgaaagcgct gcgtaagaaa  1080
agtgtgcttc tgacgggcta cctggagtac ctgataaagc acaactacgg caaggataag  1140
gcggccacga agaagccggt tgtgaacatt atcacccgt ctcatgtgga agaacgtggc  1200
tgccaactga cgataacgtt cagcgtgcca aacaaggacg tgttccaaga gctggagaag  1260
cgtggcgtgg tgtgtgataa acgtaatccg aatggcattc gtgtggcgcc tgtgccgctg  1320
tacaacagct ccacgacgt gtataagttc accaacctgc tgacgagcat tctggacagt  1380
gcggaaacca aaaactag                                                1398

SEQ ID NO: 6            moltype = DNA   length = 1395
FEATURE                 Location/Qualifiers
source                  1..1395
                        mol_type = other DNA
                        organism = Mus musculus SEQUENCE: 6
atggagccga gcccgctgga actgccggtt gacgcggtac gtcgtattgc ggcagaactg   60
aactgtgacc cgaccgatga acgtgtggcg ctgcgtctcg acgaagagga caagctctct  120
cacttccgta actgcttcta tatccctaaa atgcgtgacc tgccgagcat cgatctgtct  180
ctggtttctg aagacgacga cgcgatttac ttcctggta actctctggg tctgcagcca  240
aaaatggttc gtacctacct ggaggaagag ctggacaaat gggcgaaaat gggtgcctac  300
ggccatgatg tgggcaaacg cccgtggatc gtcggcgacg aaagcattgt gtctctcatg  360
aaggacattg ttggtgcaca cgagaaagaa attgcgctga tgaatgctct gaccatcaac  420
ctgcacctgc tgctcctgtc tttcttcaag ccgacccga agcgtcataa aatcctgctc  480
gaggctaaag cgttcccgtc tgatcactac gcgatcgaat ctcaaatcca actgcacggt  540
ctggacgttg agaagtctat gcgtatggtt aagccgcgtg aaggcgagga cccctccgt   600
atggaagaca tcctcgaagt tatcgaagaa gaaggtgact ctatcgcagt tattctgttc  660
tctggcctgc acttttacac cggtcaactg ttcaatatcc cggcaatcac caaagcgggc  720
cacgcgaaag gttgcttcgt tggtttcgac ctggcccatg cggttggtaa cgtggagctg  780
cgcctccacg actggggtgt tgactttgcg tgctggtgct cttacaaata cctgaactct  840
ggtgcgggtg gtctcgcggg tgcgttcgtc acgaaaaac acgcgcacac cgttaaaccg  900
gcgctggttg gctggttcgg ccacgacctc tctacgcgtt caacatgga caacaaactc  960
cagctgatcc caggcgccaa cggtttccgt atctctaacc ccgatcct cctggtttgc  1020
tctctgcacg cgtctctcga ggttttccag caggcgacca tgaccgccct gcgccgtaaa  1080
tctattctcc tgacgggtta tctggaatac atgctgaagc actaccactc taaagacaac  1140
acggaaaaca aaggtccgat cgttaacatc atcaccccgt ctcgtgcgga gaacgtggc   1200
tgccaactga ccctgacctt ctctattccg aaaaaatctg ttttcaaaga actggagaaa  1260
cgtggcgttg tttgcgacaa acgtgaaccg gacggtatcc gcgttgctcc ggtcccgctg  1320
tacaactctt ccatgacgt ttataagttc attcgtctgc tcacctccat cctggactct  1380
agcgaacgct cctaa                                                   1395

SEQ ID NO: 7            moltype = AA   length = 416
FEATURE                 Location/Qualifiers
source                  1..416
                        mol_type = protein
                        organism = Pseudomonas fluorescens SEQUENCE: 7
MTTRNDCLAL DAQDSLAPLR QQFALPEGVI YLDGNSLGAR PVAALARAQA VIAEEWGNGL   60
```

```
IRSWNSAGWR  DLSERLGNRL  ATLIGARDGE  VVVTDTTSIN  LFKVLSAALR  VQATRSPERR   120
VIVTETSNFP  TDLYIAEGLA  DMLQQGYTLR  LVDSPEELPQ  AIDQDTAVVM  LTHVNYKTGY   180
MHDMQALTAL  SHECGALAIW  DLAHSAGAVP  VDLHQAGADY  AIGCTYKYLN  GGPGSQAFVW   240
VSPQLCDLVP  QPLSGWFGHS  RQFAMEPRYE  PSNGIARYLC  GTQPITSLAM  VECGLDVFAQ   300
TDMASLRRKS  LALTDLFIEL  VEQRCAAHEL  TLVTPREHAK  RGSHVSFEHP  EGYAVIQALI   360
DRGVIGDYRE  PRIMRFGFTP  LYTTFTEVWD  AVQILGEILD  RKTWAQAQFQ  VRHSVT       416

SEQ ID NO: 8              moltype = AA  length = 465
FEATURE                   Location/Qualifiers
source                    1..465
                          mol_type = protein
                          organism = Homo sapiens
SEQUENCE: 8
MEPSSLELPA  DTVQRIAAEL  KCHPTDERVA  LHLDEEDKLR  HFRECFYIPK  IQDLPPVDLS   60
LVNKDENAIY  FLGNSLGLQP  KMVKTYLEEE  LDKWAKIAAY  GHEVGKRPWI  TGDESIVGLM   120
KDIVGANEKE  IALMNALTVN  LHLLMLSFFK  PTPKRYKILL  EAKAFPSDHY  AIESQLQLHG   180
LNIEESMRMI  KPREGEETLR  IEDILEVIEK  EGDSIAVILF  SGVHFYTGQH  FNIPAITKAG   240
QAKGCYVGFD  LAHAVGNVEL  YLHDWGVDFA  CWCSYKYLNA  GAGGIAGAFI  HEKHAHTIKP   300
ALVGWFGHEL  STRFKMDNKL  QLIPGVCGFR  ISNPPILLVC  SLHASLEIFK  QATMKALRKK   360
SVLLTGYLEY  LIKHNYGKDK  AATKKPVVNI  ITPSHVEERG  CQLTITFSVP  NKDVFQELEK   420
RGVVCDKRNP  NGIRVAPVPL  YNSFHDVYKF  TNLLTSILDS  AETKN                    465

SEQ ID NO: 9              moltype = AA  length = 464
FEATURE                   Location/Qualifiers
source                    1..464
                          mol_type = protein
                          organism = Mus musculus
SEQUENCE: 9
MEPSPLELPV  DAVRRIAAEL  NCDPTDERVA  LRLDEEDKLS  HFRNCFYIPK  MRDLPSIDLS   60
LVSEDDDAIY  FLGNSLGLQP  KMVRTYLEEE  LDKWAKMGAY  GHDVGKRPWI  VGDESIVSLM   120
KDIVGAHEKE  IALMNALTIN  LHLLLLSFFK  PTPKRHKILL  EAKAFPSDHY  AIESQIQLHG   180
LDVEKSMRMV  KPREGEETLR  MEDILEVIEE  EGDSIAVILF  SGLHFYTGQL  FNIPAITKAG   240
HAKGCFVGFD  LAHAVGNVEL  RLHDWGVDFA  CWCSYKYLNS  GAGGLAGAFV  HEKHAHTVKP   300
ALVGWFGHDL  STRFNMDNKL  QLIPGANGFR  ISNPPILLVC  SLHASLEVFQ  QATMTALRRK   360
SILLTGYLEY  MLKHYHSKDN  TENKGPIVNI  ITPSRAEERG  CQLTLTFSIP  KKSVFKELEK   420
RGVVCDKREP  DGIRVAPVPL  YNSFHDVYKF  IRLLTSILDS  SERS                     464

SEQ ID NO: 10             moltype = AA  length = 466
FEATURE                   Location/Qualifiers
source                    1..466
                          mol_type = protein
                          organism = Pongo abelii
SEQUENCE: 10
MEPSSLELPA  DTVQRIAAEL  KCHPTDERVA  LHLDEEDKLR  HFREYFYIPK  IRDLPPVDFI   60
ISESKDENAI  YFLGNSLGLQ  PKMVKTYLEE  ELDKWAKIAA  YGHEVGKRPW  ITGDESIVGL   120
MKDIVGANEK  EIALMNALTV  NLHLLMLSFF  KPTPKRYKIL  LEAKAFPSDH  YAIESQLQLH   180
GLNIEESMRM  VKPREGEETL  RTEDILEVIE  KEGDSIAVIL  FSGVHFYTGQ  HFNIPAITKA   240
GQAKGCYVGF  DLAHAVGNVE  LYLHDWGVDF  ACWCSYKYLN  AGAGGIAGAF  VHEKHAHTIK   300
PALVGWFGHE  LSTRFKMDNK  LQLIPGVCGF  RISNPPILLV  CSLHASLEIF  KQATMKALRK   360
KSILLTGYLE  YLIKHSYGKD  KAATKKPVVN  IITPSHIEER  GCQLTITFSV  PNKDVFQELE   420
KRGVVCDKRN  PNGIRVAPVP  LYNSFHDVYK  FTNLLTSILD  SAETTN                   466

SEQ ID NO: 11             moltype = AA  length = 465
FEATURE                   Location/Qualifiers
source                    1..465
                          mol_type = protein
                          organism = Macaca fascicularis
SEQUENCE: 11
MEPSPLELPA  DTVQRIATEL  KCHPTDERVA  LHLDEVDKLR  HFRECFYIPK  IQDLPPVDLS   60
LVNKDENAIY  FLGNSLGLQP  KMVKTYLEEE  LDKWAKIAAY  GHEVGKRPWI  TGDESIVGLM   120
KDIVGANEKE  IALMNALTVN  LHLLLLSFFK  PTPKRYKILL  EAKAFPSDHY  AIESQLQLHG   180
LNIEESMRMI  KPREGEETLR  IEDILEVIEK  EGDSIAVILF  SGVHFYTGQH  FNIPAITKAG   240
QAKGCYVGFD  LAHAVGNVEL  YLHDWGVDFA  CWCSYKYLNA  GAGGIAGAFI  HEKHAHTIKP   300
ALVGWFGHEL  STRFKMDNKL  QLIPGVCGFR  ISNPPILLVC  SLHASLEIFK  QATMKALRKK   360
SILLTGYLEY  LIKHKYGKDK  AATEKPIVNI  ITPSHIEERG  CQLTITFSVP  NKDVFQELEK   420
RGVVCDKRNP  NGIRVAPVPL  YNSFHDVYKF  TNLLTSILDS  AETTN                    465

SEQ ID NO: 12             moltype = AA  length = 465
FEATURE                   Location/Qualifiers
source                    1..465
                          mol_type = protein
                          organism = Pan troglodytes
SEQUENCE: 12
MEPSSVELPA  DTVQRIAAEL  KCHPTDERVA  LHLDEEDKLR  HFRECFYIPK  IQDLPPVDLS   60
LVNKDENAIY  FLGNSLGLQP  KMVKTYLEEE  LDKWAKIAAY  GHEVGKRPWI  TGDESIVGLM   120
KDIVGANEKE  IALMNALTVN  LHLLMLSFFK  PTPKRYKILL  EAKAFPSDHY  AIESQLQLHG   180
LNIEESMRMI  KPREGEETLR  IEDILEVIEK  EGDSIAVILF  SGVHFYTGQH  FNIPAITKAG   240
QAKGCYVGFD  LAHAVGNVEL  YLHDWGVDFA  CWCSYKYLNA  GAGGIAGAFI  HEKHAHTIKP   300
ALVGWFGHEL  STRFKMDNKL  QLIPGVCGFR  ISNPPILLVC  SLHASLEIFK  QATMKALRKK   360
```

-continued

```
SVLLTGYLEY LIKHNYGKDK AATKKPVVNI ITPSHVEERG CQLTITFSVP NKDVFQELEK    420
RGVVCDKRNP NGIRVAPVPL YNSFHDVYKF TNLLTSILDS AETTN                    465

SEQ ID NO: 13              moltype = AA  length = 431
FEATURE                    Location/Qualifiers
source                     1..431
                           mol_type = protein
                           organism = unidentified
SEQUENCE: 13
MLETENIRTL SDYKLGLDYA LDQDRKDELK SYRNQFHIPK DKQGDAWIYM TGNSLGLQPK    60
QTKAYVNQEL NDWANLGVEG HFEAKNPWLA YHEFLTESMA KVVGAKPIEV VVMNTLTANL    120
HFMMVSFYKP TKTRYKILIE SDAFPSDKYA VESQLRHHGF DDKEGVVLWK PRPGEELLNY    180
DDLETILETQ GDEIALIMIG GVNYYTGQYF DLKRITQLGH KQGCNVGFDC AHGAGNVALN    240
LHDSGADFAV WCTYKYLNSG PGSLAGCFVH ERHAYRKDLN RFTGWWSHNK QTRFNMRGEF    300
DQLPGAEGWQ LSNPPILSMA AIKASLDLFN EVGMDKLINK SKKLTGYFEY LLKQLGEDTI    360
RIITPKRSEE RGCQLSIQVK NADKSLHNKL TEVGIISDWR EPDVIRCAPV PLYNSFEDVY    420
RLVEKLKGIL K                                                        431

SEQ ID NO: 14              moltype = AA  length = 429
FEATURE                    Location/Qualifiers
source                     1..429
                           mol_type = protein
                           organism = unidentified
SEQUENCE: 14
MSNQINFEYS LDFAQKMDEK DPLKSFRSKF FFPKVEDKEA IYFCGNSLGL QPKTTQNYIQ    60
KELSNWAEMA VDGHFHGEDA WYHIRKKSKP ALAEIVGAHE HEVVAMNNLT SNLHFLMVSF    120
YRPNAKRFKI ITEAGAFPSD MYMLETQVKF HGLDPNKAIV ELAPRDGEHT LRTEDILQSI    180
KEQGEELALV MMAGLQYYTG QVFDMKAIAQ AVKDEGAFVG FDLAHAAGNV PLALHDWGVD    240
FATWCSYKYM NSGPGNVSGI FVHENHAEKP DMIRFAGWWG HDEGERFKME KGFKPMFGAD    300
GWQLANSNVL ALAAHQASLD IFQQAGIKTL REKSETLTSY LEFLIQKISG NSGVLEIITP    360
KNINERGCQL SLLVHKGGKA VFDEFYKNGI VGDWRNPNVI RIAPTPLYNS YEDVFRFAKI    420
LEQSLQKFA                                                           429

SEQ ID NO: 15              moltype = AA  length = 422
FEATURE                    Location/Qualifiers
source                     1..422
                           mol_type = protein
                           organism = Bizionia argentinensis
SEQUENCE: 15
MSNFKTGIDF AKEQDENDTL SCYRNQFHIP KDKQGNDMIY LCGNSLGLQP KATKDYINQE    60
LEDWANLGVE GHTHAKNPWL GYHEFLTDSM AKVVGAKPIE VVVMNTLTAN LHFMMVSFYK    120
PTIERYKIII EADAFPSDKY AVESQLRHHG YDDKEGLLLW KAREGEELLR YEDLEAILKE    180
HGDDVALVMI GGVNYYTGQF FDLKRITELG HKHGCMVGFD CAHGAGNVEL NLHDSGADFA    240
VWCTYKYLNS GPGSLGGCFV HERHAHNKRL NRFTGWWSHN KETRFKMRDE FDAIPGAEGW    300
QLSNPPILSM AAIKASLDIF EEIGMKKLNE KSRALTAYFE FLLKQVGDDS IRIITPENPD    360
ERGCQLSIQV KNADRSLHDK LTDAGVISDW REPDVIRCAP IPLYNSYQDV YHMVERLKNI    420
LE                                                                  422

SEQ ID NO: 16              moltype = AA  length = 431
FEATURE                    Location/Qualifiers
source                     1..431
                           mol_type = protein
                           organism = unidentified
SEQUENCE: 16
MTAFHAHFQP TREAALALDA SDELAPYRDQ FCLPQTQGQP VVYLCGHSLG LQPKTVREYI    60
DEELQDWAAL GVEGHFHARR PWLSYHEILT AQTARLAGAK PAEVVVMNSL TVNMHLMLVS    120
FYRPTPERFK ILIEADAFPS DRYAAESHLR WHGYDPQDAL LTLQPRPGEA AVRQEDIAAF    180
LHREGETIAL VWLGGVNYYT GQVFDMAEIT AIGHAQGCVV GFDLAHAAGN IILQLHDWDV    240
DCAVWCSYKY LNAGPGAAAG CFVHERYAQR PDLPRLAGWW GHNKDTRFQM PAGFDPIPGA    300
EGWQISNPPI FQLAALKASM DIFDRAGMMR LRAKSERLTG YLEYLLRDRA LPGVSLITPD    360
DPAQRGAQLS LQIKQHGCAL HQRLAEAHII CDWREPDVIR VAPVPLYNTF LDVLTFVNAL    420
DTAHREVLVS S                                                        431

SEQ ID NO: 17              moltype = AA  length = 424
FEATURE                    Location/Qualifiers
source                     1..424
                           mol_type = protein
                           organism = unidentified
SEQUENCE: 17
MAAAAFDTTE NFAIEMDARD PMSRFRGRFH IPPAPDGSAS VYLVGHSLGL QPKTVRAYLE    60
QELKDWETLG VEGHFRGKHP WMPYHRLLTE QTARLVCAQP SEVVVMNSLT VNLHLMMVSF    120
YRPTRERHNI LIEGSAFPSD QYAVQSQIKF HGFDPASSLL ELCPRVGEAT MRDEDILELI    180
EREGQSIALI LLGGVNYATG QAFDMAEITK AGHAQGCVVA FDCAHAAGNL ELKLHEWDVD    240
WAAWCSYKYL NGGPGCIGGC FVHERYARDF ELPRFAGWWG HDQETRFKMG PEFHPMAGAE    300
GWQLSNPSIL TMAALRASME IFDEAGIGKL RQRSIALTGY LEFLLDQQKS ARFEIITPRE    360
PERRGAQLSI RVAAGNRSVC DRLVEEGALC DWREPDILRV APVPLYCSYR DCYRFVQRFV    420
ANLN                                                                424

SEQ ID NO: 18              moltype = AA  length = 428
```

-continued

```
FEATURE                     Location/Qualifiers
source                      1..428
                            mol_type = protein
                            organism = unidentified
SEQUENCE: 18
MSNNQYEFSE SFARQMDVQD TLSGFRDRFY FPQINGKEAI YFCGNSLGLQ PKTVATYINK   60
ELDNWAKLGV DGHFYGEDAW YHVRKKSKPA LSAIVGAHEH EVVAMNNLTS NLHFLMVSFY  120
CPDQTRYKII TEAGAFPSDM YMLETQVKFH GLDPEKCIVE LSPRAGEYTL RTEDILMAIE  180
ANKENLALVM MAGLQYYTGQ VFDMKAITAA AHQVGARAGF DLAHAVGNAK LELHDWGVDF  240
ATWCSYKYLN SGPGNISGIF VHERHAENQE LPRFAGWWGH DEGERFRMEK GFKPMYGADG  300
WQLANSNVLA LAAHQASLDI FEEAGMDRLR AKSELLTGYL EFLIEKISGD SGVLEIITPK  360
IPNERGCQLS LLIHKGGKSV FDEFYKHGVV GDWRNPNVIR LAPTPLYNSF IDIYQFAKIL  420
EQSLQKFA                                                          428

SEQ ID NO: 19              moltype = AA   length = 421
FEATURE                    Location/Qualifiers
source                     1..421
                           mol_type = protein
                           organism = unidentified
SEQUENCE: 19
MIEKLKQYHD EAISLDSLDP LQKFKECFTL PKEPGALYFC SNSLGLPAKA ASQKLEEQLQ   60
RWSELGARGW FEGEGNWYNS LEESIVRPLS KILGAESNEV TLMNSLTVNL HMLLISFYRP  120
TKTRYKILID GPAFPSDLYA IKSHLRFHKK EEGLILIEPR PGEHLVQEED FLRVIKIQGE  180
EIALVFLNCV NFLSGQVLKV DEITRYAKEA GCCVGYDLAH AAGNIPLSLH DLGGDFAVGC  240
SYKYLCGGPG GPGIAYVHAS HHHQQFVRFS GWWGNDPNTR FYFPKEFVPY GGASSWQVST  300
PSILAKLPLI AALEVFEEAG MENIREKSKK QTAFLYTLLE NARGTHFDMI TPKEPELRGC  360
QLSLRIKCSR SEEILRKLER LGITCDFRSP NILRVTPSPL YTSFYEIYRF AYTFLEVLKT  420
I                                                                 421

SEQ ID NO: 20              moltype = AA   length = 425
FEATURE                    Location/Qualifiers
source                     1..425
                           mol_type = protein
                           organism = unidentified
SEQUENCE: 20
MNEILKHYQK KAAQLDEQDS LKHLRARFAL PKDPNAIYFC NNSLGLPAVG AFTKIEELLQ   60
RWSDVGVNGW FEGVGNWYRS FDNPLRQPLS KILGAEYEEV VVMNSLTMNL HLLLVSFYRP  120
TDTRYKILIE GPTFPSDLYA IKSQLSFHGK NPDDALIILE PRAGEDLLRY EDFQQTLEEQ  180
GESIALVFMN CVNFLTGQVL EVEAITNLAK EKGCVVGCDL AHAAGNIPLK LHEWGVDFAL  240
GCSYKYLCGG PGGPGIAFVH KSHHNEQLPR FSGWWGNDPE TRFQMQLQPE FIPYSGAYSW  300
QVSTPSIVSL MPLLATLEVF EEAGMERVRH KSKQMTAFLL ELLELAPPSC FEIITPRDPE  360
LRGSQLSIRI QQHSEEVLQK LEAQRITCDS RPPDIIRVTA TPLYNTFSEI YKFTCKLFEV  420
LEIKS                                                             425

SEQ ID NO: 21              moltype = AA   length = 425
FEATURE                    Location/Qualifiers
source                     1..425
                           mol_type = protein
                           organism = unidentified
SEQUENCE: 21
MTAPVYENTD VFAYGLDAAD PLRPLRDEFL FPPAPSGAPA IYLAGNSLGL QPRKARKYVQ   60
MEMEDWERLG VEGHVHGRHP WLPYHEQLTD MVARVVGAQP IEVVVMNTLS VNLHLMMVSF  120
YRPTRERFKI LIEGGAFPSD QYAVASQARF HGYDPKEAIV RLMPREGEDT LRSEDILEAI  180
ERHGKELALV MLGSVNYLTG QAFDLREITR VAHAQGCKVG FDLAHAAGNL KLSLHDDGPD  240
FAVWCSYKYL NGGPGSLGGV FVHERHAHSP QLPRFEGWWG HNKATRFEMG PTFDPLPGAE  300
GWQLSNPPIF QLAALRSSLE LFDKATMAAL RTKSDQLTGY LEFLLDRLPA GYVSITTPRD  360
LKQRGAQLSL RFKGEPKRLL QRLSAAGIIC DFREPDIIRA APTPLYNTYL DVFRFVKALE  420
AHALE                                                             425

SEQ ID NO: 22              moltype = AA   length = 426
FEATURE                    Location/Qualifiers
source                     1..426
                           mol_type = protein
                           organism = unidentified
SEQUENCE: 22
MDQIAFELTP EFARKMDLAD PLSTYREKFY IPEKNGQPLI YFCGNSLGLQ PRSVNAYLKQ   60
ELEKWADKGV DGHFEGKVPW IDARKPSKRL IAPLVGANEQ EVVAMNSLSV NLHLLMVSFY  120
QPKGKKFKIL TEAGAFPSDQ YILESQVKFH GLLPDEAILE MAPRPNEHLL RTEDILQKIE  180
DHKDELALIM LSGLQYYTGQ LFDLEAISSA ANKQGITIGF DLAHAIGNVP LRLHDWGVDF  240
ATWCSYKYLN SGPGNVSGIF VHEKHSDNAL LPRFAGWWGH DEKERFKMKK GFKHMPGADG  300
WLLSNDNVLG LAAHQASLEL FAEAGLDKLR KKSIQLTNYL EFAIHETIKD SELLEIITPL  360
KPTERGCQLS LLIHKGGKEV FDYWIDNGVV ADWRNPNVIR LAPTPMYNTF QDVFEFSRIL  420
KNSLEA                                                            426

SEQ ID NO: 23              moltype = AA   length = 426
FEATURE                    Location/Qualifiers
source                     1..426
                           mol_type = protein
                           organism = Cystobacter fuscus
```

```
SEQUENCE: 23
MSGEAVRFEP GEAFARRMDA EDPLRSFREE FLFPVHGDGH ELYLLGNSLG LQPRKAKEYV    60
LAAMEDWARL GVDGHFKGSP PWMEFHVGLG EQMARVVGAR PEEVVVMNTL TVNLHLMMVS   120
FYRPTPERSK ILMEASAFPS DQYAVAAQVR HHGYSPEQTV IPLAPRPGEH TLRHEDILDT   180
LERHGKEIAL VLLGNVNYLT GQAFDMAAIT RAAHQRGCRV GFDLAHAAGN LRLSLHEDGP   240
DFAVWCTYKY LNGGPGALGG VFIHERHLRD ASLHRLPGWW GNDRGTRFQM KPDFEPAPGA   300
EGWVLSNPPI IQMAALRASL ELFDRATMPA LRAKSEKLTG YLEFLIDRLP EGFVHSLTPR   360
DPGQRGAHLS LRFTKDPQRM LETLRAEGIH CDFRYPDIIR AAPVPLYNSF LDVHRFVSVL   420
ERYARG                                                             426

SEQ ID NO: 24              moltype = AA  length = 426
FEATURE                    Location/Qualifiers
source                     1..426
                           mol_type = protein
                           organism = unidentified SEQUENCE: 24
MSSYRYSLAF AQERDREDPL RKFQSRFHFP KVNGEAAIYF CGNSLGLQPK AVREHLDRDL    60
ESWASKAVDG HFEGDAPWFS VHERSKAALA EIVGAKKHEV VAMGSLTTNL HALLVSFYQP   120
NGKRNKILTE AGAFPSDMYA LESQVKYHGL DPDEAIVEVG PRPGEHTIRT EDILQAISKH   180
QDELACVMMA GLQYYTGQVF DMKAIASAAH AVGATVGFDL AHAAGNAPLH LHDWGVDFAA   240
WCSYKYLNSG PGNVAGIFVH ERHGNNPALN RFAGWWGHDE KVRFKMEKGF VPMYGADGWQ   300
NSNGNVLGMA AHQASLDIFQ EAGMVHLRKK SVQLTGFLAF LIREISGESG VLEVITPNAE   360
AERGCQLSLL IHKGGKAVFD EFYQNGIVGD WRNPNVIRIA PTPLYNSFED VFRFAKILEQ   420
SLSKFA                                                             426

SEQ ID NO: 25              moltype = AA  length = 420
FEATURE                    Location/Qualifiers
source                     1..420
                           mol_type = protein
                           organism = unidentified SEQUENCE: 25
MEFNTTRDYA LQLDQEDSLS RFRESFHIPK HTDGTDSIYL CGNSLGLQPR QTKTFLNQEL    60
DDWAKLGVEG HFHAENPWMP YHEFLTETTA QVVGAKPHEV VIMNTLTTNL HLMMVSFYQP   120
KGKRTKIIIE ADAFPSDRYA VASQVQFHGH DDKENIIEWA PRTGEHTPRL EDLETILKEQ   180
GDEIALIMVG AVNYYTGQFF DLKKITELGH AAGAMVGFDC AHGAGNVDLQ LHDSGADFAV   240
WCTYKYMNSG PGSLGGCFVH ERHANNSELP RFTGWWGHNK DTRFKMRDDF EPMHGAEGWQ   300
LSNPPILSMV AIRASLDLFA QAGFENLRKK SIQLTNYLEY LVGELDGDRI SIITPRDPKD   360
RGCQLSLAVK NADKSLFDAI TAKGVIADWR EPDVIRIAPV PLYNNYEDCW RFVDVLKSEL   420

SEQ ID NO: 26              moltype = AA  length = 442
FEATURE                    Location/Qualifiers
source                     1..442
                           mol_type = protein
                           organism = unidentified SEQUENCE: 26
MNFETTKNFA SQLDNNDSLA HFRDKFWIPT LNSISKNTNS SNEKGKEKVV YFCGNSLGLQ    60
PKTTKAYIEQ ELEDWKNLGV EGHFHGKNPW LSYHKLLTNQ TAKIVGAKPI EVVVMNNLTV   120
NLHLLMVSFY RPNQKRFKIL MEGGAFPSDQ YAIESQVKFH GFSPDDAIVE MMPRKNENSE   180
GEETLRTEDI LKKIEELGDE LALVMFGGVN YYTGQFFDLE KITQAAHKVG ATAGFDLAHA   240
AGNVPLKLHD WKVDFATWCS YKYLNSGAGG TSGVFINEKY ADDDSLPRFA GWWGHDEKDR   300
FKMKKGFIPM RGAEGWQLSN AQILPMAVHK ASLDIFEEAG FENLRQKSEQ LTVYMEFLIE   360
NFNKEQSKIK IKIITPKNKL ERGCQLSLVF DKEGKKYHET LTKRGVISDW REPNVIRIAP   420
IPLYNSFMDC YRFYEILKEI AV                                           442

SEQ ID NO: 27              moltype = AA  length = 423
FEATURE                    Location/Qualifiers
source                     1..423
                           mol_type = protein
                           organism = unidentified SEQUENCE: 27
MSNYKPGLDY AKEQDQNDAL SHYRSQFHIP KDNQGNNWLY FTGNSLGLQP KSTQKYIQQE    60
LDDWANLGVE GHFEAKNPWM PYHEFLTDSM AKIVGAKPIE VVTMNTLTTN LHLLMVSFYQ   120
PTKTKYKIVI ESDAFPSDRY AVQTQLEFHG FDANEGLIEW KPRQGEELLN LDDLETILEE   180
QGDEIALLLI GGVNYYTGQY LDLKKIAELG HAKNCMVGID LAHGAGNIKP ELHDSGVDFA   240
AWCTYKYLNS GPGSLGGLFV HEKHAHNKKL KRFAGWWSHN KATRFNMRQP LDVIPGAEGW   300
QLSNPPILSM AAIKASLDMF NEVGMDALRE KSEKLTGYFE FLLNELNNDK VKIITPSNPK   360
ERGCQLSIQV RDADKSLHKK LTKAHIITDW REPDVIRCAP VPLYNSFEDV YRMVDKLKQI   420
LNT                                                                423

SEQ ID NO: 28              moltype = AA  length = 429
FEATURE                    Location/Qualifiers
source                     1..429
                           mol_type = protein
                           organism = unidentified SEQUENCE: 28
MAKDILHMTY ENSLTFAQDL DRDDPLRHFR NKFHIPQLND KDVIYFTGNS LGLQPKNTRV    60
YIEEELEGWA TLGVDGHFHS QKRPWFYYHK FSKEALAKIV GAKPSEVVSM NNLTVNLHLM   120
MVSFYRPTSS RFKIMIEAGA FPSDQYAVES QIKFHGYNYE DALIEISPRE GEYHLRTEDI   180
LSKIEENKDS LALVLFGGVQ YYTGQLFDIG SITAAGHWAG AIVGFDLAHA AGNVPLNLHN   240
```

```
DQVDFAAWCS YKYLNSGPGG VSGIFVHEKH GDAELPRFAG WWGHNESERF KMKKGFIPMS  300
GADGWQLSNV NILSSAAHLA ALEIYDEAGM EALRQKSIRL TGFMEYLLNG FNLGDDVLKI  360
ITPTDPAARG CQLSLLVSKN GKAIFEHLTR SGVVADWREP DVIRVAPVPL YNTFEDVYNF  420
CEILKKVIF                                                         429

SEQ ID NO: 29              moltype = AA   length = 425
FEATURE                    Location/Qualifiers
source                     1..425
                           mol_type = protein
                           organism = Kangiella aquimarina
SEQUENCE: 29
MTDIFSIDYA RQLDQQDPIS RMREQFHIPK QDNGDDEIYL CGNSLGLQPK RTQEYLNYEL  60
SQWQKLGVKG HFSGDFPWMP YHEFLTEESA KLVGAKNSEV VCMNSLTANL HFMMVSFYRP  120
TATRNKILIE DHAFPSDHYA VESQVRYHGF DPDQAMLLAK PREGEETLRT EDLLNLIELH  180
GEEIALIMLP GVQYYTGQVL DMKAITQAGH AKGCKVGFDL AHATGNIPMH LHDWDVDFAA  240
WCSYKYLNSG PGSVAGCFVH EKHHTNMELP RFAGWWGHDK DSRFKMENHF IPMKSAEAWQ  300
LSNPPILSLA AIRASLDTIK DAGGIQALRD KSLKLSRYLR DLLEQELADE INILTPADEK  360
ASGCQLSLTV NLHGLDGKTV FDRIEAAGVT CDFRHPNVIR VAPVPLYNSF EDAYRFVTIL  420
KDSLK                                                             425

SEQ ID NO: 30              moltype = AA   length = 425
FEATURE                    Location/Qualifiers
source                     1..425
                           mol_type = protein
                           organism = unidentified
SEQUENCE: 30
MNNLFSLEHA QQLDQQDPLH HMRDQFHIPK QDNGDDEIYL CGNSLGLQPK RTQEYLNYEL  60
NQWQKLGVKG HFSGDFPWMP YHEFLTEESA KLVGAKNTEV VCMNSLTANL HFMMVSFYRP  120
SKTRNKILIE DHAFPSDHYA VESQIRFHGF DPDQAMLLAK PREGEETLRT EDLLNLIEMH  180
GDEIALIMLP GVQYYTGQVL DMKTITEAGH AKGCMVGFDL AHATGNIPMN LHDWNVDFAA  240
WCTYKYLNSG PGSVAGCFVH EKHHSNLELP RFAGWWGHDK ESRFRMENRF VPMQSAEAWQ  300
VSNPPILSLA AIRASLDTVK EAGGIDALRE KSLKLTRYLR DLLEQELSEE INILTPADNS  360
ASGCQLSLTV NLHVLDGKTV FDRIEAAGVT CDFRHPNVIR VAPVPLYNSF EDAYRFVSIL  420
KDSLQ                                                             425

SEQ ID NO: 31              moltype = AA   length = 421
FEATURE                    Location/Qualifiers
source                     1..421
                           mol_type = protein
                           organism = unidentified
SEQUENCE: 31
MSNYTLGRDF AQQLDKEDQL AHYRNQFHIP KDKNGDDLIY LCGNSLGLQP KVTKDYINQE  60
LEDWANLGVE GHTEGKNPWL PYHEFLTESM AKVVGAKPIE VVVMNTLTAN LHFMMVSFYK  120
PTKKRYKILI EADAFPSDKY AVESQLRHHG FDDKEGLVLW KAREGEELAN YEDLEAILEA  180
QGDEIALIMI GGVNYYTGQF FDFKRIAALG HKNGCMVGFD CAHGAGNVNL DLHNSGADFA  240
VWCTYKYMNA GPGPSLSGCFV HERHAHNKDL NRFTGWWSHN KETRFNMRGE FDQLPGAEGW  300
QLSNPPILSM AAIKASADIF AEVGMEKLTQ KSKKLTGYFE FLLNELNNSD IKIITPSNPN  360
ERGCQLSIQV KNADKALHHK LTESGVISDW REPDVIRCAP VPLYNSFEDV YNMVERLKAC  420
L                                                                 421

SEQ ID NO: 32              moltype = AA   length = 428
FEATURE                    Location/Qualifiers
source                     1..428
                           mol_type = protein
                           organism = unidentified
SEQUENCE: 32
MTTTDFEYTE DFAKRMDDLD PFRHFRSMFH FPYVNGKEAI YFCGNSLGLQ PKSVREYLDR  60
ELKNWELMAV DGHFHGEDAW YHVRKKSKPA LAEIVGAHEH EVVAMNNLSS NLHFLMVSFY  120
RPTKERYKII TEAGAFPSDM YMLETQVKPH GFDPADAIIE VAPRPGEYTI RTEDILAAIE  180
DNQDELALVM MAGLQYYTGQ VFDMEAITKA GHGIGVPVGF DLAHAAGNIP LRLHDWGVDF  240
AAWCSYKYLN SGPGNISGIF VHERHADNTE LPRFGGWWGH DEAIRFKMEK GFEPMYGADG  300
WQLANSNVLA LAVHQASLDI FQEAGMERLR TKSELLTGYL EFLIRKVGFA NGVLEIITPN  360
NPKERGCQLS LLVHKGGKLV FDHLYANGVV GDWRHPNVIR VAPTPLYNSF TDVFRFAKIL  420
EHSLQKFA                                                          428

SEQ ID NO: 33              moltype = AA   length = 429
FEATURE                    Location/Qualifiers
source                     1..429
                           mol_type = protein
                           organism = Mucilaginibacter paludis
SEQUENCE: 33
MNYQNTLAFA RELDEQDNLA GFRNEFIIPQ HHGRDMIYLC GNSLGLQPKA TAGVIAEQLS  60
NWGSLAVEGW FEGDSPWMHY HKKLTEPLAA IVGALNTEVV AMNTLTVNLH FLLVSFYRPT  120
AKKYKILMEG GAFPSDQYAI ESQVHFHGYQ PDDAIIEVFP RAGEDTLRTE DIIRTIHDHA  180
DDLALVLFGG INYYTGQFYD LEQITQAAHQ VGAYAGFDLA HAAGNVPLQL HHWQVDFACW  240
CSYKYMNSSP GGISGAFIHE KHFGNKELNR FAGWWGYRED KRFEMKPGFK PQEGAEGWQV  300
SCSPLLLMAA HKASLNVFEK AGYIEPLRKK SKLLTGYLEY LIEGINTAHQ KQLFKIITPK  360
NENERGCQLS IVCDNGKAIF DQLVEGGVLG DWREPDVIRL SPIPLYNSFE DVYLAGKLLA  420
GSVTQFFAE                                                         429
```

-continued

```
SEQ ID NO: 34            moltype = AA  length = 425
FEATURE                  Location/Qualifiers
source                   1..425
                         mol_type = protein
                         organism = Myroides odoratimimus
SEQUENCE: 34
MSFENTLAYA KSLDEKDPLA KYRDEFNFPE VNGKQVIYFT GNSLGLQPKR AVEYVNEVMN    60
DWGALAVEGH FYAEKPWWDY HERLSEPLSR IVGAKSSEIT VMNTLTVNLH LLMTTFYRPT   120
ASKYKIICEE KAFPSDQYLI QSQVRLHGLD PKEAIIELKK RPGEHNFRLE DILEKIDEVG   180
EEVALVLIGG LNYYTGQVFD IQTITAHAHQ YGAKVGWDLA HAAGNIELKL HEWNVDFAAW   240
CSYKYMNAGP GSASGCFIHE RYHTDKDLVR LAGWWGHNKE RRFLMEKKFD AVESAHGWQI   300
SNPSILSLAP YLASIEMFDE VGMEALITKQ RKITAYLEFV MEDVAKAVNA NYELITPKEE   360
SERGSQLSVF LHGKGKDLFS YLMNEGVIVD WREPNVVRLA PVPFYTSYED IYRFGEILKK   420
ADSLF                                                              425

SEQ ID NO: 35            moltype = AA  length = 426
FEATURE                  Location/Qualifiers
source                   1..426
                         mol_type = protein
                         organism = unidentified
SEQUENCE: 35
MTTPHAFEDT EAFAHTLDAE DALRGYRDAF HFPPGPDGKP VVYLAGNSLG LQPRNAARYI    60
QEELEDWARL GVEGHHHGRH PWLHYHELVT EQAARLVGAK PLEVVVMNTL SVNLHLMMVS   120
FYRPTKQRFK ILVEAGAFPS DQYAVASQVR FHGHDAREAV LELKPREGEE TLRTEDILDT   180
LERHGHEVAL VMLGSVNYLT GQAFDLAAIT KAAHAKGCLV GFDLAHGAGN LKLSLHDDGP   240
DFAVWCSYKY LNAGPGALGG VFVHERHAHT KDLPRFEGWW GHDKQTRFQM GPTFHALPGA   300
EGWQLSNPPI FQLAALRASL ELFDQAGMAA LRAKSERLTG YLEFLLDKLP QGFVRITTPR   360
DVKQRGAQLS LRFRGEPQGL LKRMGDAGIV CDFRKPDIIR AAPAPLYNSF TDVYRFVKAL   420
EGYARE                                                             426

SEQ ID NO: 36            moltype = AA  length = 425
FEATURE                  Location/Qualifiers
source                   1..425
                         mol_type = protein
                         organism = unidentified
SEQUENCE: 36
MTTHSFEDTE DFARRADEAD ALRSFRDAFH FPPGTDGKPL VYLAGNSLGL QPKNAARYVQ    60
EELEDWARFG VEGHHHGRHP WLHYHELVTE QAARLVGAKP QEVVVMNTLT VNLHLMMVSF   120
YRPTKTRFKI LVEGGAFPSD QYAVASQARF HGYDPREAIL ELKPRPGEET LRTEDILATL   180
DQHGHEVALV MLGSVNYLTG QAFDIPAITK TAHAKGCFVG FDLAHGAGNL KLALHDDGPD   240
FAVWCSYKYL NGGPGALAGV FVHERHARSK DIPRFEGWWG HDKATRFQMG PTFDPLPGAE   300
GWQLSNPPIL QLAALRASFE LFDQAGMEAL RAKSEKLTGY LEFLLEKLPP GFVRIITPRD   360
VKQRGAQLSL RFKGEAQGML KRLSDAGIIC DFRKPDIIRA APAPLYCSFT DVYRFVRTLE   420
AHARD                                                              425

SEQ ID NO: 37            moltype = AA  length = 426
FEATURE                  Location/Qualifiers
source                   1..426
                         mol_type = protein
                         organism = unidentified
SEQUENCE: 37
MTTPYLFEDS ESFARKLDAE DALRGYRDAF HFPPGPDGKP VVYLAGNSLG LQPRNAARYI    60
QEELEDWARL GVEGHHHGRH PWLHYHELVT EHAARLVGAK PLEVVVMNTL SVNLHLMMVS   120
FYRPTKQRFK ILVEAGAFPS DQYAVASQVR FHGYDAREAV LELKPREGEE TLRTEDILET   180
IERHGHEVAL VMLGSVNYLT GQAFDLAAIT KAAHAKGCFV GFDLAHGAGN LRLSLHDDGP   240
DFAVWCSYKY LNAGPGALGG VFVHERHAHT KDLPRFEGWW GHDKQTRFQM GPTFSALPGA   300
EGWQLSNPPI FQLAALRASL ELFDQAGMAA LRAKSERLTG YLEFLLDRLP EGFVRITTPR   360
DVKQRGAQLS LRFRGEPQGL LKRLGDAGII CDFRKPDIIR AAPAPLYNSF TDVYRFVKTL   420
EGHARE                                                             426

SEQ ID NO: 38            moltype = AA  length = 428
FEATURE                  Location/Qualifiers
source                   1..428
                         mol_type = protein
                         organism = unidentified
SEQUENCE: 38
MINQYQSNQA YAREQDARDP LRQFREQFII PPAKSGGEAI YFCGNSLGLQ PKNTRSYLDR    60
ELEKWATYAV DGHFHAPEPW LHYHRLLKEP LARIVGAKPE EVVVMNNLSS NLHFLMVSFY   120
QPTTKRYKVL MEGGAFPSDQ YAVESQVKFR GYTPEEAIVE VFPREGEQTL RTEDILAAIE   180
QHQDELALVL FAGLQYYTGQ VFDMAAITKA GQAAGAKVGF DLAHAAGNVP LQLHDWGVDF   240
AAWCSYKYLN SGPGSNSGIF VHERYANQAE LPRFAGWWGH DEKERFLMQK GFKPMYGADG   300
WQLSNGNILP LAAQRASLEI FEQAGMDNLR QKSIQLTGYL EYLIREEVSS KANRLQIITP   360
SQPEERGCQL SLFVEKNGKQ LFEQISQAGV VGDWREPNVI RVAPTPLYNT FTDVFQFAQL   420
LKKAIKEQ                                                           428

SEQ ID NO: 39            moltype = AA  length = 428
FEATURE                  Location/Qualifiers
source                   1..428
```

-continued

```
                          mol_type = protein
                          organism = unidentified
SEQUENCE: 39
MIFENSHSFA YVLDEQDELR SFREQFIMPV IDGKQQIYFL GNSLGLQPKR TNDYLQQVLN    60
KWANYGVEGF FMGEQPWLQY HDHLTKPLST IVGALPHEVV AMNQLTVNLH LLLVSFYNPH   120
GKRNKIICEA KAFPSDQYML ETHVKYCGFN PDDVIVEVGP RKGEHTIRHE DILQAIQQHK   180
DELALVLWGG MNYYTGQLFD MAAITKAAQA VGAKVGFDLA HAAGNVPLQL HNWNVDFAAW   240
CSYKYMNSGP GGIGGAYIHE RYHNDTSLPR FAGWWGYDKA TRFLMQKGFN ATRSAEGWQL   300
STPSPLLYAA HRAALDLFME AGFNRLQNKR QLLNKWLWFL LDDLNNAQTE PVVEFITPRN   360
EAERGCQVSM LMLQQGKQVF DELARAGVIV DWREPNVIRL APVPLYNSFE EVWQFTNILR   420
QILQLQHA                                                           428

SEQ ID NO: 40              moltype = AA   length = 420
FEATURE                    Location/Qualifiers
source                     1..420
                           mol_type = protein
                           organism = unidentified
SEQUENCE: 40
MNFKTDHNFA IELNKSDSLS RFRESFHIPK HTDGTDSIYL CGNSLGLQPR QTKTFLNQEL    60
DDWARLGVEG HFHAAHPWMP YHEFLTETTA QIVGAKPHEV VIMNTLTTNL HLMMVSFYQP   120
KGKRTKIIIE ADAFPSDRYA VASQVKFHGH DDKENIIEWS PRAGEHTPRI EDLENLLKEQ   180
GDEIALIMVG AVNYYTGQFF DLKKITELGH AAGAMVGFDC AHGAGNVDLQ LHNSGADFAV   240
WCTYKYMNSG PGSLGGCFVH ERHASNSDLP RFTGWWGHNK DTRFKMRDDF EPMHGAEGWQ   300
LSNPPILSMV AIRASLDLFA QAGFENLRQK SIQLTNYLEY LLSNLEGDRI SIITPENPKD   360
RGCQLSLAVK NADKSLFDAI TEKGVIADWR EPDVIRIAPV PLYNNYEDCW RFVDVLKSEL   420

SEQ ID NO: 41              moltype = AA   length = 431
FEATURE                    Location/Qualifiers
source                     1..431
                           mol_type = protein
                           organism = Pedobacter agri
SEQUENCE: 41
MKLENTLAFA KEQDEKDELK HFRDQFLFPK YQDKFFIYLC GNSLGLQPKV AKEVINSQLD    60
NWANLAVEGW FDGEEPWMYY HKELKKLMAP IVGALPSEVC PMNTLTVNLH LLMISFYQPQ   120
GKRFKIIMEG GAFPSDQYAI ESQVRFHGFD PSDAIIEVFP REGEEILRTE DIVAKIKEHG   180
DEIALLLFGG INYYTGQWYD MENITKAGHS IGAMVGWDLA HAAGNVPVKL HDWNVDFACW   240
CSYKYQNAGP GGISGIFVHE KHFENKALNR FAGWWGYQEN KRFKMEKGFV PEAGADGWQV   300
SCTQVMPMAL YHASLQIFKE AGFLNTLRNK SISLTSYLEF VVNELNIELE KEQYKIITPK   360
NSAERGAQLS IIAARNGKEI FDGLLAHGIL GDWREPNVIR LSPVPLYNSF EDIYQTGKAL   420
SEVTRKILTT A                                                       431

SEQ ID NO: 42              moltype = AA   length = 449
FEATURE                    Location/Qualifiers
source                     1..449
                           mol_type = protein
                           organism = unidentified
SEQUENCE: 42
MKVVDNKKTG LFNYIPFLWI FGTMNFENTL AFAQGLDQAD PLRDLRNEFL FPQQNGKPFI    60
YLCGNSLGLQ PKVAREVLDR QLNNWQNLAV EGWFEGETPW MYYHKALKEL MAPIVGARPA   120
EVCPMNTLTV NLHLLMVSFY KPKAKRFKIM MEAGAFPSDQ YAIESQVRFH GYDPKDAIIE   180
VSPRPGEYTL RTEDILEQIS LQGDQIALVL FGGINYFTGQ WFDMEAITRA GHQAGAVVGF   240
DLAHAAGNVP VQLHDWDVDF ACWCSYKYQN SGPGGISGIF VHERHFGDQT LSRFAGWWGY   300
QESQRFKMEK GFVPEAGADG WQVSCTQVMP MALYHAALQI FEKAGFIGPL RKKSKALTAY   360
LFYLINEVNN ELCEMQYQVI TPSSAEDRGA QVSIIAKANG KYIFEQLVAN NVLGDWREPN   420
VIRLSPVPSY NSFEDVFRTA ELLLQIGRK                                     449

SEQ ID NO: 43              moltype = AA   length = 428
FEATURE                    Location/Qualifiers
source                     1..428
                           mol_type = protein
                           organism = unidentified
SEQUENCE: 43
MNFENNLAFA QSLDQADPLS SFRHDFLFPQ QNGNPFIYLC GNSLGLQPKA VRKVVDEQLN    60
NWRNLAVEGW FEGDNPWMFY HKELKKLMGP LVGASTDEVC PMNTLTVNLH LLMVSFYKPV   120
RGRFKIIMEA GAFPSDQYAV ESQVRFHGYD AKEAIVEVAP RIGEYILRTE DILAQIAKHG   180
DEVALVLFSG VNYFTGQWFD MEAITMAGHA EGAVVGFDLA HAAGNVPLKL HDWDIDFACW   240
CSYKYQNSGP GGISGIFVHE KHFTDTTLNR FAGWWGYQQA HRFKMEKGFL PEPGADGWQV   300
SCTQVMPMAL YFASLQIFEK AGFIEPLRLK SKTLTSYLPH IVNQVNKLLS CEQFEIITPD   360
NENERGAQVS IIAKQKGKEI FEKLIANNVL GDWREPNVIR LSPVPLYNSF EDVFRTGELL   420
LQITKGVI                                                           428

SEQ ID NO: 44              moltype = AA   length = 428
FEATURE                    Location/Qualifiers
source                     1..428
                           mol_type = protein
                           organism = Rhodonellum psychrophilum
SEQUENCE: 44
MKDIKYEYSE FFARQLDNED PLKDFRNEFY FPKIEGKEAI YFCGNSLGLQ PRSTKEYIQR    60
ELDNWAELAV DGHFKGEDAW YHVRKKSKPA LSEIVGAHEH EVVAMNNLSS NLHFLMVSFY   120
```

```
RPSKTRFKII  TEAGAFPSDM  YMLETQVKFH  GLDPEKTIIE  VAPRPGEHTL  RTEDILLAIE   180
EQGEELALVM  MAGLQYYTGQ  VFDMESITRA  GHSVGANVGF  DLAHAAGNVP  MSLHDWGVDF   240
ATWCSYKYMN  SGPGNVSGVF  VHERHAQNPD  LPRFAGWWGH  DEEERFKMEK  GFKPMYGADG   300
WQVANSNVLA  LAAHQSSLDI  FERAGIKNLR  EKSELLTGYL  EFLIQQISGD  SGVIEIITPK   360
NPQERGCQLS  LLVHKGGKAV  FDELYLNGII  GDWRHPKVMR  IAPTPLHNSF  LDVFRFAQIL   420
EKSILKFA                                                                 428

SEQ ID NO: 45        moltype = AA   length = 430
FEATURE              Location/Qualifiers
source               1..430
                     mol_type = protein
                     organism = Salinispora arenicola
SEQUENCE: 45
MNKEELDQEE  KAANRLDTAD  PGHRHLFHLP  PSDGGRYQQA  AYLAGNSLGL  QPLATRDELL   60
ADLDAWRRLG  VEGHLEADRP  WLPYHELLTA  PTARLVGARP  AEVVVMNSLT  VNLHLLMVSF   120
YRPVGARTRI  VIEDNAFPSD  SYAVRSQARF  HGLDPDTTVV  RLAPRPGEDT  LRTVDVLDLL   180
AAEGDTIALV  LLGGVNYLTG  ELLDIPAITA  AGRAAGAAVG  WDLAHAAGNV  PLSLHDWDVD   240
FAAWCSYKYL  NSGPGGLSSV  FVHERHLADP  TLPRFEGWWS  TDAAVRFEMS  PVARPPATAE   300
AWQVSNPPIF  AMGPVRTSLE  LFDSVGMTAL  RERSVRLTGY  LEWLLLDQITP  GRQLAVVTPR   360
DPDRRGAQLS  VRVGSGSAAE  LTKRLRCEYG  VIADAREPDI  VRFAPVPLYS  TYHDCWRVAD   420
ALAATVEVRG                                                               430

SEQ ID NO: 46        moltype = AA   length = 425
FEATURE              Location/Qualifiers
source               1..425
                     mol_type = protein
                     organism = unidentified
SEQUENCE: 46
MQEVQFEDAL  DYAKAQDVSD  PLAHFRPQFH  FPKQADGSPI  IYLCGNSLGL  QPRLAQQLMQ   60
DEMDVWKELA  VEGHFKAERP  WMTYHEEFSR  QLSPIVGALP  KEITVMNTLS  VNLHLMMVSF   120
YRPTKSRYKI  VIEGGAFPSD  KYAVDSQLRF  HGIDPQDGLI  QLRPRMGEDH  LRTEDILQAL   180
EREKDSIALV  MLSGINYYTG  QCFDMKSITK  KGHEIGAMVG  FDLAHAAGNV  RLQLHDWGMD   240
FAVWCHYKYL  NSGPGCIAGA  FVHERHLNRK  DLPRFEGWWG  HHKESRFKMP  ATFEPAPNAD   300
AWQISNAPIL  AMVPMRASLA  LFNEAGMDRL  LAKSKKLTAY  LEFLLNQLPT  DRIRILTPKD   360
PKDRGAQLSI  QVKGADRSLF  DDLVKNGVIG  DWREPDVIRI  SPAPIYNSFE  DVYRMVQILK   420
KCLQL                                                                    425

SEQ ID NO: 47        moltype = AA   length = 427
FEATURE              Location/Qualifiers
source               1..427
                     mol_type = protein
                     organism = unidentified
SEQUENCE: 47
MTEASMRFEE  GEGFARRMDA  EDPLRSFREE  FLFPQSPQGE  PLVYLAGNSL  GLQPRRAQQY   60
VQEEMEDWAR  LGVEGHFHAR  RPWLPYHENL  TGQTARLVGA  LPLEVVVMNT  LSVNLHLMMV   120
SFYRPTRERF  KILIEGGAFP  SDQYAVASQA  RFHGFDPKDA  VLKLEPRAGE  DTLRTEDILE   180
TLERHGSEIA  LVLLGNVNYL  TGQAFDMKAL  TQAAHARGCR  VGFDLAHGAG  NLRLSLHDDG   240
PDFAVWCSYK  YLNGGPGALG  GVFIHERHAR  AEGLPRFEGW  WGNDKAIRFQ  MGPDFVPLPG   300
AEGWQLSNPP  IFQLAALRAS  MELFDRATMP  SLRGKGDRLT  GYLEFLLDRL  PSGFVRITTP   360
RDVKARGSQL  SLRFSKDPRR  LLTRLSEAGV  CCDFRSPDII  RAAPAPLYNS  FQDVYRFVKV   420
LESHARD                                                                  427

SEQ ID NO: 48        moltype = AA   length = 423
FEATURE              Location/Qualifiers
source               1..423
                     mol_type = protein
                     organism = Xanthomonas axonopodis
SEQUENCE: 48
MTDPLSRAHA  AALDAADPLR  NLRDAFVFPQ  HGDDDQTYFV  GNSLGLQPRA  ARAMVDEVLD   60
QWGALAVEGH  FTGPTQWLTY  HQLVRDALAR  VVGAQPGEVV  AMNTLSVNLH  LMMASFYRPT   120
AERGAILIEA  GAFPSDRHAV  ESQLRLHGLD  PATHLIEVEA  DEPNGTVSMS  AIAEAIAQHG   180
PHLALVLWPG  IQYRTGQAFD  LAEIVRLARA  QGAAVGFDLA  HAVGNLPLTL  HDDGVDFAVW   240
CHYKYLNAGP  GAVGGCFVHA  RHATSDLPRM  AGWWGHEQQT  RFRMDPQFVP  SPGAEGWQLS   300
NPPVLALAPL  RASLALFDQA  GMAALRAKSE  QLTGHLEQLI  HARAPQVLQI  VTPVEPARRG   360
CQLSLRVAGG  RARGRALFEH  LHAAGVLGDW  REPDVIRIAP  VPLYNRFSDL  HTFVEQVEAW   420
AAA                                                                      423

SEQ ID NO: 49        moltype = AA   length = 422
FEATURE              Location/Qualifiers
source               1..422
                     mol_type = protein
                     organism = Psychroflexus gondwanensis
SEQUENCE: 49
MKYQNTKSFA  EQLDEADPLK  AYRSEFLFPK  AKDGSPKVYL  CGNSLGLQPK  QTSAFIQQEL   60
QDWADLGVEG  HSHATHPWMT  SNEDLADSMA  KIVGAQPQEV  VIMNTLTVNL  HLMMVSFYKP   120
TPKKFKILIE  SDAFPSDKYA  VESQLKFHNI  DPKEGLLLWK  PRPGEHLCRT  EDFEQIIEEH   180
GDEIALVMIG  STNYYSGQAY  DLKRITEVSK  TKDITVGFDL  AHGAGNIQPN  LHDIGADFAV   240
WCTYKYLNSG  PGSLGGCFIH  EKHIADEHIN  RFVGWWGHNK  DSRFNMRVDF  DPIPTADGWQ   300
LSNPPILSLA  GTRSSLDLFD  KAGFDNIRKK  SVLLTGFLEF  LIDDLDMEEI  SILTPRSPEE   360
```

```
RGCQLSIQVK NANKSLFHQL MDKGVVADWR EPDVIRIAPA PLYNSYTDVF TFVEILKHCL      420
NA                                                                    422

SEQ ID NO: 50              moltype = AA   length = 422
FEATURE                    Location/Qualifiers
source                     1..422
                           mol_type = protein
                           organism = Lewinella cohaerens
SEQUENCE: 50
MTYQATREYA QSQDDKDPMR GFRERFHLPR QANGEPFIYL CGNSLGLQPK STKAAIDQEL      60
LDWQNLGVEG HLHAKNPWLP YHEFLTEKMA EIVGAKPIEV VMMNTLTVNL HLMMVSFYRP      120
EGKRTKILME ADAFPSDRYA ISSQLKFHGY DPAEHLVELK ARDGEVLIRE EDIAHILEEQ      180
GAEIALVLLG NTNYYTGQFF NMPEITKLAH AQGCMVGFDC AHGAGNVPLD LHDSGADFAV      240
WCSYKYINSG PGSVSGCFVH ERHAHDKELP RFTGWWGHNK VTRFGMRDDF DPIPGVEAWQ      300
LSNPPILSLA AIKASLEVFA EAGMNNLRQK SLALTGYLEY LVDQLPGGKI SIITPRDPER      360
RGCQLSIQVQ DADKSLYEAI SAAGVIADWR EPDVIRVAPV PLYNTFTEVY DFVKILGEKM      420
EA                                                                    422

SEQ ID NO: 51              moltype = AA   length = 425
FEATURE                    Location/Qualifiers
source                     1..425
                           mol_type = protein
                           organism = Lewinella persica
SEQUENCE: 51
MVEEFQNDLA FARKMDERDE LRAYRSQYHM PVQANGQPYV YLCGNSLGLQ PKATEGYLLQ      60
ELEDWKNLGV EGHFHAKNPW MPYHEFLTEA MARVVGAKPS EVVVMNTLTV NLHLMMVSFY      120
RPVGRRKKII IEADAFPSDK YAVESQIRFH GLSPEDCLIE LKARDGEVCL RQEDILGVID      180
AHSEDIALIL LGNTNYYTGQ FFDMKTISEH GHAKGCMVGF DCAHGAGNVP LNLHDSGCDF      240
AVWCNYKYLN SGPGGMGGAF IHERHADSKD IPRFEGWWGH NKETRFKMRD AFDPTPGTEA      300
WQLSNPPILA MVAVWSALKL FDEVGMTRLR KKAISLTGYL EYLVNTLGDD VVNIVTPADP      360
AQRGSQLSIQ VKTADKKLFN KITEAGVIAD WREPDVIRVA PVPMYNSYED VYNFYTILKS      420
AIAGN                                                                 425

SEQ ID NO: 52              moltype = AA   length = 424
FEATURE                    Location/Qualifiers
source                     1..424
                           mol_type = protein
                           organism = Pontibacter roseus
SEQUENCE: 52
MNYQNTLAFA QEQDNLDPLK HFKDRFYFPQ VNGRDAIYFC GNSLGLQPKS AQMYIDNEMY      60
KWANYAVEGH FKVEEPWFNY HRLLTDGAAR VVGARPQEVV IMNQLTVNLH LMLVSFYRPE      120
GRRIKIIMEG GAFPSDQYAL ETQVKFHGYT PEEAIIELFP REGEHTLRTE DILKSIEAAG      180
DELALVLMGG INYYTGQVYD MAAITQAGHG VGAVVGFDLA HAAGNVPLQL HDWGVDFAVW      240
CTYKYLNSGP GGTAGVFVHE RHANNPDLPR FAGWWGHDAS VRFQMKKGFI PMTGAEGWQL      300
SNAQILPMAV HRAALELFDE AGMDNLRAKS EKLTGYLEYL IDDVHVGKEL LEMITRPDPQ      360
ARGCQISLLV KQNARELFNR LMEAGIIVDF REPSVIRVAP TPLYNSFEEV YRFSEILHDC      420
LQSH                                                                  424

SEQ ID NO: 53              moltype = DNA   length = 1304
FEATURE                    Location/Qualifiers
misc_feature               1..1304
                           note = Synthetic polynucleotide
source                     1..1304
                           mol_type = other DNA
                           organism = synthetic construct
SEQUENCE: 53
ccatgggcgg acaccatcat caccaccacg gcggcattga aaaactgaaa cagtatcacg      60
atgaagcgat cagcctggat agccttgatc ccttacagaa attcaaagaa tgctttacat      120
taccgaagga acctggagca ctgtatttct gcagcaatag tctgggcttg cccgcgaaag      180
cggcttccca gaaactggaa gaacagttac agcggtggag cgaattaggc gctcgtggat      240
ggtttgaagg cgaggtaat tggtataaca gcttggaaga gcctattgtg cgtccattga      300
gcaaaatctt aggagcggaa agcaatgaag tgacctgat gaatagcttg accgtgaatc      360
tgcacatgtt gttgattagt ttctatcgtc cgaccaaaat gcgttataag atactgattg      420
atggcccagc ctttccgtcc gatctgtatg ccattaagtc gcatctgtcg tttcataaag      480
aagaagaagg tcttattctg atagaaccgc gtccgggcga acatctggtg caggaagaag      540
actttctgcg cgtcggttat aagcaaggag aggaaattgc gttggtgttt ctgaactgcg      600
tgaattttct gagcggccag gtgctgaaag tggatgaaat cacccgttat gccaaggagg      660
ctggctgctg cgtcggttat gatctggcgc atgcagcagg caatattccc ttaagcttgc      720
atgatcttgg cggcgacttt gcggtggct gctcctacaa atatctgtgc ggaggcccag      780
gaggtccagg catagcctac gttcacgcgc cacatcacca ccaacagttc gtgcgtttca      840
gcgggtggtg gggcaatgat ccgaataccc ggtttacctt ccccaaagag tttgtgccgt      900
atggcggtgc gagctcctgg caggtgagca ccccgtcgat tctggcgaaa ctgccgttaa      960
ttgcggcact ggaggtgttt gaggaagcgg gcatggagaa tatacgtgaa aagagcaaga      1020
aacaaacagc gttcctgtat accctgttag aaaatgctcg gcaccacat tttgatatga      1080
taaccccgaa agaaccggag ctgcgtggct gtcagcttag cctgcgtatc aaatgcagcc      1140
gtagcgaaga gatcttacgg aagctggaac gtttaggcat tacatgcgat ttccgttcgc      1200
cgaacattct gcgtgtggcg ccgagcccgt gtacaccag cttttacgaa atctatcgtt      1260
ttgcgtacac ctttctggaa gtcctgaaaa ccatttgaga attc                     1304
```

-continued

```
SEQ ID NO: 54          moltype = AA   length = 431
FEATURE                Location/Qualifiers
REGION                 1..431
                       note = Synthetic polypeptide
source                 1..431
                       mol_type = protein
                       organism = synthetic construct
SEQUENCE: 54
MGGHHHHHHG GIEKLKQYHD EAISLDSLDP LQKFKECFTL PKEPGALYFC SNSLGLPAKA  60
ASQKLEEQLQ RWSELGARGW FEGEGNWYNS LEEPIVRPLS KILGAESNEV TLMNSLTVNL  120
HMLLISFYRP TKMRYKILID GPAFPSDLYA IKSHLRFHKK EEGLILIEPR PGEHLVQEED  180
FLRVIKKQGE EIALVFLNCV NFLSGQVLKV DEITRYAKEA GCCVGYDLAH AAGNIPLSLH  240
DLGGDFAVGC SYKYLCGGPG GPGIAYVHAS HHHQQFVRFS GWWGNDPNTR FYFPKEFVPY  300
GGASSWQVST PSILAKLPLI AALEVFEEAG MENIREKSKK QTAFLYTLLE NARGTHFDMI  360
TPKEPELRGC QLSLRIKCSR SEEILRKLER LGITCDFRSP NILRVAPSPL YTSFYEIYRF  420
AYTFLEVLKT I                                                       431

SEQ ID NO: 55          moltype = AA   length = 464
FEATURE                Location/Qualifiers
REGION                 1..464
                       note = Synthetic polypeptide
source                 1..464
                       mol_type = protein
                       organism = synthetic construct
SEQUENCE: 55
MEPSSLELPA DTVQRIAAEL KCHPTDERVA LHLDEEDKLR HFRECFYIPK IQDLPPVDLS  60
LVNKDENAIY FLGNSLGLQP KMVKTYLEEE LDKWAKIAAY GHEVGKRPWI TGDESIVGLM  120
KDIVGANEKE IALMNALTVN LHLLMLSFFK PTPKRYKILL EAKAFPSDHY AIESQLQLHG  180
LNIEESMRMI KPREGEETLR IEDILEVIEK EGDSIAVILF SGVHFYTGQH FNIPAITKAG  240
QAKGCYVGFD LAHAVGNVEL YLHDWGVDFA CWCSYKYLNA GAGGIAGAFI HEKHAHTIKP  300
ALVGWMGHEL STRFKMDNKL QLIPGVCGFR ISNPPILLVC SLHASLEIFK QTMKALRKKS  360
VLLTGYLEYL IKHNYGKDKA ATKKPVVNII TPSHVEERGC QLTITFSVPN KDVFQELEKR  420
GVVCDKRNPN GIRVAPVPLY NSFHDVYKFT NLLTSILDSA ETKN                   464

SEQ ID NO: 56          moltype = AA   length = 464
FEATURE                Location/Qualifiers
REGION                 1..464
                       note = Synthetic polypeptide
source                 1..464
                       mol_type = protein
                       organism = synthetic construct
SEQUENCE: 56
MEPSSLELPA DTVQRIAAEL KCHPTDERVA LHLDEEDKLR HFRECFYIPK IQDLPPVDLS  60
LVNKDENAIY FLGNSLGLQP KMVKTYLEEE LDKWAKIAAY GHEVGKRPWI TGDESIVGLM  120
KDIVGANEKE IALMNALTVN LHLLMLSFFK PTPKRYKILL EAKAFPSDHY AIESQLQLHG  180
LNIEESMRMI KPREGEETLR IEDILEVIEK EGDSIAVILF SGVHFYTGQH FNIPAITKAG  240
QAKGCYVGFD LAHAVGNVEL YLHDWGVDFA CWCSYKYLNA GAGGIAGAFI HEKHAHTIKP  300
ALVGWLGHEL STRFKMDNKL QLIPGVCGFR ISNPPILLVC SLHASLEIFK QTMKALRKKS  360
VLLTGYLEYL IKHNYGKDKA ATKKPVVNII TPSHVEERGC QLTITFSVPN KDVFQELEKR  420
GVVCDKRNPN GIRVAPVPLY NSFHDVYKFT NLLTSILDSA ETKN                   464

SEQ ID NO: 57          moltype = AA   length = 420
FEATURE                Location/Qualifiers
source                 1..420
                       mol_type = protein
                       organism = Chlamydophila pecorum
SEQUENCE: 57
IEKLKQYHDE AISLDSLDPL QKFKECFTLP KEPGALYFCS NSLGLPAKAA SQKLEEQLQR  60
WSELGARGWF EGEGNWYNSL EEPIVRPLSK ILGAESNEVT LMNSLTVNLH MLLISFYRPT  120
KMRYKILIDG PAFPSDLYAI KSHLRFHKKE EGLILIEPRP GEHLVQEEDF LRVIKKQGEE  180
IALVFLNCVN FLSGQVLKVD EITRYAKEAG CCVGYDLAHA AGNIPLSLHD LGGDFAVGCS  240
YKYLCGGPGG PGIAYVHASH HHQQFVRFSG WWGNDPNTRF YFPKEFVPYG GASSWQVSTP  300
SILAKLPLIA ALEVFEEAGM ENIREKSKKQ TAFLYTLLEN ARGTHFDMIT PKEPELRGCQ  360
LSLRIKCSRS EEILRKLERL GITCDFRSPN ILRVAPSPLY TSFYEIYRFA YTFLEVLKTI  420
```

ADMINISTRATION OF KYNURENINE DEPLETING ENZYMES FOR TUMOR THERAPY

BACKGROUND OF THE INVENTION

The present application is a divisional of U.S. application Ser. No. 16/996,806, filed Aug. 18, 2020, which is a divisional of U.S. application Ser. No. 16/373,588, filed Apr. 2, 2019, now U.S. Pat. No. 10,772,913, which is a divisional of U.S. application Ser. No. 15/351,060, filed Nov. 14, 2016, now Abandoned, which is a divisional of U.S. application Ser. No. 14/473,040, filed Aug. 29, 2014, now U.S. Pat. No. 9,808,486, which claims the priority benefit of United States provisional application numbers 61/872,132, filed Aug. 30, 2013 and 61/986,366, filed Apr. 30, 2014, the entire contents of each of which are incorporated herein by reference.

The invention was made with government support under Grant No. R01 CA154754 awarded by the National Institutes of Health. The government has certain rights in the invention.

This application contains a Sequence Listing XML, which has been submitted electronically and is hereby incorporated by reference in its entirety. Said Sequence Listing XML, created on Dec. 5, 2022, is named UTSBP1018USD4.xml and is 83,630 bytes in size.

1. FIELD OF THE INVENTION

The invention generally relates to compositions and methods for the treatment of cancer with enzymes that deplete L-kynurenine or L-3-hydroxykynurenine. More particularly, it concerns the engineering, pharmacological optimization and use of bacterial and mammalian enzymes with L-kynurenine degrading activity suitable for human therapy.

2. DESCRIPTION OF RELATED ART

Overexpression of indolamine-2,3-dioxygenase isoforms (IDO1 or IDO2) by cancer cells or reprogramming of cancer infiltrating leukocytes to express either of these enzymes has been shown to have a profound effect on attenuating adaptive immune responses to cancer. IDO1 and IDO2 as well as the enzyme tryptophan 2,3-dioxygenase (TDO), whose expression by stromal cells may be induced by some tumors, catalyze the rate limiting step in tryptophan (Trp) catabolism to L-kynurenine (KYN) (Godin-Ethier et al., 2011). Tumors exchange a cytosolic KYN molecule for an extracellular Trp molecule using a LAT1-like amino acid exchanger (Kaper et al., 2007), which has the dual effect on immune cells of locally elevating levels of KYN while locally depleting Trp levels. Neighboring immune cells internalize KYN, where it is an activating ligand for the aryl hydrocarbon receptor (AHR) resulting in the expression of numerous cytokines and chemokines that lead to tumor tolerance through immune cell differentiation and/or induction of apoptosis (Della Chiesa et al., 2006; Opitz et al., 2011; Song et al., 2011). Additionally, other KYN-related compounds formed from kynurenine, most notably kynurenic acid also exert an immunosuppressive effect by serving as agonists of the orphan GPCR GPCR35. Inhibition of KYN formation (and thus inhibition of the formation of KYN metabolism byproducts, including kynurenic acid, 3-hydroxyl kynurenine and quinolinic acid, via the inhibition of IDO1 or TDO has received a significant amount of attention as a cancer target (Chen and Guillemin, 2009; Rutella et al., 2009; Prendergast, 2011). Substrate analog inhibitors, such as 1-DLmethyltryptophan, for IDO1 have been developed and have shown initial promise in overcoming cancer induced tumor tolerance thus restoring the ability of the native immune system to fight tumors (Lob et al., 2009). However, KYN is also produced by tryptophan 2,3-dioxygenase (TDO), which is also frequently expressed in tumors and this enzyme is not inhibited by 1-DL-methyltryptophan (Pilotte et al., 2012). There are also additional concerns with the D-isomer of 1-DL-methyltryptophan (1-D-MT) currently in phase 1 and 2 clinical trials. Paradoxically, 1-D-MT can upregulate IDO1 expression, actually increasing KYN levels and inducing immunosuppression in certain cancers (Opitz et al., 2011).

Controlling tumor production of KYN is the focus of much research and has the potential to treat, among others, cancers such as breast cancer, ovarian, glioblastoma, and pancreatic carcinoma. KYN is known to suppresses proliferation as well as induce apoptosis in T cells and NK cells (Opitz et al., 2011; Mandi and Vacsei, 2012) enabling tumors to evade detection and destruction by a patient's immune system. KYN is a potent ligand of the aryl hydrocarbon receptor (AHR) whose activation in T cells induces differentiation into CD25+FoxP3+T regulatory cells (Tregs) (Mezrich et al., 2010). KYN has also been shown to prevent cytokine mediated up-regulation of specific receptors (NKp46 and NKG2D) required for NK mediated cell killing tumor cell lines (Della Chiesa et al., 2006), an action that is also likely mediated by its agonistic effect on AHR (Shin et al., 2013). There is also clinical evidence linking elevated serum KYN levels and decreased survival in multiple types of cancer. In healthy patients, KYN levels in serum are in the range of 0.5 to 1 μM. In patients with cancer types that produce KYN, such as diffuse large B-cell lymphoma, serum KYN levels were measured to be as much as 10 times higher (Yoshikawa et al., 2010; de Jong et al., 2011; Yao et al., 2011) and were prognostic for survival among lymphoma patients receiving the same treatment regimen; those with serum levels below 1.5 μM exhibited a 3 year survival rate of 89%, compared to only 58% survival for those with KYN levels above 1.5 μM. This difference in survival was attributed to the immune suppressing effects of KYN(Yoshikawa et al., 2010). The use of small molecule IDO inhibitors, such as 1-D-MT, has demonstrated the utility of controlling KYN levels in restoring immune function, but the off target effects of IDOL up-regulation by 1-D-MT and lack of inhibition for TDO and the IDO1 isoform are of concern.

The present invention discloses the use enzymes for the specific depletion of KYN and its metabolites in tumors and/or in the blood. KYN depleting enzymes are used to lower KYN concentrations for the treatment of tumors expressing IDO1, IDO2, or TDO thus preventing tumor-mediated tolerogenic effects and instead mediating tumor-ablating pro-inflammatory responses. Notably, the use of enzymes for the depletion of KYN and KYN metabolic byproducts circumvents the problems associated with small molecule inhibitors of IDO isoforms and TDO discussed above and further completely circumvents off target effects that are very commonly accompany small molecule drugs and lead to unpredicted toxicities and side effects.

SUMMARY OF THE INVENTION

Aspects of the present invention overcome a major deficiency in the art by providing enzymes that comprise bacterial and mammalian polypeptide sequences capable of degrading L-kynurenine and 3-hydroxy-L-kynurenine and displaying favorable pharmacokinetics in serum as desired for cancer therapy. In some aspects, the kynureninase enzyme may have greater catalytic activity towards kynurenine than 3'OH-kynurenine. A kynureninase from a bacterial species may be used. Such an enzyme may have an amino acid sequence selected from the group consisting of SEQ ID NOs: 7 and 13-52 or a modified version thereof. In particular, the therapeutic may be derived from the *Pseudomonas fluorescens* enzyme, kynureninase (Pf-KYNU). Alternatively, a kynureninase from *Saccharomyces cerevisiae* or *Neurospora crassa* may be used. The therapeutic may be derived from the *Mucilaginibacter paludis* kynureninase enzyme. Further, to prevent adverse effects due to the immunogenicity of heterologous kynureninases, the *Homo sapiens* enzyme or other primate kynureninases displaying >95% sequence identity to the human enzyme may be used. For example, a novel enzyme may have an amino acid sequence selected from the group consisting of SEQ ID NOs: 7-9.

In other aspects, there may be a polypeptide comprising either a native or modified human or primate kynureninase capable of degrading KYN and having activity towards the degradation of 3-hydroxykynurenine or kynurenic acid. In some embodiments, the polypeptide may be capable of degrading KYN under physiological conditions. For example, the polypeptide may have a catalytic efficiency for KYN ($k_{cat}/K_M$) of at least or about 0.01, 0.05, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$ $M^{-1}s^{-1}$ or any range derivable therein.

A modified polypeptide as discussed above may be characterized as having a certain percentage of identity as compared to an unmodified polypeptide (e.g., a native polypeptide) or to any polypeptide sequence disclosed herein. For example, the unmodified polypeptide may comprise at least, or up to, about 150, 200, 250, 300, 350, 400 residues (or any range derivable therein) of a native kynureninase. The percentage identity may be about, at most or at least 40%, 50%, 55%, 60%, 65%, 70%, 75%, 80%, 85%, 90%, 95%, 96%, 97%, 98%, 99% or 100% (or any range derivable therein) between the modified and unmodified polypeptides, or between any two sequences in comparison. It is also contemplated that percentage of identity discussed above may relate to a particular modified region of a polypeptide as compared to an unmodified region of a polypeptide. For instance, a polypeptide may contain a modified or mutant substrate recognition site of a kynureninase that can be characterized based on the identity of the amino acid sequence of the modified or mutant substrate recognition site of the kynureninase to that of an unmodified or mutant kynureninase from the same species or across the species. A modified or mutant human polypeptide characterized, for example, as having at least 90% identity to an unmodified kynureninase means that at least 90% of the amino acids in that modified or mutant human polypeptide are identical to the amino acids in the unmodified polypeptide.

Such an unmodified polypeptide may be a native kynureninase, particularly a human isoform or other primate isoforms. For example, the native human kynureninase may have the sequence of SEQ ID NO: 8. Non-limiting examples of other native primate kynureninase include *Pongo abelii* kynureninase (Genbank ID: XP 002812508.1; SEQ ID NO: 10), *Macaca fascicularis* kynureninase (Genbank ID: EHH54849.1; SEQ ID NO: 11), and Pan troglodytes kynureninase (Genbank ID: XP 003309314.1; SEQ ID NO:

12). Exemplary native polypeptides include a sequence having about, at most or at least 50%, 55%, 60%, 65%, 70%, 75%, 80%, 85%, 90%, 95%, 96%, 97%, 98%, 99% or 100% identity (or any range derivable therein) of SEQ ID NO: 8 or 10-12 or a fragment thereof. For example, the native polypeptide may comprise at least or up to about 10, 20, 30, 40, 50, 60, 70, 80, 90, 100, 150, 200, 250, 300, 350, 400, 415 residues (or any range derivable therein) of the sequence of SEQ ID NO: 8 or 10-12.

In some embodiments, the native kynureninase may be modified by one or more other modifications, such as chemical modifications, substitutions, insertions, deletions, and/or truncations. For example, the modifications may be at a substrate recognitions site of the native enzyme. In a particular embodiment, the native kynureninase may be modified by substitutions. For example, the number of substitutions may be one, two, three, four or more. In further embodiments, the native kynureninase may be modified in the substrate recognition site or any location that may affect substrate specificity.

In one embodiment, an isolated, modified human kynureninase enzyme is provided, wherein the modified enzyme has at least one substitution relative to native human kynureninase (see SEQ ID NO: 8), and wherein the at least one substitution includes a Met or Leu substitution for a Phe normally found at position 306 of native human kynureninase. Thus, in one aspect, an isolated, modified human kynureninase enzyme is provided that comprises a Phe306Met substitution. In another aspect, an isolated, modified human kynureninase enzyme is provided that comprises a Phe306Leu substitution.

In some aspects, the present invention also contemplates polypeptides comprising a kynureninase linked to a heterologous amino acid sequence. For example, the kynureninase may be linked to the heterologous amino acid sequence as a fusion protein. In a particular embodiment, the kynureninase may be linked to amino acid sequences, such as an IgG Fc, albumin, an albumin binding protein, or an XTEN polypeptide for increasing the in vivo half-life.

To increase serum stability, the kynureninase may be linked to one or more polyether molecules. In a particular embodiment, the polyether may be polyethylene glycol (PEG). The polypeptide may be linked (e.g., covalently) to PEG via specific amino acid residues, such as lysine or cysteine. For therapeutic administration, such a polypeptide comprising the kynureninase may be dispersed in a pharmaceutically acceptable carrier.

In some aspects, a nucleic acid encoding such a kynureninase is contemplated. In some embodiments, the nucleic acid has been codon optimized for expression in bacteria. In particular embodiments, the bacteria is *E. coli*. In other aspects, the nucleic acid has been codon optimized for expression in fungus (e.g., yeast), insects, or mammals. The present invention further contemplates vectors, such as expression vectors, containing such nucleic acids. In particular embodiments, the nucleic acid encoding the kynureninase is operably linked to a promoter, including but not limited to heterologous promoters. In one embodiment, a kynureninase may be delivered to a target cell by a vector (e.g., a gene therapy vector). Such viruses may have been modified by recombinant DNA technology to enable the expression of the kynureninase-encoding nucleic acid in the target cell. These vectors may be derived from vectors of non-viral (e.g., plasmids) or viral (e.g., adenovirus, adeno-associated virus, retrovirus, lentivirus, herpes virus, or vaccinia virus) origin. Non-viral vectors are preferably complexed with agents to facilitate the entry of the DNA across the cellular membrane. Examples of such non-viral vector complexes include the formulation with polycationic agents which facilitate the condensation of the DNA and lipid-based delivery systems. An example of a lipid-based delivery system would include liposome based delivery of nucleic acids.

In still further aspects, the present invention further contemplates host cells comprising such vectors. The host cells may be bacteria (e.g., *E. coli*), fungal cells (e.g., yeast), insect cells, or mammalian cells.

In some embodiments, the vectors are introduced into host cells for expressing the kynureninase. The proteins may be expressed in any suitable manner. In one embodiment, the proteins are expressed in a host cell such that the protein is glycosylated. In another embodiment, the proteins are expressed in a host cell such that the protein is aglycosylated.

Certain aspects of the present invention also contemplate methods of treatment by the administration of the kynureninase peptide, the nucleic acid encoding the kynureninase in a gene therapy vector, or the formulation of the present invention, and in particular methods of treating tumor cells or subjects with cancer. The subject may be any animal, such as a mouse. For example, the subject may be a mammal, particularly a primate, and more particularly a human patient. In some embodiments, the method may comprise selecting a patient with cancer.

In some embodiments, the cancer is any cancer that is sensitive to kynurenine depletion. In one embodiment, the present invention contemplates a method of treating a tumor cell or a cancer patient comprising administering a formulation comprising such a polypeptide. In some embodiments, the administration occurs under conditions such that at least a portion of the cells of the cancer are killed. In another embodiment, the formulation comprises such a kynureninase with kynurenine-degrading activity at physiological conditions and further comprising an attached polyethylene glycol chain. In some embodiment, the formulation is a pharmaceutical formulation comprising any of the above discussed kynureninases and pharmaceutically acceptable excipients. Such pharmaceutically acceptable excipients are well known to those of skill in the art. All of the above kynureninases may be contemplated as useful for human therapy.

In a further embodiment, there may also be provided a method of treating a tumor cell comprising administering a formulation comprising a non-bacterial (mammalian, e.g., primate or mouse) kynureninase that has kynurenine-degrading activity or a nucleic acid encoding thereof.

The administration or treatment may be directed to the nutrient source for the cells, and not necessarily the cells themselves. Therefore, in an in vivo application, treating a tumor cell includes contacting the nutrient medium for a population of tumor cells with the kynureninase. In this embodiment, the medium can be blood, lymphatic fluid, spinal fluid and the like bodily fluid where kynurenine depletion is desired.

In accordance with certain aspects of the present invention, such a formulation containing the kynureninase can be administered intravenously, intradermally, intraarterially, intraperitoneally, intralesionally, intracranially, intraarticularly, intraprostaticaly, intrapleurally, intrasynovially, intratracheally, intranasally, intravitreally, intravaginally, intrarectally, intratumorally, intramuscularly, subcutaneously, subconjunctival, intravesicularlly, mucosally, intrapericardially, intraumbilically, intraocularly, orally, topically, by inhalation, infusion, continuous infusion, localized perfusion, via a catheter, via a lavage, in lipid compositions (e.g., liposomes), or by other method or any combination of the forgoing as would be known to one of ordinary skill in the art.

In a further embodiment, the method may also comprise administering at least a second anticancer therapy to the subject. The second anticancer therapy may be a surgical therapy, chemotherapy, radiation therapy, cryotherapy, hormone therapy, immunotherapy or cytokine therapy. In certain aspects, the second anticancer therapy may be an anti-PD-1, anti-CTLA-4, or anti-PD-L1 antibody.

In some embodiment, a cell comprising a chimeric antigen receptor (CAR) and a kynureninase enzyme are contemplated for use in treating a subject with cancer. In some aspects, the cell may be transfected with a DNA encoding the CAR and the kynureninase and, in some cases, a transposase.

The CAR may target any cancer-cell antigen of interest, including, for example, HER2, CD19, CD20, and GD2. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, which is incorporated herein by reference in its entirety. The fragment can also be any number of different antigen binding domains of a human antigen-specific antibody. In a more specific embodiment, the fragment is an antigen-specific scFv encoded by a sequence that is optimized for human codon usage for expression in human cells. For additional examples of CARs, see, for example, WO 2012/031744, WO 2012/079000, WO 2013/059593, and U.S. Pat. No. 8,465,743, all of which are incorporated herein by reference in their entireties.

The kynureninase may be any kynureninase disclosed herein. Methods of transfecting of cells are well known in the art, but in certain aspects, highly efficient transfections methods such as electroporation are employed. For example, nucleic acids may be introduced into cells using a nucleofection apparatus. Preferably, the transfection step does not involve infecting or transducing the cells with virus, which can cause genotoxicity and/or lead to an immune response to cells containing viral sequences in a treated subject.

A wide range of CAR constructs and expression vectors for the same are known in the art and are further detailed herein. For example, in some aspects, the CAR expression vector is a DNA expression vector such as a plasmid, linear expression vector or an episome. In some aspects, the vector comprises additional sequences, such as sequence that facilitates expression of the CAR, such a promoter, enhancer, poly-A signal, and/or one or more introns. In preferred aspects, the CAR coding sequence is flanked by transposon sequences, such that the presence of a transposase allows the coding sequence to integrate into the genome of the transfected cell.

In certain aspects, cells are further transfected with a transposase that facilitates integration of a CAR coding sequence into the genome of the transfected cells. In some aspects, the transposase is provided as DNA expression vector. However, in preferred aspects, the transposase is provided as an expressible RNA or a protein such that long-term expression of the transposase does not occur in the transgenic cells. Any transposase system may be used in accordance with the embodiments. In other aspects, cells may be infected with a lentivirus to facilitate integration of the CAR coding sequence and the kynureninase coding sequence into the genome of the cell.

In one embodiment, a composition comprising a kynureninase or a nucleic acid encoding a kynureninase is provided for use in the treatment of a tumor in a subject. In another embodiment, the use of a kynureninase or a nucleic acid encoding a kynureninase in the manufacture of a medicament for the treatment of a tumor is provided. Said kynureninase may be any kynureninase of the embodiments.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding," with reference to a nucleic acid, are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A—The population of circulating CD4+ regulatory T-cell is significantly smaller in the group treated with active PEG-Pf-KYNU. FIG. 5B—The population of tumor infiltrating CD8+ T-cells shows significantly higher expression of granzyme B and interferon γ.

FIG. 9B—Additive effects were observed with PD1 (antibody)/PEG-Pf-KYNU combination treatment eliminating 60% of tumors and PD1 (antibody)/PEG-Mu-KYNU combination eliminating 20% of tumors compared to 0% tumor elimination with PD1 (antibody) alone. FIG. 9C—Corresponding Kaplan-Meier plot.

FIG. 10B—Corresponding Kaplan-Meier plot depicting a median survival time of 25 days for PEG-Mu-KYNU (−−−), and median survival time of 22 days for heat-inactivated PEG-Mu-KYNU (▬)(arrows indicate treatment days).

DESCRIPTION OF ILLUSTRATIVE EMBODIMENTS

Figure 1:
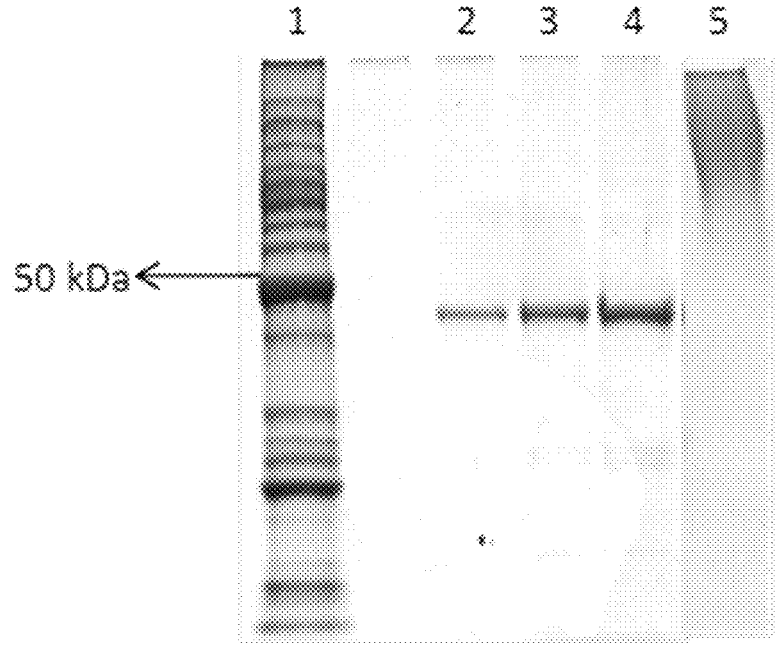
FIG. 1—SDS-PAGE of (lane 1) PRECISION PLUS PROTEIN™ MW standard (BioRad) (lanes 2-4) increasing concentrations of Pf-KYNU and (lane 5) PEG 5,000 MW modified Pf-KYNU.

Kynurenine is a metabolite of the amino acid tryptophan generated via the action of either indolamine-2,3-dioxygenase (IDO) or tryptophan-2,3-dioxygenase (TDO). Kynurenine exerts multiple effects on cell physiology, one of the most important of which is modulation of T cell responses. Many tumor cells regulate the synthesis of IDO and/or TDO to elevate the local concentration of kynurenine, which is accompanied with depletion of tryptophan. High levels of kynurenine serve as a powerful way to inhibit the function of tumor infiltrating T cells that would otherwise attack the tumor.

The present invention provides methods for the use of kynurenine degrading enzymes as a means for depleting local kynurenine levels in the tumor microenvironment as well as in the serum and thus prevent tumor-mediated suppression of T-cell action. Kynurenine hydrolyzing enzymes (kynureninases) convert kynurenine to alanine and anthranilic acid, the latter of which is not known to affect T-cell function. The inventors generated a pharmaceutical preparation of kynureninase enzyme to enable the enzyme to persist for prolonged times under physiological conditions. The inventors then showed that intratumoral administration of the enzyme results in dramatic retardation of growth of an aggressive tumor in mice.

I. Definitions

As used herein the terms "protein" and "polypeptide" refer to compounds comprising amino acids joined via peptide bonds and are used interchangeably.

As used herein, the term "fusion protein" refers to a chimeric protein containing proteins or protein fragments operably linked in a non-native way.

As used herein, the term "half-life" (½-life) refers to the time that would be required for the concentration of a polypeptide thereof to fall by half in vitro or in vivo, for example, after injection in a mammal.

The terms "in operable combination," "in operable order," and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

The term "linker" is meant to refer to a compound or moiety that acts as a molecular bridge to operably link two different molecules, wherein one portion of the linker is operably linked to a first molecule, and wherein another portion of the linker is operably linked to a second molecule.

The term "PEGylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymers of PEG and amino acids have been explored as novel biomaterial that would retain the biocompatibility of PEG, but that would have the added advantage of numerous attachment points per molecule (thus providing greater drug loading), and that can be synthetically designed to suit a variety of applications.

The term "gene" refers to a DNA sequence that comprises control and coding sequences necessary for the production of a polypeptide or precursor thereof. The polypeptide can be encoded by a full-length coding sequence or by any portion of the coding sequence so as the desired enzymatic activity is retained.

The term "native" refers to the typical form of a gene, a gene product, or a characteristic of that gene or gene product when isolated from a naturally occurring source. A native form is that which is most frequently observed in a natural population and is thus arbitrarily designated the normal or wild-type form. In contrast, the term "modified," "variant," or "mutant" refers to a gene or gene product that displays modification in sequence and functional properties (i.e., altered characteristics) when compared to the native gene or gene product.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "therapeutically effective amount" as used herein refers to an amount of cells and/or therapeutic composition (such as a therapeutic polynucleotide and/or therapeutic polypeptide) that is employed in methods to achieve a therapeutic effect. The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "k cat" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies (such as those described in U.S. Pat. No. 7,109,304, which is incorporated herein by reference in its entirety), fused to CD3-zeta transmembrane and endodomains. The specificity of other CAR designs may be derived from ligands of receptors (e.g., peptides) or from pattern-recognition receptors, such as Dectins. In particular embodiments, one can target malignant B cells by redirecting the specificity of T cells by using a CAR specific for the B-lineage molecule, CD19. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a kynureninase.

"Subject" and "patient" refer to either a human or non-human, such as primates, mammals, and vertebrates. In particular embodiments, the subject is a human.

II. Kynureninase Polypeptides

Some embodiments concern modified proteins and polypeptides. Particular embodiments concern a modified protein or polypeptide that exhibits at least one functional activity that is comparable to the unmodified version, preferably, the kynurenine degrading activity or the 3'-hydroxy-kynurenine degrading activity. In further aspects, the protein or polypeptide may be further modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide, such as kynurenine degrading activity or 3'-hydroxy-kynurenine degrading activity. In certain embodiments, the unmodified protein or polypeptide is a native kynureninase, preferably a human kynureninase or the *Pseudomonas fluorescens* kynureninase. It is specifically contemplated that embodiments concerning a "modified protein" may be implemented with respect to a "modified polypeptide," and vice versa.

Determination of activity may be achieved using assays familiar to those of skill in the art, particularly with respect to the protein's activity, and may include for comparison purposes, the use of native and/or recombinant versions of either the modified or unmodified protein or polypeptide.

In certain embodiments, a modified polypeptide, such as a modified kynureninase, may be identified based on its increase in kynurenine and/or 3'-hydroxy-kynurenine degrading activity. For example, substrate recognition sites of the unmodified polypeptide may be identified. This identification may be based on structural analysis or homology analysis. A population of mutants involving modifications of such substrate recognition sites may be generated. In a further embodiment, mutants with increased kynurenine degrading activity may be selected from the mutant population. Selection of desired mutants may include methods, such as detection of byproducts or products from kynurenine degradation.

Modified proteins may possess deletions and/or substitutions of amino acids; thus, a protein with a deletion, a protein with a substitution, and a protein with a deletion and a substitution are modified proteins. In some embodiments, these modified proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A modified protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

III. Enzymatic Kynurenine Degradation for Therapy

In certain aspects, the polypeptides may be used for the treatment of diseases, including cancers that are sensitive to kynurenine depletion, with enzymes that deplete kynurenine, to prevent tumor-mediated tolerogenic effects and instead mediate tumor-ablating pro-inflammatory responses. In certain aspects, kynureninases are contemplated for use in treating tumors expressing IDO1, IDO2, and/or TDO.

Certain aspects of the present invention provide a modified kynureninase for treating diseases, such as tumors.

Particularly, the modified polypeptide may have human polypeptide sequences and thus may prevent allergic reactions in human patients, allow repeated dosing, and increase the therapeutic efficacy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odonto sarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The kynureninase may be used herein as an antitumor agent in a variety of modalities for depleting kynurenine and/or 3'-hydroxy-kynurenine from tumor tissue, or the circulation of a mammal with cancer, or for depletion of kynurenine where its depletion is considered desirable.

Depletion can be conducted in vivo in the circulation of a mammal, in vitro in cases where kynurenine and 3'-hydroxy-kynurenine depletion in tissue culture or other biological mediums is desired, and in ex vivo procedures where biological fluids, cells, or tissues are manipulated outside the body and subsequently returned to the body of the patient mammal. Depletion of kynurenine from circulation, culture media, biological fluids, or cells is conducted to reduce the amount of kynurenine accessible to the material being treated, and therefore comprises contacting the material to be depleted with a kynurenine-depleting amount of the kynureninase under kynurenine-depleting conditions as to degrade the ambient kynurenine in the material being contacted.

The depletion may be directed to the nutrient source for the cells, and not necessarily the cells themselves. Therefore, in an in vivo application, treating a tumor cell includes contacting the nutrient medium for a population of tumor cells with the kynureninase. In this embodiment, the medium may be blood, lymphatic fluid, spinal fluid and the like bodily fluid where kynurenine depletion is desired.

Kynurenine- and 3'-hydroxy-kynurenine-depleting efficiency can vary widely depending upon the application, and typically depends upon the amount of kynurenine present in the material, the desired rate of depletion, and the tolerance of the material for exposure to kynureninase. Kynurenine and kynurenine metabolite levels in a material, and therefore rates of kynurenine and kynurenine metabolite depletion from the material, can readily be monitored by a variety of chemical and biochemical methods well known in the art. Exemplary kynurenine-depleting amounts are described further herein, and can range from 0.001 to 100 units (U) of kynureninase, preferably about 0.01 to 10 U, and more preferably about 0.1 to 5 U kyureninase per milliliter (mL) of material to be treated. Typical dosages can be administered based on body weight, and are in the range of about 5-1000 U/kilogram (kg)/day, preferably about 5-100 U/kg/day, more preferably about 10-50 U/kg/day, and more preferably about 20-40 U/kg/day.

Kynurenine-depleting conditions are buffer and temperature conditions compatible with the biological activity of a kynureninase, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

In a particular embodiment, the invention contemplates methods of using a kynureninase as an antitumor agent, and therefore comprises contacting a population of tumor cells with a therapeutically effective amount of kynureninase for a time period sufficient to inhibit tumor cell growth.

In one embodiment, the contacting in vivo is accomplished by administering, by intravenous intraperitoneal, or intratumoral injection, a therapeutically effective amount of a physiologically tolerable composition comprising an kynureninase of this invention to a patient, thereby depleting the kynurenine source of the tumor cells present in the patient.

A therapeutically effective amount of a kynureninase is a predetermined amount calculated to achieve the desired effect, i.e., to deplete kynurenine in the tumor tissue or in a patient's circulation, and thereby mediate a tumor-ablating pro-inflammatory response. Thus, the dosage ranges for the administration of kynureninase of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

The kynureninase can be administered parenterally by injection or by gradual infusion over time. The kynureninase can be administered intravenously, intraperitoneally, orally, intramuscularly, subcutaneously, intracavity, transdermally, dermally, can be delivered by peristaltic means, can be injected directly into the tissue containing the tumor cells, or can be administered by a pump connected to a catheter that may contain a potential biosensor for kynurenine.

The therapeutic compositions containing kynureninase are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of kynureninase and conversely low serum and tissue levels of kynurenine. Alternatively, continuous intravenous infusion sufficient to maintain concentrations in the blood in the ranges specified for in vivo therapies are contemplated.

IV. Conjugates

Compositions and methods of the present invention involve modified kynureninases, such as by forming conjugates with heterologous peptide segments or polymers, such as polyethylene glycol. In further aspects, the kynureninases may be linked to PEG to increase the hydrodynamic radius of the enzyme and hence increase the serum persistence. In certain aspects, the disclosed polypeptide may be conjugated to any targeting agent, such as a ligand having the ability to specifically and stably bind to an external receptor or binding site on a tumor cell (U.S. Patent Publ. 2009/0304666).

A. Fusion Proteins

Certain embodiments of the present invention concern fusion proteins. These molecules may have a native or modified kynureninase linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the kynureninase may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

B. Linkers

In certain embodiments, the kynureninase may be chemically conjugated using bifunctional cross-linking reagents or fused at the protein level with peptide linkers.

Bifunctional cross-linking reagents have been extensively used for a variety of purposes, including preparation of affinity matrices, modification and stabilization of diverse structures, identification of ligand and receptor binding sites, and structural studies. Suitable peptide linkers may also be used to link the kynureninase, such as Gly-Ser linkers.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, carboxyl-specific groups. Of these, reagents directed to free amino groups have become especially popular because of their commercial availability, ease of synthesis, and the mild reaction conditions under which they can be applied.

A majority of heterobifunctional cross-linking reagents contain a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine kynureninase, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SPDP, and 2-iminothiolane (Wawrzynczak and Thorpe, 1987). The use of such cross-linkers is well understood in the art. Another embodiment involves the use of flexible linkers.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation, or high performance liquid chromatography, will generally be of most use. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

C. PEGylation

In certain aspects of the invention, methods and compositions related to PEGylation of kynureninase are disclosed. For example, the kynureninase may be PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

V. Proteins and Peptides

In certain embodiments, the present invention concerns novel compositions comprising at least one protein or peptide, such as a kynureninase. These peptides may be comprised in a fusion protein or conjugated to an agent as described supra.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide, and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be known to those of ordinary skill in the art. Alternatively, various commercial preparations of proteins, polypeptides, and peptides are known to those of skill in the art.

VI. Nucleic Acids and Vectors

In certain aspects of the invention, nucleic acid sequences encoding a kynureninase or a fusion protein containing a kynureninase may be disclosed. Depending on which expression system is used, nucleic acid sequences can be selected based on conventional methods. For example, if the kynureninase is derived from human kynureninase and contains multiple codons that are rarely utilized in *E. coli*, then that may interfere with expression. Therefore, the respective genes or variants thereof may be codon optimized for *E. coli* expression. Various vectors may be also used to express the protein of interest. Exemplary vectors include, but are not limited, plasmid vectors, viral vectors, transposon, or liposome-based vectors.

VII. Host Cells

Host cells may be any that may be transformed to allow the expression and secretion of kynureninase and conjugates thereof. The host cells may be bacteria, mammalian cells, yeast, or filamentous fungi. Various bacteria include *Escherichia* and *Bacillus*. Yeasts belonging to the genera *Saccharomyces, Kiuyveromyces, Hansenula*, or *Pichia* would find use as an appropriate host cell. Various species of filamentous fungi may be used as expression hosts, including the following genera: *Aspergillus, Trichoderma, Neurospora, Penicillium, Cephalosporium, Achlya, Podospora, Endothia, Mucor, Cochliobolus*, and Pyricularia.

Examples of usable host organisms include bacteria, e.g., *Escherichia coli* MC1061, derivatives of *Bacillus subtilis* BRB1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) or *Schizosaccharomyces pombe*; and filamentous fungi, e.g., *Aspergillus nidulans, Aspergillus awamori* (Ward, 1989), or *Trichoderma reesei* (Penttila et al., 1987; Harkki et al., 1989).

Examples of mammalian host cells include Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCCRL 1548), SV40-transformed monkey kidney cells (COS-1; ATCC CRL 1650), and murine embryonic cells (NIH-3T3; ATCC CRL 1658). The foregoing being illustrative but not limitative of the many possible host organisms known in the art. In principle, all hosts capable of secretion can be used whether prokaryotic or eukaryotic.

Mammalian host cells expressing the kynureninase and/or their fusion proteins are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum. Culture conditions are also standard, e.g., cultures are incubated at 37° C. in stationary or roller cultures until desired levels of the proteins are achieved.

VIII. Protein Purification

Protein purification techniques are well known to those of skill in the art. These techniques involve, at one level, the homogenization and crude fractionation of the cells, tissue, or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by centrifugation; chromatography steps, such as ion exchange, gel filtration, reverse phase, hydroxyapatite, and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, a kynureninase, a fusion protein containing a kynureninase, or a modified kynureninase post PEGylation. For example, a His tag or an affinity epitope may be comprised in such a kynureninase to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

IX. Pharmaceutical Compositions

It is contemplated that the novel kynureninase can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more kynureninase or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one kyureninase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of a the composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semisolid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition that includes kynureninases, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the kynureninase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

X. Combination Treatments

In certain embodiments, the compositions and methods of the present embodiments involve administration of a kynureninase in combination with a second or additional therapy. Such therapy can be applied in the treatment of any disease that is associated with kynurenine dependency. For example, the disease may be cancer.

The methods and compositions, including combination therapies, enhance the therapeutic or protective effect, and/ or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a kynureninase and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a kynureninase or an anti-cancer agent), or by exposing the tissue, tumor, and/or cell with two or more distinct compositions or formulations, wherein one composition provides 1) a kynureninase, 2) an anti-cancer agent, or 3) both a kynureninase and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A kynureninase may be administered before, during, after, or in various combinations relative to an anti-cancer treatment. The administrations may be in intervals ranging from concurrently to minutes to days to weeks. In embodiments where the kynureninase is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the kynureninase and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a kynureninase is "A" and an anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. Checkpoint inhibitors, such as, for example, ipilumimab, are another such example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

XI. Kits

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a kynureninase, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes a kynureninase that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

XII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Gene Construction, Expression, and Purification of Kynureninase from *Psuedomonas fluorescens*

A gene for expression of the kynureninase enzyme from *Pseudomonas fluorescens* (Pf-KYNU) was constructed by overlap extension polymerase chain reaction (PCR) of four codon optimized gene blocks designed using DNA-Works software (Hoover and Lubkowski, 2002). The full-length gene includes an N-terminal XbaI restriction enzyme site (nucleotides 1-6), an optimized ribosome binding site (RBS; nucleotides 29-55), a start codon (nucleotides 56-58), an N-terminal His6 tag (nucleotides 59-91), an *E. coli* codon optimized Pf-KYNU gene (nucleotides 92-1336), a stop codon (nucleotides 1337-1342), and a C-terminal BamHI restriction enzyme site (nucleotides 1342-1347) (see, SEQ ID NO: 1). The aforementioned restriction enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an $OD_{600}$~1.0 was reached by adding IPTG (0.5 mM final concentration) with continued shaking overnight at 37° C. Cells were then harvested by centrifugation and re-suspended in lysis buffer consisting of 50 mM sodium phosphate, pH 7.4, 300 mM NaCl, 0.5 mM pyridoxyl phosphate (PLP), 1 mM phenylmethylsulfonylfluoride, and 1 µg/mL DNase. Lysis was achieved by French press and the lysate was cleared of particulates by centrifuging at 20,000×g for 1 h at 4° C. The supernatant was then filtered through a 5 µm syringe filter and applied to a Ni-NTA/agarose column (Qiagen) pre-equilibrated in a buffer composed of 50 mM sodium phosphate, 300 mM NaCl, and 0.1 mM PLP at pH 7.4. After loading the lysate onto the column, the resin was washed with 5 column volumes (CV) of 50 mM sodium phosphate, pH 7.4, 300 mM NaCl, and 0.1 mM PLP with 30 mM imidazole. Next, the flow rate was set to slowly wash the column overnight with 100 CV of endotoxin-free PBS (Corning) buffer with 0.1 mM PLP and 1% v/v TRITON® X114. This overnight wash removes lipopolysaccharide (LPS or endotoxin) that is a typical contaminant of bacterial expression systems. The washed enzyme was then eluted in 5 CV of endotoxin-free PBS with 0.1 mM PLP with 250 mM imidazole, and the resin was rinsed with a second 5 CV portion of endotoxin free PBS with 0.1 mM PLP. At this point, enzyme was buffer exchanged into fresh PBS to remove imidazole, 10% glycerol was added and aliquots were flash frozen in liquid nitrogen for storage at −80° C. Alternatively, enzyme was immediately buffer exchanged into freshly made, sterile 100 mM sodium phosphate, pH 8.4, to both remove imidazole and prepare it for PEGylation (see, Example 4). Enzyme purities were typically >95% based on SDS-PAGE analysis and typical yields averaged around 75 mg/L of culture. Protein quantities were assessed by measuring $Abs_{280\ nm}$ and using the calculated enzyme extinction coefficient of 63,745 $M^{-1}$ $cm^{-1}$.

Example 2—Gene Construction, Expression, and Purification of Kynureninase from *Homo sapiens*

A gene for expression of the kynureninase enzyme from *Homo sapiens* (h-KYNU) was obtained by overlap extension polymerase chain reaction (PCR) of four codon optimized gene blocks designed using DNA-Works software (Hoover and Lubkowski, 2002). The full-length gene includes an N-terminal XbaI restriction enzyme site (nucleotides 1-6), an optimized RBS (nucleotides 28-60), a start codon (nucleotides 61-63), an N-terminal His6 tag (nucleotides 64-96), an *E. coli* codon optimized h-KYNU gene (nucleotides 97-1488), a stop codon (nucleotides 1489-1491), and a C-terminal BamHI restriction enzyme site (nucleotides 1492-1497) (see, SEQ ID NO: 2). The aforementioned restriction enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an $OD_{600}$~1.0 was reached by adding IPTG (0.5 mM final concentration) with continued shaking overnight at 37° C. Cells were then harvested by centrifugation and re-suspended in lysis buffer consisting of 50 mM sodium phosphate, pH 7.4, 300 mM NaCl, 0.5 mM pyridoxyl phosphate (PLP), 1 mM phenyl-methylsulfonylfluoride, and 1 µg/mL DNase. Lysis was achieved by French press and the lysate was cleared of particulates by centrifuging at 20,000×g for 1 h at 4° C. The supernatant was then filtered through a 5 µm syringe filter and applied to a Ni-NTA/agarose column (Qiagen) pre-equilibrated in 50 mM sodium phosphate, pH 7.4, 300 mM NaCl, and 0.1 mM PLP buffer. After loading the lysate onto the column, the resin was washed with 5 column volumes (CV) of 50 mM sodium phosphate, pH 7.4, 300 mM NaCl, and 0.1 mM PLP with 30 mM imidazole. Next, the flow rate was set to slowly wash the column overnight with 100 CV of endotoxin-free PBS (Corning) buffer with 0.1 mM PLP and 1% v/v TRITON® X114. This overnight wash removes lipopolysaccharide (LPS or endotoxin) that is a typical contaminant in bacterial expression of enzymes. The washed enzyme was then eluted in 5 CV of endotoxin free PBS with 0.1 mM PLP with 250 mM imidazole and the resin was rinsed with a second 5 CV portions of endotoxin free PBS with 0.1 mM PLP. At this point, enzyme was buffer exchanged into fresh PBS to remove imidazole, 10% glyc-erol was added and aliquots were flash frozen in liquid nitrogen for storage at –80° C. Alternatively, enzyme could be buffer exchanged into freshly made, sterile 100 mM sodium phosphate, pH 8.4, to both remove imidazole and prepare it for PEGylation (see, Example 4). Enzyme purities were typically >95% as assessed by SDS-PAGE analysis and typical yields averaged around 20 mg/L of liquid culture. Protein quantities were assessed by measuring $Abs_{280\ nm}$ and using the calculated enzyme extinction coef-ficient of 76,040 $M^{-1}$ $cm^{-1}$.

Example 3—Gene Construction, Expression, and Purification of Kynureninase from *Mus musculus*

A gene for expression of the kynureninase enzyme from *Mus musculus* (m-KYNU) was obtained by overlap exten-sion polymerase chain reaction (PCR) of three codon opti-mized gene blocks designed using DNA-Works software (Hoover et al., 2002). The full-length gene included an N-terminal XbaI restriction enzyme site (nucleotides 1-6), an optimized RBS (nucleotides 29-58), a start codon (nucleotides 59-61), an N-terminal His6 tag (nucleotides 62-94), an *E. coli* codon optimized m-KYNU gene (nucleo-tides 95-1483), a stop codon (nucleotides 1484-1486), and a C-terminal BamHI restriction enzyme site (nucleotides 1487-1492) (see, SEQ ID NO: 3). The aforementioned restriction enzyme sites were used to clone the assembled gene into a pET-28a+ vector (Novagen). This construct was then used to transform BL21 (DE3) *E. coli* for expression. Cells were grown at 37° C. shaking at 210 rpm in Terrific Broth (TB) media with 50 mg/L of kanamycin. Expression was induced when an $OD_{600}$~1.0 was reached by adding 0.5 mM IPTG and continued overnight at 37° C. Cells were harvested by centrifugation and re-suspended in lysis buffer consisting of 50 mM sodium phosphate, pH 7.4, 300 mM NaCl, 0.5 mM pyridoxyl phosphate (PLP), 1 mM phenyl-methylsulfonylfluoride, and 1 µg/mL DNase. Lysis was achieved by French press and the lysate cleared of particu-lates by centrifuging at 20,000×g for 1 h at 4° C. The supernatant was filtered through a 5 µm syringe filter and applied to a Ni-NTA/agarose column (Qiagen) pre-equili-brated in 50 mM sodium phosphate, pH 7.4, 300 mM NaCl, and 0.1 mM PLP buffer. After loading the lysate onto the column, the resin was washed with 5 column volumes (CV) of 50 mM sodium phosphate, pH 7.4, 300 mM NaCl, and 0.1 mM PLP with 30 mM imidazole. Next the flow rate was set to slowly wash overnight with 100 CV of endotoxin-free PBS (Corning) buffer with 0.1 mM PLP and 1% v/v TRI-TON® X114. This overnight wash removeD lipopolysac-charide (LPS or endotoxin) that is a typical contaminant in bacterial expression of enzymes. The washed enzyme was eluted in 5 CV of endotoxin-free PBS with 0.1 mM PLP with 250 mM imidazole and the resin rinsed with a second 5 CV portion of endotoxin-free PBS with 0.1 mM PLP. At this point, enzyme was buffer exchanged into fresh PBS to remove imidazole, 10% glycerol added and aliquots flash frozen in liquid nitrogen for storage at –80° C.

Example 4—Pharmacological Preparation of Kynureninase from *Pseudomonas fluorescens*

To improve the circulation time of the enzyme in vivo, the hydrodynamic radius of KYNU enzymes was increased by functionalizing surface reactive groups in the protein by conjugation to PEG. In one embodiment, Pf-KYNU was functionalized by reaction of surface lysine residues with Methoxyl PEG Succinimidyl Carbonate 5000 MW (NANOCS). The purified, endotoxin-free enzyme was thor-oughly buffer exchanged into freshly prepared 100 mM sodium phosphate, pH 8.4, and concentrated to 10 mg/mL. The resulting solution was added directly to a 100:1 molar excess of solid PEG reagent and allowed to react at room temperature for 1 h (FIG. 1). Un-reacted PEG was removed from solution by thorough buffer exchange into fresh, endo-toxin-free PBS in a 100 kDa cut off centrifugal filtration device (AMICON®). The apparent molecular mass of the enzyme was then checked on a size exclusion HPLC column (Phenomenex) in PBS. A MW standard solution from Bio-Rad was used to generate a standard curve and enzyme retention times compared to those of the protein standards. Based on the standard curve, the non-PEGylated enzyme has an apparent mass of 40 kDa, which is close to that of the mass of one monomer of Pf-KYNU. The PEGylated version of the enzyme was seen to have an apparent mass of 1,300 kDa, i.e. substantially larger than the unmodified enzyme. Endotoxin levels were quantified using the Chromo-LAL kinetic chromogenic endotoxin testing kit (Associates of Cape Cod, Inc.). Enzyme washed in the manner described above typically resulted in endotoxin levels 0.19±0.07 EU/mg of purified Pf-KYNU.

Example 5—Pharmacological Preparation of Kynureninase from *Homo sapiens*

To improve circulatory residence time of the human enzyme in vivo, the hydrodynamic radius of h-KYNU was increased by functionalizing surface reactive groups in the protein by conjugation to PEG. In one embodiment, h-KYNU was functionalized by reaction of surface lysine residues with Methoxyl PEG Succinimidyl Carbonate 5000 MW (NANOCS). The purified, endotoxin-free enzyme was thoroughly buffer exchanged into freshly prepared 100 mM sodium phosphate, pH 8.4, and concentrated to 10 mg/mL. The resulting solution was added directly to a 100:1 molar excess of solid PEG reagent and allowed to react at room temperature for 1 h. Un-reacted PEG was removed from solution by thorough buffer exchange into fresh, endotoxin-free PBS in a 100 kDa cut off centrifugal filtration device (AMICON®). The apparent molecular mass of the enzyme was determined using a size exclusion HPLC column (Phenomenex) equilibrated with PBS and retention times compared to a MW standard solution (BioRad). Endotoxin levels were quantified using the Chromo-LAL kinetic chromogenic endotoxin testing kit (Associates of Cape Cod, Inc.).

Example 6—Assay for Measuring Kinetic Parameters of Kynureninase

The kinetic parameters of Pf-KYNU and h-KYNU, as well as of their PEGylated versions as described in Examples 4 and 5, were quantified by a spectrophotometric assay, in which the decay in the maximum absorbance of the enzyme substrate, L-kynurenine, was monitored as a function of time. L-kynurenine solutions were prepared in a PBS buffer, pH 7.4, to result in final concentrations ranging from 8 $\mu$M to 250 $\mu$M. L-Kynurenine has an extinction coefficient of 4,500 $M^{-1}$ $cm^{-1}$ with a max at 365 nm while the products of the kynureninase reaction, L-anthranilic acid and L-alanine, do not appreciably absorb at 365 nm. Reactions were initiated by adding and rapidly mixing enzyme solutions ($\sim$20 nM final) with the substrate solutions and monitoring the loss of substrate KYN at 25° C. by measuring $Abs_{365}$ nm over time. The resulting data was processed and fitted to the Michaelis-Menten equation for determining kinetic constants. The kinetics of PEGylated Pf-KYNU enzyme was measured in an identical manner. For the non-PEGylated enzyme, $k_{cat}/K_M=1.0\times10^5$ $M^{-1}s^{-1}$, and for the PEGylated form, $k_{cat}/K_M=1.3\times10^5$ $M^{-1}s^{-1}$. Kinetic parameters for the hydrolysis of 3-hydroxy-L-kynurenic acid were also determined as described here.

Example 7—In Vitro Stability of Kynureninase

Figure 2:
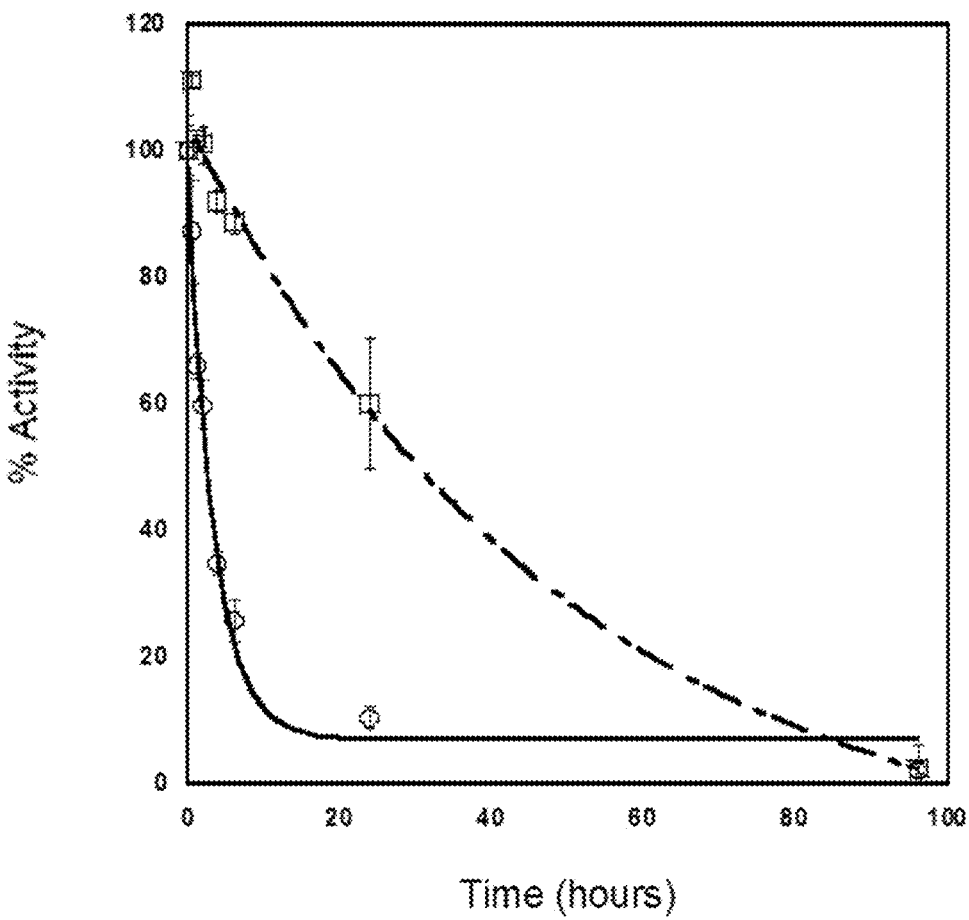
FIG. 2—Stability of Pf-KYNU in (open square) PBS and (open circle) pooled human serum.

To measure the in vitro stability of Pf-KYNU, the enzyme was added to either PBS buffer or pooled human serum to a final concentration of 10 $\mu$M and incubated at 37° C. Portions of 10 $\mu$L each were taken out at time points and added to 990 $\mu$L of a 250 $\mu$M solution of L-kynurenine/PBS. The initial rate of reaction was monitored by measuring the decay of absorbance at 365 nm over time as described in Example 3. Enzyme stability was determined by comparing the initial rate of L-kynurenine catalysis at each time point and comparing it to the rate at time=0. The resulting data was plotted as % activity vs. time and fitted to an exponential equation to determine the half-life ($T_{1/2}$). The Pf-KYNU enzyme was found to have a $T_{1/2}=34.3$ hours in PBS and a $T_{1/2}=2.4$ hours in pooled human serum (FIG. 2).

Example 8— Assay for Quantifying Kynurenine and Tryptophan Levels In Vivo

In vivo levels of L-kynurenine, tryptophan, kynureninic acid, 3-hydroxy-L-kynurenine and L-anthranlilic acid (one of the products of kynureninase catalysis) were quantified and monitored by HPLC. Upon necropsy of the mice, samples of blood, the tumor, the spleen, and the liver were removed. Blood samples were centrifuged to separate whole blood from serum. Tissue samples were first homogenized, and then centrifuged to remove the solid portion. To each liquid portion was added a 1:10 v/v portion of 100% trichloroacetic acid to precipitate macromolecules. Solids were again removed by centrifuging and the supernatants were passed through a 0.45 $\mu$m syringe filter. The treated supernatants were applied directly to a HPLC (Shimadzu) and separated on a standard analytical C-18 column using a gradient starting from 0% solution B to 100% solution B where solution A is $H_2O+0.1\%$ trifluoroacetic acid and solution B is acetonitrile+0.1% trifluoroacetic acid. The full absorbance range from 190 nm to 900 nm was continually collected to monitor all possible molecules and fluorescence spectroscopy (Ex=365 nm, Em=480 nm) was simultaneously collected to specifically monitor kynurenine levels. Concentrations and retention times were determined using standard solutions made from the pure molecules (Sigma).

Figure 3:
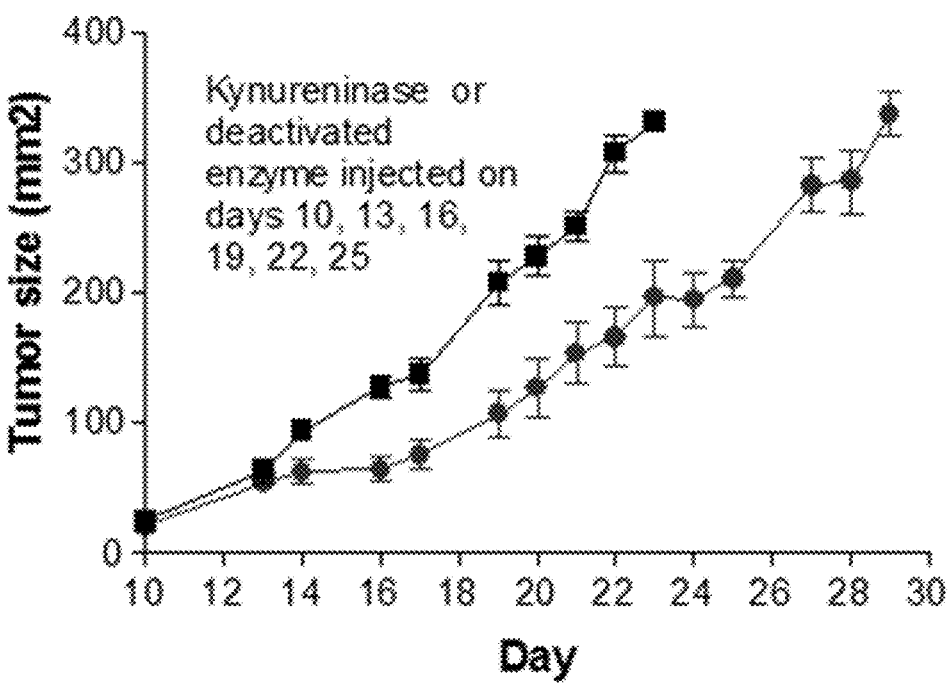
FIG. 3—Efficacy of PEG-Pf-KYNU in an autologous B16 mouse melanoma model as measured by tumor growth rates. (Solid square) Heat inactivated PEG-Pf-KYNU. (Solid circle) Active PEG-Pf-KYNU.
Figure 4:
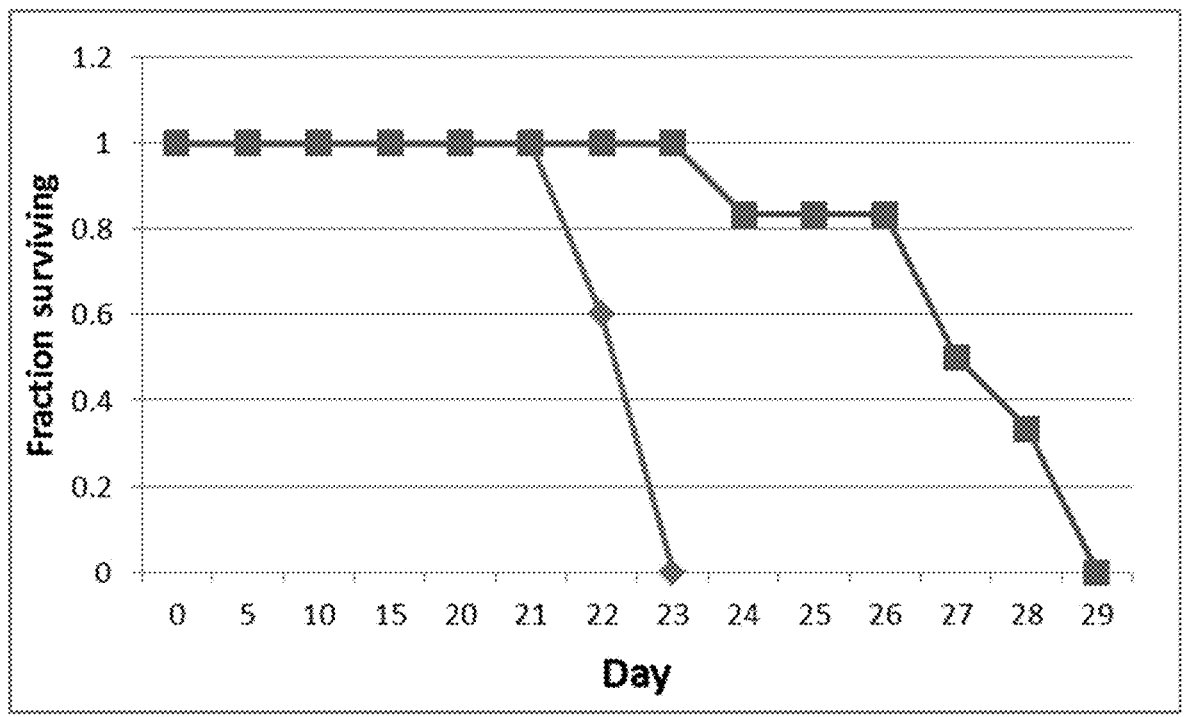
FIG. 4—Efficacy of PEG-Pf-KYNU in an autologous B16 mouse melanoma model as measured by survival. (Solid diamond) Heat inactivated PEG-Pf-KYNU. (Solid square) Active PEG-Pf-KYNU.
Figures 5A, 5B:
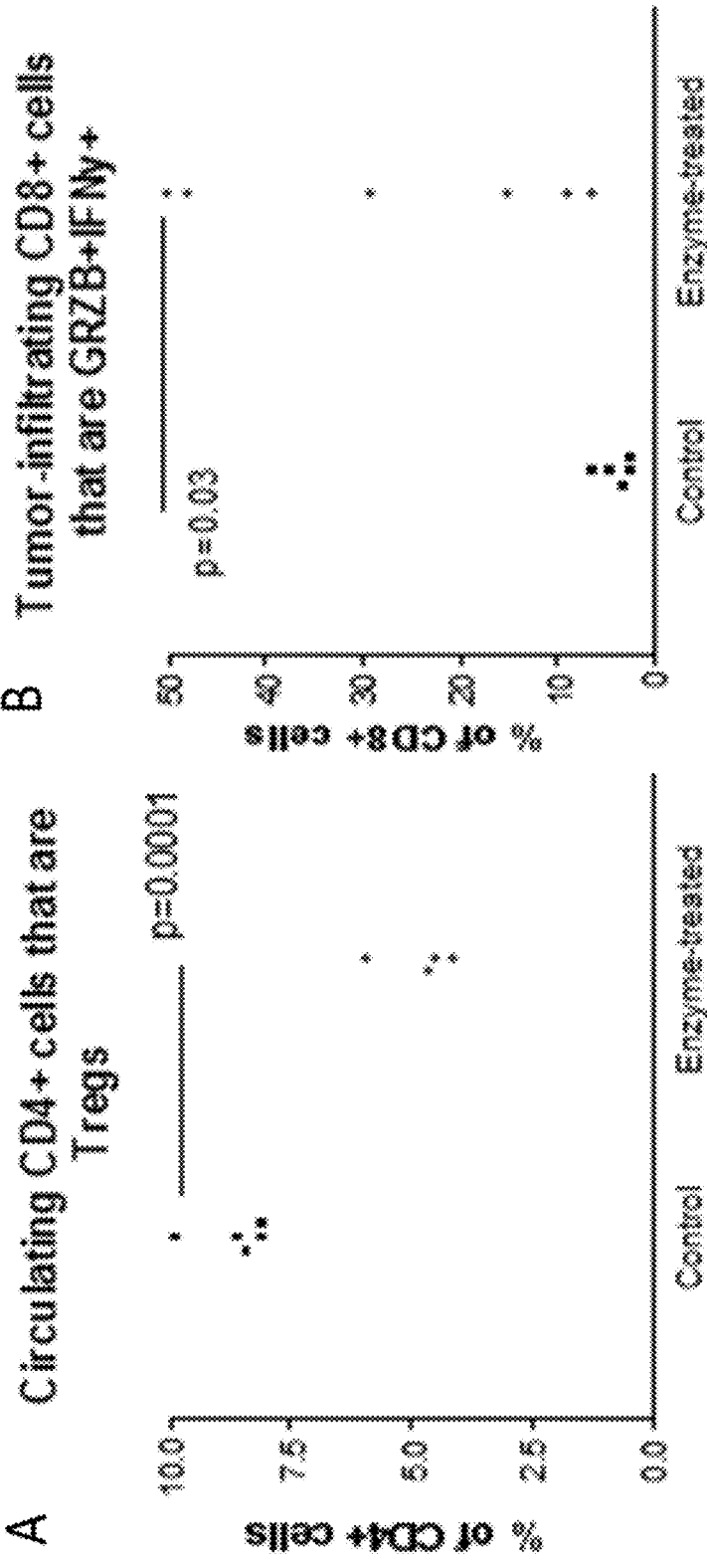
FIGS. 5A-5B—Mice treated with heat-inactivated PEG-Pf-KYNU (solid squares). Mice treated with active PEG-Pf-KYNU (solid diamonds).

Example 9—Efficacy of PEG-Pf-KYNU in the Autologous B16 Mouse Melanoma Model B6-WT mice (n=20) were each inoculated with $2.5\times10^5$ B16 murine melanoma cells by subcutaneous flank injection. After allowing tumors to establish for 10 days (tumor mean=20 $mm^2$) the mice were split into two groups of n=10 each. The control group was then treated with 20 mg/kg of heat inactivated PEG-Pf-KYNU by intra-tumoral injection every three days until tumors reached 350 $mm^2$ in size. The experimental group was treated in an identical manner except with 20 mg/kg of active PEG-Pf-KYNU by intra-tumoral injection every three days until tumors reached an endpoint of 350 $mm^2$ in size. The growth rates of B16 melanoma tumors was significantly retarded in the treatment group administered active PEG-Pf-KYNU compared to the identically treated heat-inactivated PEG-Pf-KYNU group (FIG. 3) resulting in a significant life-span extension (FIG. 4). Lymphocytes isolated from control and experimental treatment groups were assessed with panels of antibodies (i.e., anti-CD45, CD4, Nk1.1, CD25, FoxP3, CD8, granzyme B, IFN$\gamma$, CTLA4, CD11c, CD11b, F4/80, GR-1, and Ly6-C) which revealed that the population of circulating CD4+CD25+FoxP3+ regulatory T-cells was significantly lower in the group treated with active PEG-Pf-KYNU (4.8±0.8% vs. 8.6±0.8%). In addition, the population of tumor infiltrating CD8+ T-cells expressing granzyme B and interferon $\gamma$ was significantly higher in mice treated with active enzyme (26±19% vs. 4±2%) (FIGS. 5A-B).

Example 10—Kynureninase-scFv Fusion Proteins for Tumor Targeting

In some aspects, the present invention also contemplates polypeptides comprising the modified bacterial or mammalian kynureninase linked to a heterologous amino acid sequence. For example, the native or modified kynureninase may be linked to a single-chain variable fragment (scFv) antibody that binds specific cell surface tumor antigens. In this embodiment an scFv-kynureninase fusion protein with the scFv portion of the protein having specific affinity for a known tumor antigen, preferably a tumor specific antigen that internalizes at a slower rate, e.g., MUC-1, would allow the kynureninase portion of the fusion protein to be delivered to the tumor cell and degrade KYN. One example would be a scFv-kynureninase fusion protein where the scFv portion targets and binds to the human epidermal growth factor receptor 2 (HER2) that is upregulated in certain types of breast cancer.

In this embodiment a native or modified kynureninase-anti-HER2-scFV fusion protein would act to target and concentrate kynureninase directly to the tumor surface and act to degrade tumor-produced KYN.

Example 11—Kynureninase-Anti-CTLA4-scFv Fusion Proteins

In some aspects, the present invention also contemplates polypeptides comprising the modified bacterial or mammalian kynureninase linked to a heterologous amino acid sequence. For example, the native or modified kynureninase may be linked to a single-chain variable fragment (scFv) antibody that binds the Cytotoxic T-Lymphocyte Antigen 4 (CTLA-4) receptor, Programmed Cell Death 1 (PD-1), or Programmed Cell Death Ligand 1 (PD-L1). A blockade of CTLA-4, PD-1, or PD-L1 by an antagonizing antibody or antibody fragment allows the inhibitory T-cell signal to be reversed allowing CD28 to stimulate T-cell activation. In this embodiment a native or modified kynureninase-anti-CTLA4-, anti-PD-1-, or anti-PD-L1-scFv fusion protein would act to remove both inhibitory protein:protein interaction signaling and inhibitory kynurenine signaling. This embodiment of a native or modified kynureninase-scFv fusion protein would be expected to potently upregulate T-cell activation and promote robust anti-tumoral responses.

Example 12—Chimeric Antigen Receptor Constructs for Delivery of Kynureninase to T Cells In some aspects, the present invention also contemplates a lentiviral vector suitable for transfection of T cells with chimeric antigen receptor (CAR) constructs such that a modified bacterial or mammalian kynureninase would be co-expressed in addition to the CAR construct. CAR constructs are proteins containing an extracellular antigen binding domain fused to a transmembrane and cytoplasmic signaling domain from a CD3-t chain and often a CD28 molecule (Ahmed et al., 2010). The antigen binding domain may be an scFv designed to bind an antigen expressed by a tumor cell with examples being HER2 expressed by glioblastoma or osteosarcoma, CD19 or CD20 expressed by various B-cell malignancies, or GD2 expressed by neuroblastoma (Lipowska-Bhalla et al., 2012) or any other relevant target. In this embodiment the lentiviral vector, delivering an appropriate CAR construct to a T cell, would in addition co-express a native or modified bacterial or mammalian kynureninase in the cytosol. The T cell containing this CAR/kynureninase construct would have the dual ability to 1) bind to specific tumor cells and 2) to degrade KYN, preventing KYN induction of a regulatory phenotype and or apoptosis. In another embodiment a T cell would express a CAR construct that binds a CD19+ or CD20+ diffuse large B-cell lymphoma while co-expressing a kynureninase to degrade the high concentrations of KYN often produced by this tumor type (Yoshikawa et al., 2010; de Jong et al., 2011; Yao et al., 2011).

Example 13—Genetic Selection for Kynureninase Activity

The amino acid L-tryptophan (L-Trp) is synthesized from the pentose derived precursor, chorismate, by expression of the trp biosynthetic genes. In bacteria such as *E. coli* the trp biosynthetic genes are organized in an operon composed of five genes; trpE, trpD, trpC, trpB, and trpA. The TrpE and TrpD proteins are components of the anthranilate synthase complex that catalyzes the first step in the conversion of chorismate and L-glutamine to anthranilic acid and L-glutamate. Anthranilic acid is then subsequently converted to L-Trp by the action of TrpC, TrpA, and TrpB. Cells lacking a functional anthranilate synthase gene are auxotrophic for L-Trp and cannot grow in minimal media without tryptophan. The inventors postulated that since kynurenine can be transported into the cytosol of many organisms, cells expressing recombinant L-kynureninase enzymes displaying a sufficiently high catalytic activity should be able to convert cytosolic L-kynurenine to anthranilic acid and the latter then enables the synthesis of L-Trp. By contrast, cells that do not express the enzyme or express variants with low catalytic activity should display either no growth or very slow growth, respectively, on minimal media with L-kynurenine.

Figure 6:
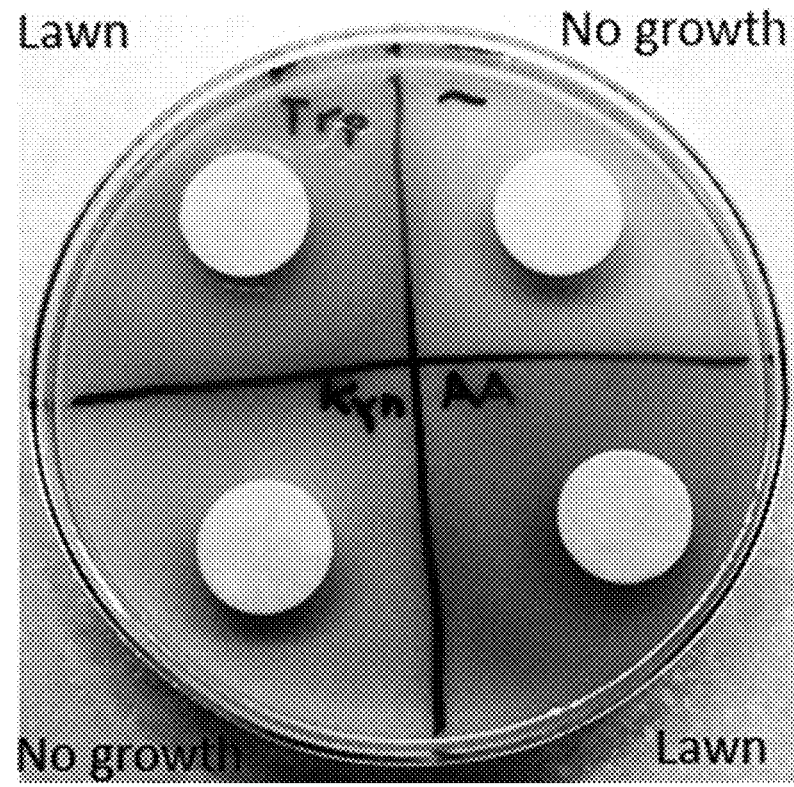
FIG. 6— Genetic selection for kynureninase activity in *E. coli*. *E. coli*-ΔtrpE cells plated on M9 minimal media plates with filter paper disks soaked in L-Trp (Trp), buffer (−), anthranilic acid (AA), or L-Kyn (Kyn).

*E. coli* trpE and trpD deletion mutants were obtained from Genetic Resources at Yale CGSC. Strain genotypes were (F—,Δ(araD-araB)567, ΔlacZ4787(::rrnB-3), λ-, ΔtrpE772::kan, rph-1, Δ(rhaD-rhaB)568, hsdR514) and (F—, Δ(araD-araB)567, ΔlacZ4787(::rrnB-3),λ-,ΔtrpD771::kan, rph-1, Δ(rhaD-rhaB)568, hsdR514), respectively. Cells were plated on M9 minimal media plates. Filter paper disks soaked in either L-Trp, L-Kyn, anthranilic acid, or buffer were then placed on the plates followed by incubation at 37° C. *E. coli*-ΔtrpD cells only grew in the presence of L-Trp, however *E. coli*-ΔtrpE could also grow in the presence of anthranilic acid but not buffer or L-Kyn, demonstrating that trpC, trpA, and trpB were expressed, allowing rescue of the L-Trp auxotrophy with anthranilic acid as an intermediate metabolite (FIG. 6). Furthermore, *E. coli*-ΔtrpE cells transformed with a plasmid harboring the Pf-KYNU gene grew robustly on M9 minimal media plates in the presence of L-Kyn.

Example 14—Gene Construction, Expression and Purification of Bacterial Kynureninases Displaying High Catalytic Activity Towards Kynurenine and Identity to the Human Kynureninase Similar to other eukaryotic kynureninases the *Homo sapiens* enzyme is highly selective towards the hydrolysis of 3'-OH kynurenine and has about 1,000-fold lower catalytic activity towards kynurenine. Because of its poor catalytic activity towards kynurenine, the human enzyme is not suitable for therapeutic purposes. Administration of PEGylated Pf-KYNU (Example 9), Mu-KYNU (Example 22 and Example 23), or Cp-KYNU (Example 17) (all of which display high catalytic activity towards kynurenine instead of 3'-OH kynurenine) resulted in tumor growth retardation as shown in Example 9 (FIG. 3). However, administration of PEGylated human kynureninase at similar or higher dosing had no effect on the growth of B16 melanoma tumors (n=4). However, as shown in Example 20, engineering of h-KYNU can improve the L-kynurenine degrading activity of the human enzyme. Such engineered h-KYNU variants may result in tumor growth retardation as seen with PEGylated Pf-KYNU (Example 9), Mu-KYNU (Example 22 and Example 23), and Cp-KYNU (Example 17).

The Pf-KYNU displays low sequence identity to its human counterpart (24% amino acid identity). Due to its low sequence identity to the human protein, Pf-KYNU may elicit adverse immune responses in patients as well as the production of neutralizing antibodies. Therefore it is important to discover kynureninase enzymes that display high catalytic activity and selectivity towards kynurenine and have a higher degree of amino acid identity to the *Homo sapiens* kynureninase. The inventors identified a number of bacterial enzymes that display >38% amino acid identity to the *Homo sapiens* kynureninase and also high kynurenine hydrolysis activity. The sequences of these enzymes are provided as SEQ ID NOs: 13-52. The percent identities of these enzymes as compared to *Homo sapiens* kynureninase are provided in Table 1. As a representative example, a gene for expression of the kynureninase enzyme from *Mucilaginibacter paludis* (Mu-KYNU) (SEQ ID NO: 33) was constructed by overlap extension polymerase chain reaction (PCR) of two codon optimized gene blocks designed using the DNA-Works software (Hoover and Lubkowski, 2002). The full-length gene includes an N-terminal NcoI restriction enzyme site, an optimized RBS, an N-terminal His6 tag, E. coli codon optimized Mu-KYNU gene, a stop codon and a C-terminal EcoRI restriction enzyme site. The aforementioned restriction enzyme sites were used to clone the assembled gene into a pET-28a+ vector (Novagen). This construct was then used to transform BL21 (DE3) E. coli for expression. Cells were grown at 37° C. with shaking at 210 rpm in Terrific Broth (TB) media with 50 mg/L of kanamycin. Expression was induced when an $OD_{600}$~1.0 was reached by adding IPTG (0.5 mM final concentration) with continued shaking overnight at 37° C. Cells were then harvested by centrifugation and re-suspended in lysis buffer consisting of 50 mM sodium phosphate, pH 7.4, 300 mM NaCl, 0.5 mM pyridoxyl phosphate (PLP), 1 mM phenylmethylsulfonylfluoride, and 1 μg/mL DNase. Lysis was achieved by French press and the lysate was cleared of particulates by centrifuging at 20,000×g for 1 h at 4° C. The supernatant was then filtered through a 5 μm syringe filter and applied to a Ni-NTA/agarose column (Qiagen) pre-equilibrated in 50 mM sodium phosphate, pH 7.4, 300 mM NaCl, and 0.1 mM PLP buffer. After loading the lysate onto the column, the resin was washed with 5 column volumes (CV) of 50 mM sodium phosphate, pH 7.4, 300 mM NaCl, and 0.1 mM PLP with 30 mM imidazole. The washed enzyme was then eluted in 5 CV of PBS with 0.1 mM PLP with 250 mM imidazole. At this point, enzyme was buffer exchanged into fresh PBS to remove imidazole, 10% glycerol was added and aliquots were flash frozen in liquid nitrogen for storage at –80° C. Enzyme purities were typically >95% based on SDS-PAGE analysis and typical yields averaged around 75 mg/L of culture. Protein quantities were assessed by measuring $Abs_{280}$ nm and using the calculated enzyme extinction coefficient of 78,185 $M^{-1}$ $cm^{-1}$.

TABLE 1

Percent identities of eubacterial kynureninase enzymes as compared to *Homo sapiens* kynureninase.

| Species | SEQ ID NO | % Identity |
|---|---|---|
| *Arenitalea lutea* | 13 | 44.1 |
| *Belliella baitica* DSM 15883 | 14 | 43.3 |
| *Bizionia argentinensis* | 15 | 42.9 |
| *Candidatus Entotheonella* sp. TSY2 | 16 | 44.9 |
| *Candidatus Koribacter versatilis* Ellin345 | 17 | 43.3 |
| *Cecembia lonarensis* | 18 | 45.1 |
| *Chlamydia pecorum* PV3056/3 | 19 | 38.2 |
| *Chlamydophila caviae* GPIC | 20 | 40.8 |
| *Corallococcus coralloides* DSM 2259 | 21 | 43 |
| *Cyclobacterium marinum* DSM 74 | 22 | 44.5 |
| *Cystobacter fuscus* | 23 | 43.5 |
| *Echinicola vietnamensis* DSM 17526 | 24 | 44.5 |
| *Flavobacteria bacterium* BBFL7 | 25 | 43.4 |
| *Flexibacter litoralis* DSM 6794 | 26 | 47.5 |
| *Formosa* sp. AK20 | 27 | 45.7 |
| *Fulvivirga imtechensis* | 28 | 47.1 |
| *Kangiella aquimarina* | 29 | 44.1 |
| *Kangiella koreensis* DSM 16069 | 30 | 44.3 |
| *Lacinutrix* sp. 5H-3-7-4 | 31 | 44.2 |
| *Mariniradius saccharolyticus* | 32 | 44.5 |
| *Mucilaginibacter paludis* | 33 | 43.9 |
| *Myroides odoratimimus* | 34 | 42.2 |
| *Myxococcus fulvus* HW-1 | 35 | 44.5 |
| *Myxococcus stipitatus* DSM 14675 | 36 | 44.4 |
| *Myxococcus xanthus* DK 1622 | 37 | 45.1 |
| *Nafulsella turpanensis* | 38 | 48.2 |
| *Niastella koreensis* GR20-10 | 39 | 44.8 |
| *Nonlabens dokdonensis* DSW-6 | 40 | 44 |
| *Pedobacter agri* | 41 | 44.1 |
| *Pedobacter* sp. BAL39 | 42 | 42.1 |

TABLE 1-continued

Percent identities of eubacterial kynureninase enzymes as compared to *Homo sapiens* kynureninase.

| Species | SEQ ID NO | % Identity |
|---|---|---|
| *Pedobacter* sp. V48 | 43 | 44.1 |
| *Rhodonellum psychrophilum* | 44 | 45.4 |
| *Salinispora arenicola* | 45 | 39.1 |
| *Saprospira grandis* str. Lewin | 46 | 43.2 |
| *Stigmatella aurantiaca* DW4/3-1 | 47 | 42.5 |
| *Xanthomonas axonopodis* | 48 | 42 |
| *Psychroflexus gondwanensis* | 49 | 44 |
| *Lewinella cohaerens* | 50 | 45.6 |
| *Lewinella persica* | 51 | 44.9 |
| *Pontibacter roseus* | 52 | 44.8 |

Example 15—Kinetic Parameters of *Mucilaginibacter paludis* Kynureninase (Mu-KYNU)

The kinetic parameters of Mu-KYNU were quantified by a spectrophotometric assay, in which the decay in the maximum absorbance of the enzyme substrate, L-kynurenine, was monitored as a function of time. L-Kynurenine solutions were prepared in a PBS buffer, pH 7.4, to result in final concentrations ranging from 16 μM to 500 μM. L-Kynurenine has an extinction coefficient of 4,500 $M^{-1}$ $cm^{-1}$ with a $\lambda_{max}$ at 365 nm while the products of the kynureninase reaction, L-anthranilic acid and L-alanine, do not appreciably absorb at 365 nm. Reactions were initiated by adding and rapidly mixing enzyme solutions (~20 nM final concentration) with the substrate solutions and monitoring the loss of substrate at 25° C. by measuring $Abs_{365}$ nm over time. The resulting data were processed and fitted to the Michaelis-Menten equation for determining kinetic constants. Mu-KYNU was determined to have a $k_{cat}/K_M$=1.2× $10^5$ $M^{-1}s^{-1}$.

Example 16—In Vitro Stability of *Mucilaginibacter paludis* Kynureninase (Mu-KYNU)

Figure 7:
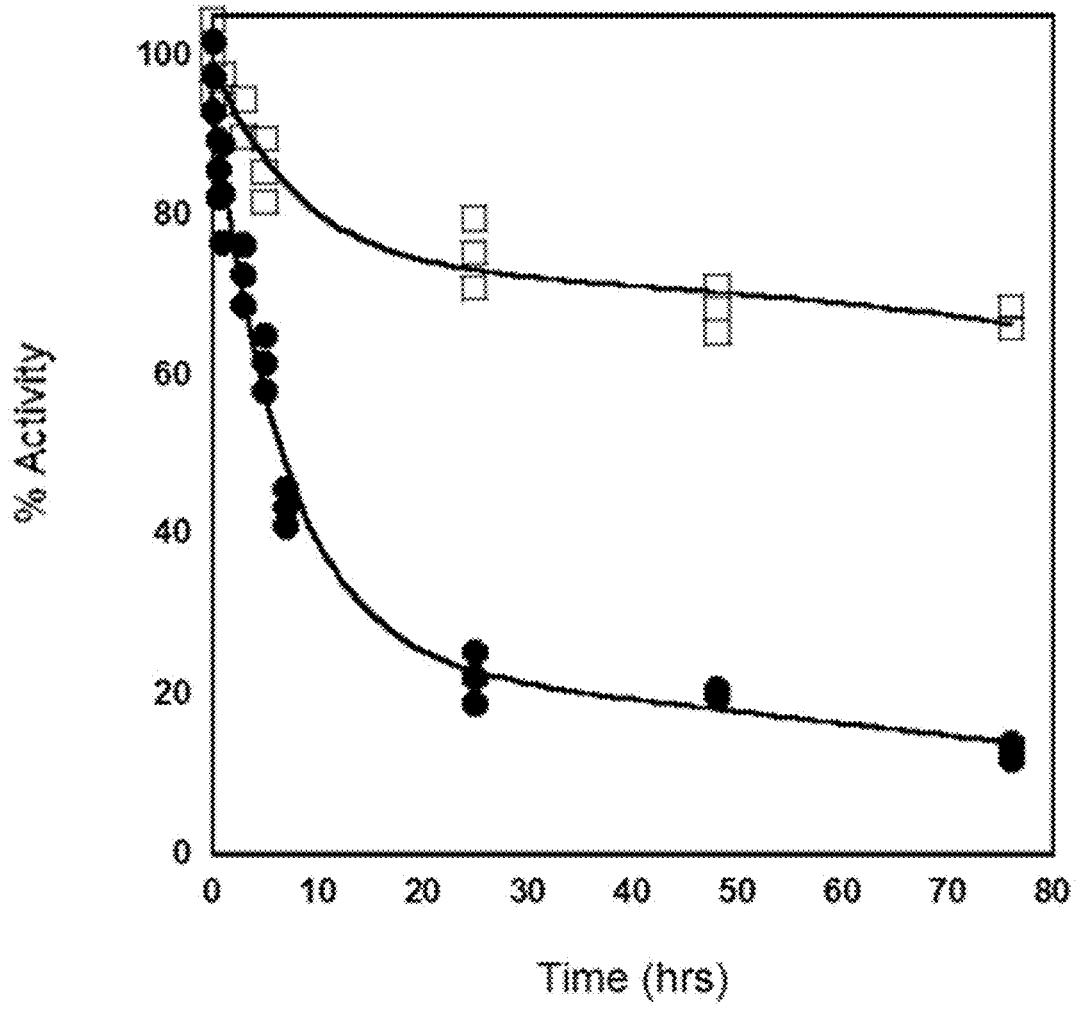
FIG. 7—In vitro stability of *Mucilaginibacter paludis* kynureninase (Mu-KYNU). Activity as a function of time of Mu-KYNU (open square) in PBS at 37° C. with a ${}^1T_{1/2}=6$ h with an amplitude of 74% remaining activity and a subsequent ${}^2T_{1/2}=150$ h, and (solid circle) in pooled human serum at 37° C. with a ${}^1T_{1/2}=5$ h with an amplitude of 30% remaining activity and a subsequent ${}^2T_{1/2}=73$ h.

To measure the in vitro stability of Mu-KYNU, the enzyme was added to either PBS buffer or pooled human serum to a final concentration of 10 μM and incubated at 37° C. Portions of 10 μL each were taken out at time points and added to 990 μL of a 250 μM solution of L-kynurenine/PBS. The initial rate of reaction was monitored by measuring the decay of absorbance at 365 nm over time as described in Example 3. Enzyme stability was determined by comparing the initial rate of L-kynurenine catalysis at each time point and comparing it to the rate at time=0. The resulting data were plotted as percent activity vs. time and fitted to a bi-phasic decay model (Stone et al., 2010) to determine the half-lives ($T_{1/2}$). The activity of Mu-KYNU enzyme in PBS was found have a $^1T_{1/2}$=6 h with an amplitude of 74% remaining activity and a subsequent $^2T_{1/2}$=150 h (FIG. 7). The stability of Mu-KYNU enzyme in pooled human serum was determined to have a $^1T_{1/2}$=5 h with an amplitude of 30% remaining activity and a subsequent $^2T_{1/2}$=73 h (FIG. 7).

Example 17—Gene Construction, Expression, and Purification of Kynureninase from *Chlamydophila pecorum*

A gene for expression of the kynureninase enzyme from *Chlamydophila pecorum* (Cp-KYNU) was synthesized using *E. coli*-codon optimized gene blocks. The full-length gene includes an N-terminal NcoI restriction enzyme site (nucleotides 1-6), a start codon (nucleotides 3-5), an N-terminal His6 tag (nucleotides 6-35), an *E. coli* codon optimized Cp-KYNU gene (nucleotides 36-1295), a stop codon (nucleotides 1296-1298), and a C-terminal EcoRI restriction enzyme site (nucleotides 1299-1304) (SEQ ID NO: 53). The aforementioned restriction enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an $OD_{600}$~1.0 was reached by adding IPTG (0.5 mM final concentration) with continued shaking overnight at 16° C. Cells were then harvested by centrifugation and re-suspended in lysis buffer consisting of 50 mM sodium phosphate, pH 7.4, 300 mM NaCl, 0.5 mM pyridoxyl phosphate (PLP), 1 mM phenylmethylsulfonylfluoride, and 1 µg/mL DNase. Lysis was achieved by French press and the lysate was cleared of particulates by centrifuging at 20,000×g for 1 h at 4° C. The supernatant was then filtered through a 5 µm syringe filter and applied to a Ni-NTA/agarose column (Qiagen) pre-equilibrated in 50 mM sodium phosphate, pH 7.4, 300 mM NaCl, and 0.1 mM PLP buffer. After loading the lysate onto the column, the resin was washed with 10 column volumes (CV) of 50 mM sodium phosphate, pH 7.4, 300 mM NaCl, and 0.1 mM PLP with 30 mM imidazole. The washed enzyme was then eluted with 5 CV of PBS containing 0.1 mM PLP and 250 mM imidazole. The eluted enzyme was buffer exchanged into fresh PBS to remove imidazole, 10% glycerol was added, and aliquots were flash frozen in liquid nitrogen for storage at −80° C.

Example 18— Kinetic Parameters of *Chlamydophila pecorum* Kynureninase (Cp-KYNU)

The kinetic parameters of Cp-KYNU (SEQ ID NO: 57) were quantified by a spectrophotometric assay, in which the decay in the maximum absorbance of the enzyme substrate, L-kynurenine, was monitored as a function of time. L-Kynurenine solutions were prepared in PBS buffer, pH 7.4, to result in final concentrations ranging from 16 µM to 500 µM. L-Kynurenine has an extinction coefficient of 4,500 $M^{-1}$ $cm^{-1}$ with a $\lambda_{max}$ at 365 nm while the products of the kynureninase reaction, anthranilate and L-alanine, do not appreciably absorb at 365 nm. Reactions were initiated by adding and rapidly mixing enzyme solutions (200 nM final concentrations) with the substrate solutions and monitoring the loss of substrate at 25° C. by measuring $Abs_{365}$ nm over time. The resulting data were processed and fitted to the Michaelis-Menten equation for determining kinetic constants. Cp-KYNU was determined to have a $k_{cat}/K_M$=3×10⁴ $M^{-1}s^{-1}$.

Example 19—Pharmacological Preparation of Kynureninase from *Mucilaginibacter paludis*

To improve the circulation time of the enzyme in vivo, the hydrodynamic radius of Mu-KYNU was increased by functionalizing surface reactive groups in the protein by conjugation to PEG. In one embodiment, Mu-KYNU was PEGylated by reaction of surface lysine residues with Methoxyl PEG Succinimidyl Carbonate 5000 MW (NANOCS). The purified Mu-KYNU, was determined to contain very low endotoxin levels (<20 EU/mg) as described below. It was thoroughly buffer exchanged into freshly prepared 100 mM sodium phosphate buffer, pH 8.4, and concentrated to greater than 1 mg/mL. The resultant solution was added directly to a 100:1 molar excess of solid PEG reagent and allowed to react at room temperature for 1 h with stirring. Un-reacted PEG was removed from solution by thorough buffer exchange into fresh, endotoxin-free PBS in a 100 kDa cutoff centrifugal filtration device (Amicon). The apparent molecular mass of the enzyme was then checked on a size exclusion HPLC column (Phenomenex) in PBS using a MW standard solution from BioRad to generate a standard curve, and enzyme retention times were compared to those of the protein standards. Endotoxin levels were quantified using the Chromo-LAL kinetic chromogenic endotoxin testing kit (Associates of Cape Cod, Inc.).

Example 20—Enhanced L-Kynurenine Degradation in an Engineered Human Kynureninase Variant The h-KYNU enzyme is highly selective towards the hydrolysis of 3'-OH kynurenine and has about 1,000 fold lower catalytic activity towards L-kynurenine. Because of its poor catalytic activity towards L-kynurenine, the wild-type human enzyme is not suitable for therapeutic purposes. To engineer improved L-kynurenine degrading activity into h-KYNU, a saturation mutagenesis library was constructed by overlap extension polymerase chain reaction (PCR) using the h-KYNU gene and a pair of oligonucleotides designed to introduce mutations of the codon corresponding to amino acid F306. F306 is located within the active site of h-KYNU where it appears to play a role in substrate binding. The F306 saturation library was screened for activity using the microtiter plate kynureninase assay of Example 6. More than a dozen clones displayed significantly higher activity than wild-type h-KYNU and were selected for further analysis. Sequencing of these clones revealed that two amino acid substitutions at position F306 resulted in increased L-kynurenine degrading activity, namely h-KYNU-F306M (SEQ ID NO: 55) and h-KYNU-F306L (SEQ ID NO: 56). These variants were then purified to homogeneity and a detailed kinetic analysis revealed a 2-fold and 5-fold increase in $k_{cat}/K_M$ for L-kynurenine for h-KYNU-F306M and h-KYNU-F306L, respectively, as compared to wild-type h-KYNU.

Figure 8:
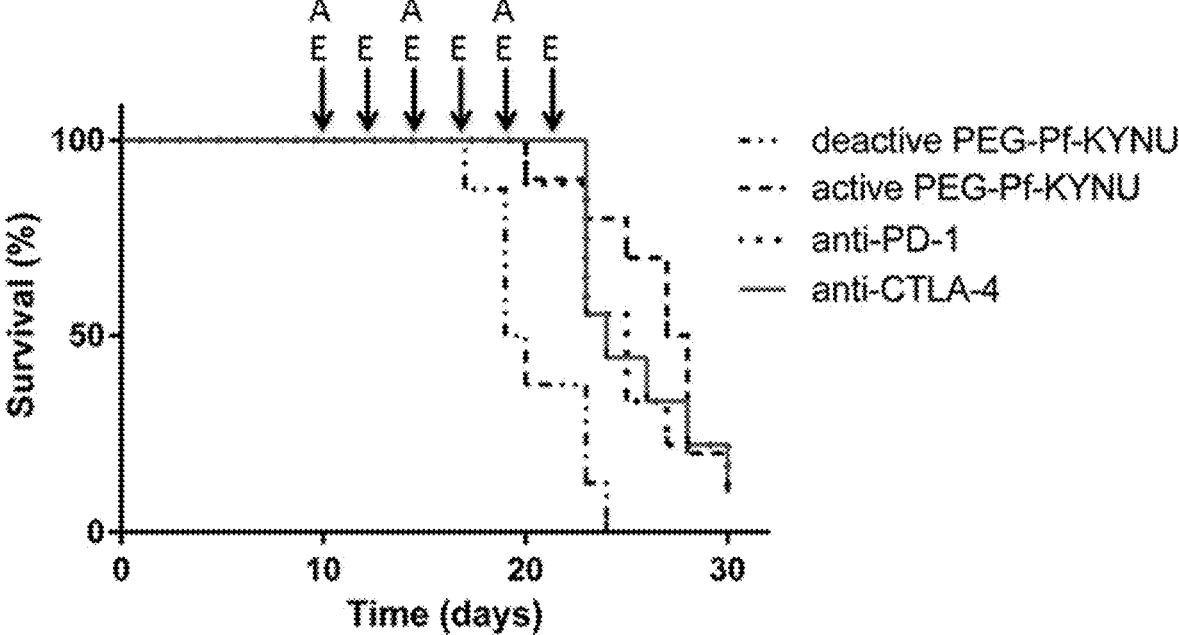
FIG. 8—Kaplan-Meier plot of B16 allografts in C57BL/6J treated with either PEG-Pf-KYNU (−−•), deactivated PEG-Pf-KYNU (−••), anti-PD1 (•••), or anti-CTLA-4 (−) Arrows indicate treatment days, (A) indicates treatment with antibody, (E) indicates treatment with enzyme.

Example 21—Comparison of Pf-KYNU, Anti-PD1, and Anti-CTLA-4 Therapies in the Autologous B16 Mouse Melanoma Model The PEGylated *Pseudomonas fluorescence* kynureninase (PEG-Pf-KYNU) was evaluated in the B16 melanoma mouse model in a side-by-side comparison with the anti-PD1 (clone RMP1-14, BioXCell #BE0146) or anti-CTLA-4 (clone UC10-4F10-11, BioXCell #BE0032) immune checkpoint inhibitor antibodies. Fifty thousand B16 cells were implanted in the flank of C57BL/6J mice (Day 0, n=8 mice each group). Once palpable tumors developed (Day 10), the animals were treated with either 250 µg anti-PD1, 100 µg anti-CTLA-4 (200 µg 1ˢᵗ dose as per Holmgaard et al. (2013)), or 500 µg of PEG-Pf-KYNU at the times shown (FIG. 8). Heat-inactivated PEG-Pf-KYNU was used as a control. Administration of PEG-Pf-KYNU resulted in significant tumor growth retardation and extended survival in a manner indistinguishable from that observed with the anti-PD1 or anti-CTLA-4 checkpoint inhibitor antibodies (FIG. 8) for PEG-Pf-KYNU vs. inactivated enzyme or PBS only.

Figures 9A, 9B, 9C:
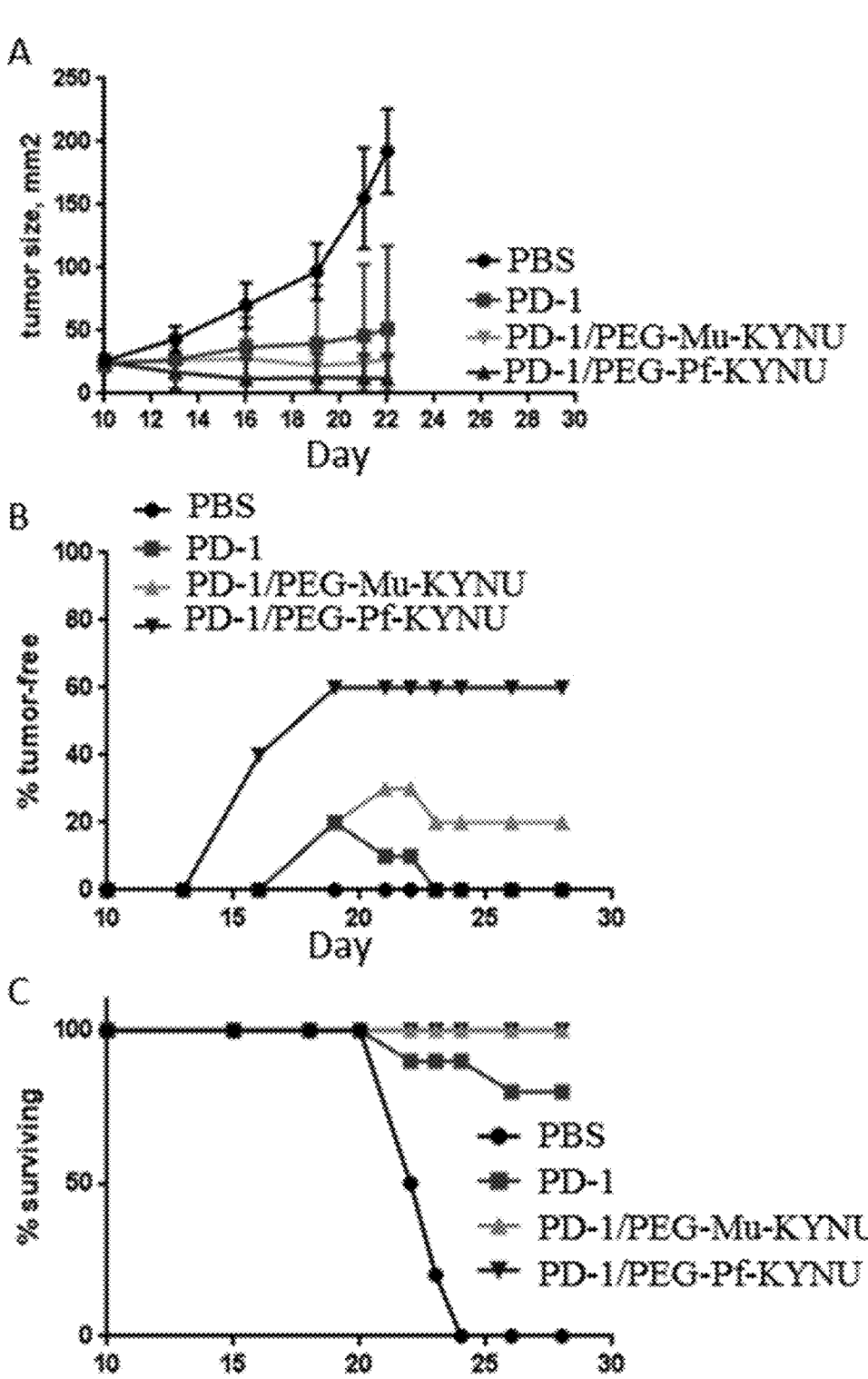
FIGS. 9A-9C— FIG. 9A—C57BL/6J bearing B16 tumor allografts treated with PBS (circle) (control), Programmed Cell Death Protein 1, or PD1 (antibody) alone (square), PD1 (antibody)/PEG-Mu-KYNU (upside-down triangle), or PD1 (antibody)/PEG-Pf-KYNU (right-side up triangle).

Example 22—Efficacy of Mu-KYNU or Pf-KYNU and Anti-PD1 Combination Therapy in the Autologous B16 Mouse Melanoma Model The PEGylated enzymes (PEG-Pf-KYNU and PEG-Mu-KYNU) were evaluated in B16 melanoma allografts in combination with the anti-PD1 immune checkpoint inhibitor antibody (Curran et al., 2010). Four groups of C57BL/6J mice (10 per group) were implanted with 50,000 B16 cells (Day 0) and tumors were allowed to develop. Once palpable tumors developed (Day 10), the animals were treated with 250 µg anti-PD1 by IP injection (clone RMP1-14, BioXCell #BE0146) on days 10, 13, and 16 either with or without 500 µg PEG-Pf-KYNU or 500 µg PEG-Mu-KYNU s.c. near the tumor site. Mice received a total of six doses of KYNU between days 10 and 25. One group was given PBS injections i.p. as a control for PD-1. Tumor growth was drastically impaired or even reversed in all treatment arms compared to PBS control (FIG. 9A). Importantly, additive effects were observed with anti-PD1 in combination with KYNU resulting in complete remission of 60% of the tumors with PEG-Pf-KYNU/anti-PD1 treatment and 20% of the tumors with PEG-Mu-KYNU/anti-PD1 treatment (FIG. 9B). Corresponding Kaplan-Meier plots are provided in FIG. 9C.

Figures 10A, 10B:
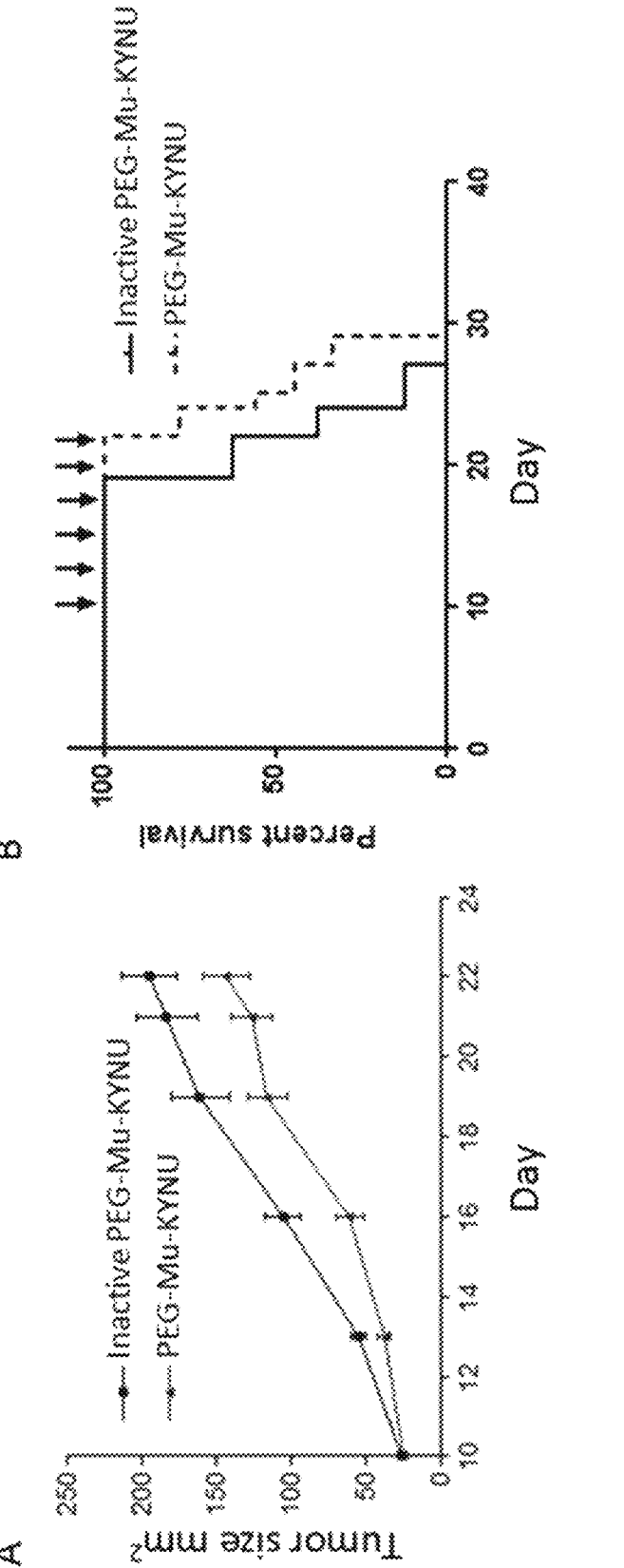
FIGS. 10A-10B— FIG. 10A—C57BL/6J bearing B16 tumor allografts treated with heat-inactivated PEG-Mu-KYNU (■) or active PEG-Mu-KYNU (▲).

Example 23—Efficacy of PEG-Mu-KYNU Therapies in the Autologous B16 Mouse Melanoma Model The PEGylated *Mucilaginibacter paludis* kynureninase (PEG-Mu-KYNU) was evaluated in the B16 melanoma mouse model. Allografts were initiated by implanting 50,000 B16 cells in the flanks of C57BL/6J mice (Day 0, n=9 mice per group). Once palpable tumors developed (Day 10), the animals were treated with 500 µg of PEG-Mu-KYNU by subcutaneous injection near the tumor site every three days for a total of 6 doses. An identical treatment regimen with heat-inactivated PEG-Mu-KYNU was used as a control. Administration of PEG-Mu-KYNU resulted in tumor growth retardation (FIG. 10A) with an extended median survival time of 25 days compared to 22 days for the heat-inactivated PEG-Mu-KYNU control (FIG. 10B).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 5,889,155
U.S. Pat. No. 7,109,304
U.S. Pat. No. 8,465,743
U.S. Pat. Publn. 2009/0304666
WO 2012/031744
WO 2012/079000
WO 2013/059593
Ahmed et al., HER2-specific T cells target primary glioblastoma stem cells and induce regression of autologous experimental tumors. *Clinical Cancer Research*, 16(2): 474-485, 2010.
Austin-Ward and Villaseca, *Revista Medica de Chile*, 126 (7):838-845, 1998.
Ausubel et al., Current Protocols in Molecular Biology, Greene Publishing Associates and Wiley Interscience, N.Y., 1994.
Bukowski et al., *Clinical Cancer Res.*, 4(10):2337-2347, 1998.
Chen and Guillemin, Kynurenine pathway metabolites in humans: disease and healthy States. *Int J Tryptophan Res*, 2:1-19, 2009.
Christodoulides et al., *Microbiology*, 144(Pt 11):3027-3037, 1998.
Curran et al., PD-1 and CTLA-4 combination blockade expands infiltrating T cells and reduces regulatory T and myeloid cells within B16 melanoma tumors. *Proceedings of the National Academy of Sciences*, 107:4275-4280, 2010.
Davidson et al., *J. Immunother.*, 21(5):389-398, 1998.
de Jong et al., Serum tryptophan and kynurenine concentrations as parameters for indoleamine 2,3-dioxygenase activity in patients with endometrial, ovarian, and vulvar cancer. *Int J Gynecol Cancer*, 21(7):1320-1327, 2011.
Della Chiesa et al., The tryptophan catabolite L-kynurenine inhibits the surface expression of NKp46- and NKG2D-activating receptors and regulates NK-cell function. *Blood*, 108(13):4118-4125, 2006.
Godin-Ethier et al., Indoleamine 2, 3-Dioxygenase Expression in Human Cancers: Clinical and Immunologic Perspectives. *Clinical Cancer Research*, 17(22):6985-6991, 2011.
Hanibuchi et al., Int. J. *Cancer*, 78(4):480-485, 1998.
Harkki et al., *BioTechnology*, 7:596-603, 1989.
Hellstrand et al., *Acta Oncologica*, 37(4):347-353, 1998.
Hollander, Front. *Immun.*, 3:3, 2012.
Holmgaard et al., Indoleamine 2, 3-dioxygenase is a critical resistance mechanism in antitumor T cell immunotherapy targeting CTLA-4. *The Journal of Experimental Medicine*, 210:1389-1402, 2013.
Hoover and Lubkowski, DNAWorks: an automated method for designing oligonucleotides for PCR-based gene synthesis. *Nucleic Acids Research*, 30(10):e43-e43, 2002.
Hopwood et al., In: *Genetic Manipulation of Streptomyces*, A Laboratory Manual, The John Innes Foundation, Norwich, Conn., 1985.
Hui and Hashimoto, *Infection Immun.*, 66(11):5329-5336, 1998.
Ito et al., *J. Biochem.*, 79:1263, 1976.
Kaper et al., Nanosensor detection of an immunoregulatory tryptophan influx/kynurenine efflux cycle. *PLoS Biology*, 5(10):e257, 2007.

Lipowska-Bhalla et al., Targeted immunotherapy of cancer with CAR T cells: achievements and challenges. *Cancer Immunology Immunotherapy,* 61(7):953-962, 2012.

Lob et al., Inhibitors of indoleamine-2,3-dioxygenase for cancer therapy: can we see the wood for the trees? *Nat Rev Cancer,* 9(6):445-452, 2009.

Lordanescu, *J. Bacteriol,* 12:597 601, 1975.

Mandi and Vecsei, The kynurenine system and immuno-regulation. *J Neural Transm,* 119(2):197-209, 2012.

Maniatis, et al., Molecular Cloning, A Laboratory Manual, Cold Spring Harbor Press, Cold Spring Harbor, N.Y., 1988.

Mellor et al., *Gene,* 24:1-14, 1983.

Mezrich et al., An interaction between kynurenine and the aryl hydrocarbon receptor can generate regulatory T cells. *The Journal of Immunology,* 185(6):3190-3198, 2010.

Opitz et al., The Indoleamine-2, 3-Dioxygenase (IDO) Inhibitor 1-Methyl-D-tryptophan Upregulates IDOL in Human Cancer Cells. *PLoS One,* 6(5):e19823, 2011.

Opitz et al., An endogenous tumour-promoting ligand of the human aryl hydrocarbon receptor. *Nature,* 478(7368): 197-203, 2011.

Penttila et al., *Gene,* 61:155-164, 1987.

Pilotte et al., Reversal of tumoral immune resistance by inhibition of tryptophan 2,3-dioxygenase. *Proc Natl Acad Sci USA,* 109(7):2497-2502, 2012.

Prendergast, Cancer: Why tumours eat tryptophan. *Nature,* 478(7368):192-194, 2011.

Qin et al., *Proc. Natl. Acad. Sci. USA,* 95(24):14411-14416, 1998.

46

Remington's Pharmaceutical Sciences, 18th Ed. Mack Printing Company, 1289-1329, 1990.

Rutella et al., Targeting indoleamine 2,3-dioxygenase (IDO) to counteract tumour-induced immune dysfunction: from biochemistry to clinical development. *Endocr Metab Immune Disord Drug Targets,* 9(2):151-177, 2009.

Schellenberger et al., *Nature Biotech.,* 27:1186-1190, 2009.

Shin et al., Modulation of natural killer cell antitumor activity by the aryl hydrocarbon receptor. *Proc Natl Acad Sci USA,* 110(30):12391-12396, 2013.

Sibakov et al., Eur. *J. Biochem.,* 145:567 572, 1984.

Song et al., L-Kynurenine-induced apoptosis in human NK cells is mediated by reactive oxygen species. *International Immunopharmacology,* 11(8):932-938, 2011.

Stone et al., Replacing $Mn^{2+}$ with $Co^{2+}$ in human arginase I enhances cytotoxicity toward L-arginine auxotrophic cancer cell lines. *ACS Chemical Biology,* 5:333-342, 2010.

Ward, Proc, Embo-Alko Workshop on Molecular Biology of Filamentous Fungi, Helsinki, 119-128, 1989.

Wawrzynczak and Thorpe, In: *Immunoconjugates, Antibody Conjugates In Radioimaging And Therapy Of Cancer,* Vogel (Ed.), NY, Oxford University Press, 28, 1987.

Yao et al., Serum metabolic profiling and features of papillary thyroid carcinoma and nodular goiter. *Mol Biosyst,* 7(9):2608-2614, 2011.

Yoshikawa et al., Serum concentration of L-kynurenine predicts the clinical outcome of patients with diffuse large B-cell lymphoma treated with R-CHOP. *Eur J Haematol,* 84(4):304-309, 2010.

What is claimed is:

1. A plasmid comprising a nucleic acid that encodes a polypeptide comprising a kynureninase enzyme comprising an amino acid sequence that is at least 90% identical to SEQ ID NO: 8, and having one or more substitutions relative to SEQ ID NO: 8, wherein the one or more substitutions comprise a substitution of the Phe found at position 306 of SEQ ID NO: 8.

2. The plasmid of claim 1, wherein the one or more substitutions comprise Phe306Met.

3. The plasmid of claim 1, wherein the one or more substitutions comprise Phe306Leu.

4. The plasmid of claim 1, wherein the nucleic acid further comprises a polynucleotide encoding a heterologous peptide segment.

5. The plasmid of claim 4, wherein the heterologous peptide segment is an XTEN peptide, an IgG Fc, an albumin, or an albumin binding peptide.

6. The plasmid of claim 1, wherein the nucleic acid is codon optimized for expression in bacteria, fungus, insects, or mammals.

7. The plasmid of claim 1, wherein the encoded enzyme has an amino acid sequence that is at least 95% identical to SEQ ID NO: 8.

8. The plasmid of claim 1, wherein the one or more substitutions comprise a conservative substitution of the Phe found at position 306 of SEQ ID NO: 8.

9. A host cell comprising the plasmid of claim 1.

10. The host cell of claim 9, wherein the host cell is a bacterial cell.

11. The host cell of claim 9, wherein the host cell is a fungal cell.

12. The host cell of claim 9, wherein the host cell is an insect cell.

13. The host cell of claim 9, wherein the host cell is a mammalian cell.

14. A pharmaceutical formulation comprising:

(i) a plasmid comprising a nucleic acid that encodes a polypeptide comprising a kynureninase enzyme, wherein the kynureninase enzyme comprises an amino acid sequence that is at least 90% identical to SEQ ID NO: 8 and has one or more substitutions relative to SEQ ID NO: 8, wherein the one or more substitutions comprise a substitution of the Phe found at position 306 of SEQ ID NO: 8; and (ii) a pharmaceutically acceptable carrier.

15. The formulation of claim 14, wherein the encoded enzyme has greater catalytic activity towards kynurenine than 3'-OH kynurenine.

16. The formulation of claim 14, wherein the encoded enzyme has a kcat/KM for kynurenine of at least 0.5 $M^{-1}/s^{-1}$.

17. A method of producing a polypeptide comprising a kynureninase enzyme, wherein the kynureninase enzyme comprises an amino acid sequence that is at least 90% identical to SEQ ID NO: 8 and has one or more substitutions relative to SEQ ID NO: 8, wherein the one or more substitutions comprise a substitution of the Phe found at position 306 of SEQ ID NO: 8, the method comprising:

(i) providing a plasmid comprising a nucleic acid that encodes the polypeptide;

(ii) introducing the plasmid into a host cell under conditions sufficient for the host cell to express the polypeptide; and (iii) isolating the polypeptide from the host cell.

18. The method of claim 17, wherein the host cell is a bacterial cell, fungal cell, insect cell, or mammalian cell.

\* \* \* \* \*